US007050208B2

(12) United States Patent
Overbeck

(10) Patent No.: US 7,050,208 B2
(45) Date of Patent: May 23, 2006

(54) SCANNING MICROSCOPY, FLUORESCENCE DETECTION, AND LASER BEAM POSITIONING

(76) Inventor: James W. Overbeck, 112 Martins La., Hingham, MA (US) 02043

( * ) Notice: Subject to any disclaimer, the term of this patent is extended or adjusted under 35 U.S.C. 154(b) by 28 days.

(21) Appl. No.: 10/305,696

(22) Filed: Nov. 26, 2002

(65) Prior Publication Data

US 2003/0156323 A1 Aug. 21, 2003

Related U.S. Application Data

(60) Provisional application No. 60/333,795, filed on Nov. 28, 2001.

(51) Int. Cl.
*G02B 26/08* (2006.01)
(52) U.S. Cl. .................. 359/201; 359/205; 359/212
(58) Field of Classification Search ................ 359/209, 359/210, 212–219, 221, 197, 201, 205, 206; 356/300, 319, 326, 501, 639, 640
See application file for complete search history.

(56) References Cited

U.S. PATENT DOCUMENTS

| 3,746,427 A | 7/1973 | Foster |
| 3,962,688 A | 6/1976 | Westerberg |
| 4,164,717 A | 8/1979 | Blazey |
| 4,180,822 A | 12/1979 | Hudson et al. |
| 4,193,087 A | 3/1980 | Altman |
| 4,246,612 A * | 1/1981 | Berry et al. ................. 348/203 |
| 4,272,151 A | 6/1981 | Balasubramanian |
| 4,401,886 A | 8/1983 | Pond et al. |
| 4,532,402 A | 7/1985 | Overbeck |
| 4,725,709 A | 2/1988 | Mattelin |
| 4,736,110 A | 4/1988 | Awamura |
| 4,827,125 A * | 5/1989 | Goldstein ................... 250/234 |
| 4,872,746 A | 10/1989 | Kobayashi |
| 5,091,652 A | 2/1992 | Mathies et al. .......... 250/458.1 |
| 5,110,195 A | 5/1992 | Loney |
| 5,121,247 A | 6/1992 | Fujita |
| 5,225,923 A | 7/1993 | Montagu |
| 5,262,707 A | 11/1993 | Okazaki et al. |
| 5,268,554 A | 12/1993 | Ream |
| 5,274,492 A | 12/1993 | Razzaghi |
| 5,416,298 A | 5/1995 | Roberts |
| 5,430,509 A | 7/1995 | Kobayashi |
| 5,452,275 A | 9/1995 | Ogawa |

(Continued)

FOREIGN PATENT DOCUMENTS

EP    0 056 426    7/1982

(Continued)

*Primary Examiner*—Drew A. Dunn
*Assistant Examiner*—Joshua L. Pritchett
(74) *Attorney, Agent, or Firm*—Fish & Richardson P.C.

(57) ABSTRACT

High speed, wide area microscopic scanning or laser positioning is accomplished with an inertia-less deflector (for example an acousto-optic or electro-optic deflector) combined with a high speed wide area microscopic scanning mechanism or laser positioner mechanism that has inertia, the motion of the inertia-less deflector specially controlled to enable a focused spot to stabilize, for example to stop and dwell or be quickly aimed. It leads to improved data acquisition from extremely small objects and higher speed operation. In the case of fluorescence reading of micro-array elements, dwelling of fluorophore-exciting radiation in a spot that is relatively large enables obtaining the most fluorescent photons per array element, per unit time, a winning criterion for reducing fluorophore saturation effects. The same inertia-less deflector performs stop and dwell scanning, edge detection and raster scans. Automated mechanism for changing laser spot size enables selection of spot size optimal for the action being performed.

68 Claims, 42 Drawing Sheets

U.S. PATENT DOCUMENTS

| | | | |
|---|---|---|---|
| 5,532,873 A | 7/1996 | Dixon | 359/388 |
| 5,535,052 A | 7/1996 | Jörgens | 359/388 |
| 5,653,900 A | 8/1997 | Clement et al. | |
| 5,691,839 A | 11/1997 | Kobayashi | |
| 5,751,585 A | 5/1998 | Cutler et al. | |
| 5,798,927 A | 8/1998 | Cutler et al. | |
| 5,837,962 A | 11/1998 | Overbeck | |
| 5,841,892 A * | 11/1998 | McGrath et al. | 382/141 |
| 5,936,764 A | 8/1999 | Kobayashi | |
| 6,075,643 A | 6/2000 | Nonoda et al. | 359/385 |
| 6,185,030 B1 | 2/2001 | Overbeck | |
| 6,201,639 B1 | 3/2001 | Overbeck | |
| 6,351,324 B1 * | 2/2002 | Flint | 359/202 |
| 6,366,357 B1 * | 4/2002 | Svetkoff et al. | 356/602 |
| 6,628,385 B1 * | 9/2003 | Osipchuk et al. | 356/318 |

FOREIGN PATENT DOCUMENTS

| | | |
|---|---|---|
| EP | 0 615 721 | 9/1994 |
| EP | 0 620 468 | 10/1994 |
| GB | 2 133 352 | 7/1984 |
| JP | 57-47593 | 3/1982 |
| JP | 60-40682 | 3/1985 |
| JP | 3-198988 | 8/1991 |
| JP | 07-116869 | 5/1995 |

* cited by examiner

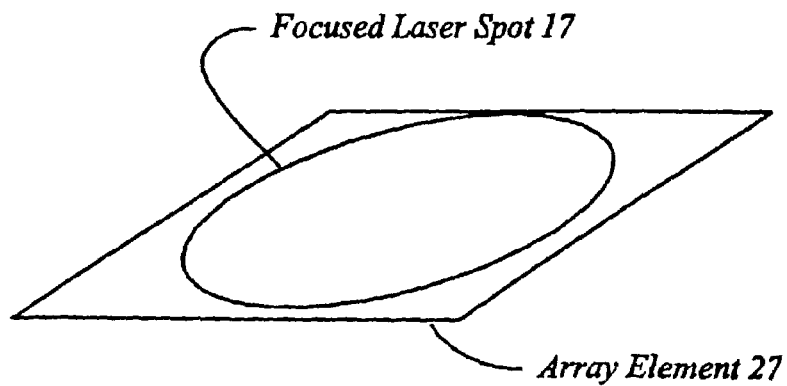
Figure 6B
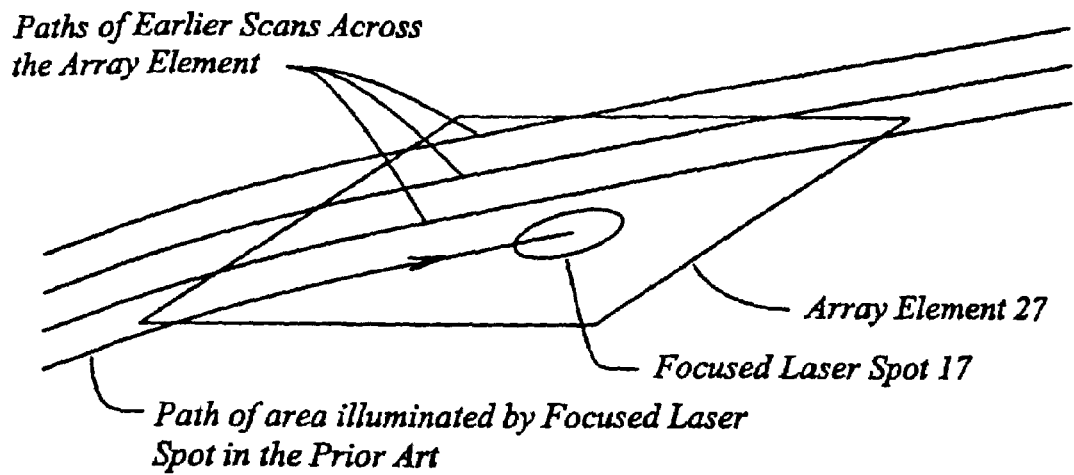
Figure 6A -- Prior Art

*Memory Addressing and Boundary Crossing Switch*

*Data Accumulation and Storage*

*Control of Acousto-Optic Deflectors and Rejection of Data*

*Timing*

*Synchronization*

Block shown for X Axis Acousto-Optic Deflector.
An Identical Block controls the Y Axis Acousto-Optic Deflector.

*Control of RF Amplitude*

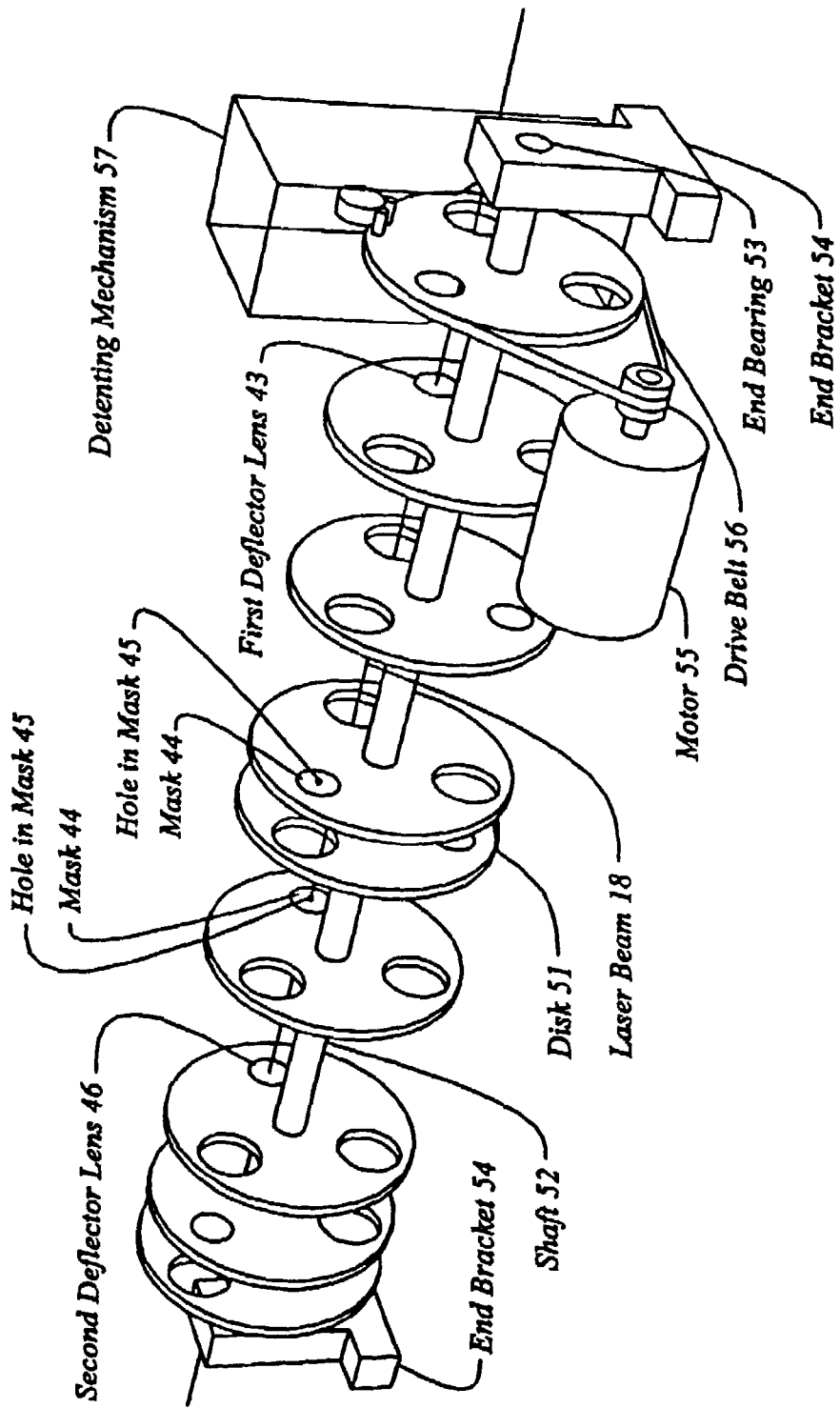
*Figure 20A  Variable Spot Size Mechanism 50*

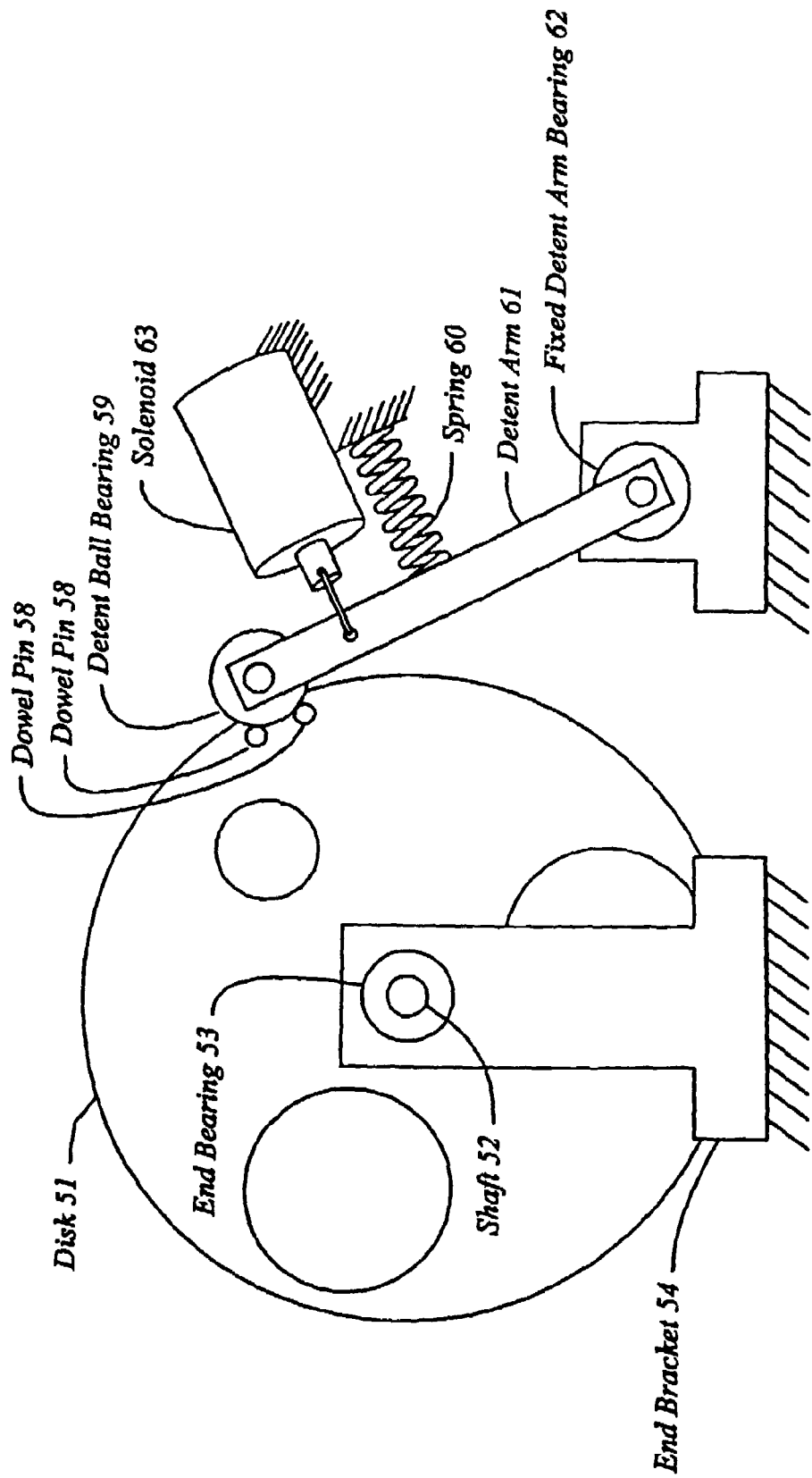
Figure 20B  Detenting Mechanism 57

*Background Software Task*

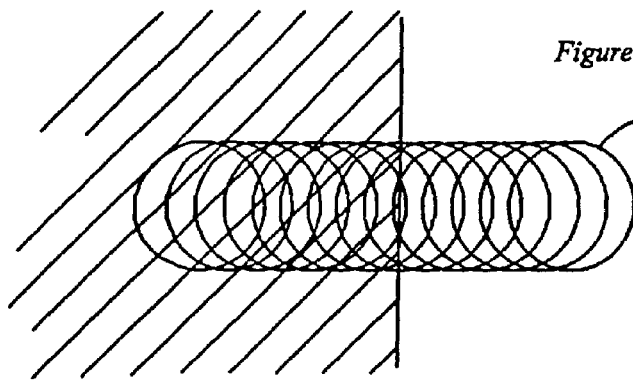

*Figure 26A  Plan View*

Focused Laser Spot
1/e Squared Diameter Shown

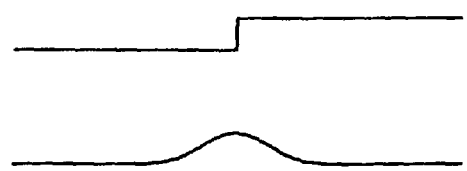

*Figure 26B*

QA  Amount of Light vs Distance in case of zero spot size

*Figure 26C*

QB  Actual Laser Spot Size

*Figure 26D*

QC  Measured Amount of Light vs Distance

*Figure 26E*

QD  Derivative of QB

*Figure 26F*

QE  Convolution of QC and QD

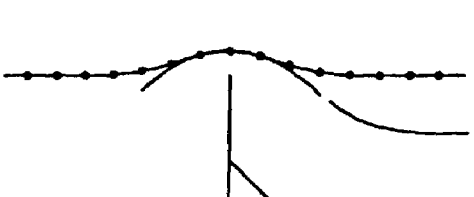

QF  Best Fit Parabola to Top Three Data Points of QE. Its center defines the measured edge location.

QG  Best Estimate of Location of Edge

SCANNING MICROSCOPY, FLUORESCENCE DETECTION, AND LASER BEAM POSITIONING

This application claims priority under 35 USC §119(e)(1) to U.S. Provisional Application Ser. No. 60/333,795, filed on Nov. 28, 2001, the entire contents of which are hereby incorporated by reference.

COMPUTER PROGRAM LISTING APPENDIX

A Computer Program Listing Appendix is included at the end of this patent specification and on a computer disc. It is readable by the Microsoft Windows operating system and contains six C language computer programs in ASCII text form, as follows:

| Name | Size in Bytes | Date of Creation of CD |
|---|---|---|
| fs_algorithm.c | 14286 | Oct. 30, 2001 |
| fs_fast_algorithm.c | 21417 | Oct. 30, 2001 |
| fs_fast.c | 18549 | Oct. 30, 2001 |
| fs_main.c | 1412 | Oct. 30, 2001 |
| fs_support.c | 7922 | Oct. 30, 2001 |
| simul_motion.c | 10084 | Oct. 30, 2001 |

The entire contents of this Computer Program Listing Appendix are hereby incorporated by reference.

BACKGROUND

This invention concerns improved data acquisition techniques in wide field, high speed laser microscopy, improvement in the life science specialty of bioinformatics and improvement in laser beam positioning. In particular, important aspects of the invention improve the scanning of micro-arrays for fluorescence.

As is well known, bioinformatics concerns the rapid acquisition and analysis of biological data from physically large areas of differing biological material, such as from micro-arrays. When a laser scans a micro-array, and is used to excite fluorescence from such arrays, it becomes possible, in only a few minutes, to measure accurately the amount of messenger RNA representing each of more than 10,000 different genes in a cell.

This has lead to breakthroughs in the understanding of the functioning of genes and cells, and is expected to lead to expedited drug discovery, and improvement in clinical analysis, diagnosis and treatment. Advance in bioinformatics, among other things, depends upon increasing the speed of acquisition of microscope data from micro-arrays and increasing the size of the data set, at less cost per measurement.

These demands translate to the requirement for decreasing the size and spacing of each array element to be optically scanned, and decreasing the scan time allotted to acquiring data from each element.

This applies to many different kinds of micro-arrays, including those containing synthetic oligonucleoitides produced by photolithographic techniques, and those comprising spots of genetic material or proteins deposited on microscope slides by ink-jet printing or other techniques. There is likewise a need for higher speed, high resolution microscopic examination of tissue and other biological samples.

Wide field laser microscopy of micro-arrays has employed a laser beam that moves generally continuously over the array, scanning across discrete array elements or features in succession over the length of a scan path. The result is detected by reflection, transmission, and in particularly important cases, by fluorescence, using edge detection techniques to disregard data acquired in the dead space as the beam moves between features of the array.

To quickly obtain an adequate response from features that have been made smaller and more closely packed, one desires to decrease the size of the beam and increase its intensity. However, in the very important case of use of fluorescent molecules as tags ("fluorophores"), a limit is encountered because of saturation characteristics of the fluorophore, i.e. there is delay between the time of excitation of the fluorophore by an incident photon and the time of its emitting its fluorescing photon, during which, another photon incident on that fluorophore can have no effect and would be wasted. For instance, the fluorophore saturation limit may be encountered when seeking to reduce the size of a photolithographic array element from 20 micrometers square to 10 micrometers square.

The fragility or energy-sensitivity of biological material itself can also limit the permissible intensity of the beam.

In these cases, the simultaneous reduction of feature size and laser spot size results in a greatly increased waste of laser photons, and a decreased amount of fluorescent light per feature, hence scanning is forced to proceed at slower rate than desired.

A limit similar to that of fluorophore saturation may be encountered when using a laser beam to heat or otherwise excite array elements or other discrete small regions of a surface. Excessive heat may result in unwanted damage or unwanted chemical reactions.

More generally, there is a need for increased speed and accuracy in performing examination and other tasks in wide area scanning microscopy.

SUMMARY OF THE INVENTION (a) In General

According to one aspect of the invention, it is realized that combination of an inertia-less deflector with a wide area microscopic scanner or positioner that has inertia, the motion of the inertia-less deflector programmed to enable a "stop and dwell" action of the focused laser spot on the object, leads to improvement in the rate of data acquisition from the object.

According to an aspect of the invention, it is realized that, for a given wide field, high speed laser microscopy scanning system, introducing into the optic train an inertia-less deflector (for example an acousto-optic or electro-optic deflector), and programming it to revise the scanning speed of the laser spot across the object, to cause the laser beam to stop and "dwell" momentarily at each feature, then rapidly advance to the next, leads to advantages such as higher sensitivity and throughput. In particular, significant improvement can be obtained in reading fluorescence from micro-arrays.

It is further realized, that, by momentary use of the inertia-less deflector for another purpose, to detect the edge of the feature, or to otherwise ensure the known position of the beam relative to the outline of the feature, the incident region of the beam can be located inwardly from the edge, and may be enlarged in dimension, effectively permitting more area of the feature, or in some cases, the entire central area of the feature, to be "dwelled upon" by the appropriate intensity beam. Importantly, in the case of fluorescence reading of array elements, such dwelling of fluorophore-exciting radiation in a spot the area of which is a significant fraction of the area of an element enables obtaining the most fluorescent photons per array element, per unit time. According to the invention, this is realized to be a winning criterion for reducing fluorophore saturation effects.

In another system, where random access of the laser beam to a feature address is desired, in similar way, again the inertia-less deflector added to the system is programmed to achieve stoppage of the laser spot on the object, effectively canceling settling motions of the wide area mechanical scanning system as it seeks to settle at the address, the inertia-less deflector controlled by feedback that detects the settling motions of the mechanical system, and drives the inertia-less deflector oppositely.

In such systems as described, the inertia-less deflector can be programmed to execute other desirable tasks, for instance to shift from one region of the feature to another, in a "multi-dwell" examination of a feature. Likewise, in conjunction with a dynamically controllable beam diameter system, the system may be employed to produce a "stop-dwell" X, Y or raster scan of an area, each pixel produced by a constant dwell, as above, the system being shiftable to a higher resolution mode upon detecting a region of interest, in which the beam reduces in diameter, and is caused to execute a raster pattern at higher resolution.

In another multi-mode arrangement, a program is provided to de-energize the inertia-less deflector, to enable the basic scanning system to perform a conventional scan to provide supplemental information, for instance feature position information for the bioinformatics data bank, or as an initial prescan, to precisely locate the features, the map of which is then employed in the stop and dwell routine, to accurately direct the beam to dwell upon the center or other desired region or regions of the feature. For such modes of operation the inertia-less deflector may be advantageously employed to attenuate the beam and decrease the intensity of the laser spot.

Another aspect of the invention employs the inertia-less "stop-dwell" microscope action on other objects, to illuminate, energize, or otherwise probe a feature under constant conditions during the period of the dwell, in conjunction with high speed scanning of the array of addresses by an otherwise constantly moving, and hence advantageous system, that for instance can avoid unreasonably high accelerations, vibrations and power dissipation.

Still other aspects of the invention concern unique software algorithms and routines that enable performance of the various scanning modes and other advantageous methods and procedures, and in general, the improvement of laser positioning by use of actions as described above.

(b) Objects of the Invention

Objects of the invention include:

Reducing fluorophore saturation problems.

Improving throughput in scanning fluorescent arrays.

Increasing the accuracy and efficiency of measurements of fluorescence from arrays.

Enabling use of an increased diameter of a focused laser spot, and so reducing sensitivity to focus, allowing inexpensive focusing means, reduced time devoted to focusing, and increased tolerance to lack of flatness in workpieces.

Enabling the reduction of the size of fluorescent features below the present sizes, and enabling increase in the number of such features per array by providing an effective scanner for such features.

Maintaining a high signal to noise ratio in detecting fluorescence and thereby keeping low the detection threshold of the fluorescent scanner.

Enabling ultra high speed wide area fluorescence scanning with a flying lens, useful with micro-arrays of extremely high density.

Enabling efficient use of slow and relatively inexpensive X, Y stages for many of the purposes above. Such use of X, Y stages also enables coverage of larger workpieces than can be efficiently covered by scanners such as those using galvanometers. Use of such X, Y stages also enables the use of high numerical aperture focusing lenses such as a microscope objective, which are too massive for use with flying lens scanners or other scanners which use high accelerations.

Enabling the use of conventional X, Y stages with readily available precision feedback transducers such as laser interferometers and linear encoders.

Enabling the efficient use of laser beams for purposes other than exciting fluorescence, such as applying controlled amounts of heat to arrays for chemical analysis of the array elements.

Enabling a scanner, at a high speed, to simultaneously, A. stimulate fluorescence with a focused laser beam, B. collect fluorescent light efficiently and, with confocal optics, C. collect fluorescence information over an area large compared with that covered by a microscope objective.

Further objects of the invention will be understood from the following detailed summary and description of the drawings illustrating embodiments of the invention.

(c) Detailed Summary

According to the invention, a microscope scanner is provided, for instance a fluorescence scanner, comprising scanning apparatus constructed and controlled to scan a focused spot (e.g. a laser spot) over locations on an extended surface, addressed by the optical path from a focusing lens, characterized in that the scanning apparatus includes an inertia-less deflector and a deflector control adapted to cause the inertia-less deflector to change the angle of the optical path within a limited range during the scan in a manner to cause the focused spot to stabilize, for example to stop or dwell, upon a respective location on the surface while motion of another portion of the scanning apparatus continues.

Various embodiments have one or more of the following additional features:

The deflector is associated with a set of deflector lenses that direct a beam to a constant position on the focusing lens over a range of deflection of said deflector.

The deflector comprises at least two inertia-less deflector modules arranged to act along different coordinates.

A portion of the scanning apparatus having inertia is constructed to advance the scan along a predetermined scan path over the surface, and the control for the inertia-less deflector is adapted to cause the deflector to change the angle of the optical path progressively in the direction opposite to said advance along the scan path to cause the focused spot to dwell upon the respective location on the surface, and in preferred embodiments the deflector control is also adapted to cause the angle of the optical path to advance relatively quickly in the direction of the scan path to change the location upon which the focused spot dwells.

The scanner and said deflector control are adapted to hold said focused spot stationary on a location on said surface for a time between 10 and 1000 microseconds during progress of the scan.

The dwell portion of the repeated duty cycle of the focused spot is at least 90% of the spot duty cycle.

The deflector control is adapted (a) to change the angle of the focused path in one direction at a rate to cause the focused spot to dwell upon a location on the surface during advance of a portion of the scanning apparatus having inertia at an approximately constant speed over a distance at least as large as the dimension of the focused spot in the direction of the scan path, and (b) to change the angle of the focused path in the opposite direction at a substantially faster rate, for example at a rate ten times faster, to shift the incidence of the focus spot to another location on the surface, and in preferred embodiments, the deflector control is adapted to move said focused spot in a direction along said scan, over a distance corresponding to a small multiple of the dimension of the focused spot in the direction along the scan, in a time less than about ten percent of the time in which the focused spot dwells upon a location on the surface.

The scanning apparatus is adapted to scan an area more than ten times the dimension corresponding to the range of deflection of the inertia-less deflector.

A laser produces a laser beam that is deflected by said deflector and travels through the focusing lens to define the focused spot on the surface.

The microscope scanner includes a detector, the focusing lens arranged to gather light from the focused spot and direct it to the detector, and in preferred embodiments, it is a fluorescence detector, and a laser is selected and arranged so that its beam forms the focused spot to excite fluorescence from said location on said surface, and fluorescent light from said location travels through said focusing lens into said fluorescence detector, and further comprising a system for collecting data from said fluorescence detector and assigning said data to respective locations on the surface, and further, in preferred embodiments said fluorescence detector comprises a tube lens, a pinhole, and a photodetector such as a photomultiplier, said focusing lens, said tube lens, and said pinhole combine to effectively form a confocal microscope, and an emission filter arranged to pass fluorescent light to said photodetector and reject laser light.

The inertia-less deflector is associated with a first deflector lens which focuses through a hole in a mask, and a second deflector lens arranged such that said first and second deflector lenses create an image on the focusing lens at the same position on the lens over the range of angles of deflection of said deflector, thereby causing said optical path to rotate about said focusing lens during deflection of said deflector, said mask arranged to block light other than that deflected in first order by said deflector, the focal lengths and locations of said first and second deflector lenses, in conjunction with the initial diameter of a defined input beam and the focal length of said focusing lens determining the diameter of said focused spot on said surface, in preferred embodiments, there also being a lens-changing mechanism, such as a turret, for switching between several sets of said first deflector lens, said mask, and said second deflector lens, enabling the diameter of said focused spot on said surface to be varied by moving said lens-changing mechanism, and in preferred embodiments there being a turret having first and second lens carriers spaced apart along the optical path, carrying respectively all of the first deflector lenses and second deflector lenses, and masks associated with respective lens sets disposed between said lens carriers.

The microscope scanner is adapted to address a succession of features on said extended surface, the deflector control adapted to sweep the focused spot rapidly over edge regions of the features and to dwell for relatively long intervals upon areas of the features inwardly from their edges, and in preferred embodiments successive scan paths of the scanner overlap at least slightly and a control of the scanner identifies locations which have previously been dwelled upon and causes the scanner to pass over said locations without said laser spot dwelling upon them again.

The microscope scanner is associated with software adapted to implement an edge detection algorithm operating on data produced by advance of a focused spot over the surface, the algorithm effective to detect the edges of features at locations on the surface, preferably the software in machine readable form is arranged to fit a curve such as a parabola to ascending and descending points in the convolution of the measured light readings and the derivative of the characteristic power distribution across the laser spot, and to locate the edge of the feature at the maximum value of the curve fitted to the convolution; in preferred embodiments the detected edge information is used in controlling said deflector, in preferred embodiments the microscope scanner being adapted to conduct a pre-scan to detect locations of edges of features on the surface and to utilize that information in a subsequent scan in which the focused spot dwells upon individual features, and in preferred embodiments, excursions of a laser beam over an edge for detecting location of the edge are produced by said inertia-less deflector.

Scanners or similarly constructed beam positioners for other purposes also according to the preferred embodiments have a mode of operation that involves moving a portion of the scanning or positioning apparatus having inertia to a location having a specific address on the surface which is to receive a focused laser spot, characterized in that a position sensor for the portion of the apparatus having inertia is arranged to provide an instantaneous motion signal for said deflector control during settling motions of said portion of said apparatus at said location, and said deflector control is adapted to change the angle of the laser beam in response thereto to move the spot instantaneously with negating motion opposite to the instantaneous settling motions of the portion of the apparatus having inertia, to cause the focused spot to be directed upon the respective location before said settling motions end, in preferred embodiments the settling motion of the portion of the apparatus having inertia and the negating motion produced by said deflector effectively stops said focused spot at said address.

The invention also features a wide range microscope scanner or laser positioner characterized in comprising, in combination, a laser, a focusing lens, and a scanning or positioning apparatus comprising a wide range positioner and an inertia-less deflector, a control system which commands the positions of said wide range positioner and said inertia-less deflector, said combination constructed and arranged to position a focused laser spot on an extended surface, to hold said focused laser spot stationary relative to said surface for a time between 10 and 1000 microseconds, and to move said laser spot a few spot diameters from one specific location on said surface to another in less than ten percent of the interval during which said focused laser spot is stationary, the scanning or positioning apparatus constructed and arranged to address a sequence of at least twenty spot diameters in a scan direction, preferably the microscope scanner or laser positioner being further characterized in that the deflector comprises at least two inertia-less deflector modules arranged to act along different coordinates and the scanning or positioning apparatus is constructed to address an area of at least twenty by twenty spot diameters.

The invention also features, generally, a fluorescent scanner arranged to produce a laser beam that excites fluorescence at locations on a surface characterized by having an acousto-optic deflector or electro-optic deflector that controls fine changes in the angle of the laser beam incident upon the surface to prolong the duration of incidence.

In preferred embodiments of fluorescent and other scanners and laser positioners according to the invention, the diameter of the spot produced by the laser beam on the surface or workpiece is variable.

In preferred embodiments of all of the scanners so far described, and in the methods of scanning, locations on said surface define an array or arrays of biochemical material, in preferred embodiments, including an array of known DNA fragments hybridized with an unknown DNA, in particularly preferred embodiments of this feature, the unknown DNA has attached to it fluorophores with an excitation cross section larger than $4 \times 10^{-20}$ square meters and said focused spot comprises a laser spot of wavelength selected to excite said fluorophores.

In preferred embodiments of the invention, especially those employing "stop and dwell" in fluorescence microscopy, the diameter of the focused spot is larger than one fifth of the X or Y dimensions of features being scanned.

The invention also features a laser beam positioner in which a mechanical component of a positioning apparatus causes a laser beam passing through a focusing lens to move generally continuously, in preferred embodiments, at approximately constant speed, in relation to a surface and an inertia-less deflector, preferably an acousto-optic or electro-optic deflector, responsive to a deflector control, is arranged to change the angle of the laser beam incident upon the surface to produce stepped motion of the beam over the surface.

In scanners or laser beam positioners in preferred embodiments said deflector control for said inertia-less deflector is adapted to keep said focused spot approximately centered on elements of an array.

In scanners or laser beam positioners preferred embodiments operate with a deflector control which generates RF waveforms with sawtooth frequency versus time behavior adapted to cause said deflector to cancel for successive short periods of time, generally continuous motion, in preferred embodiments, at approximately constant speed, between said focusing lens and said surface produced by other portions of the apparatus.

In preferred embodiments of the scanners and laser beam positioners described above the scanning or positioning apparatus includes (a) a wide range positioner which comprises a two dimensional galvanometer scanner, or (b) a wide range positioner which comprises a two dimensional linear positioner which moves said surface relative to said focusing lens, or (c) a wide range positioner which comprises a two dimensional linear positioner which moves said focusing lens relative to said surface, or (d) a wide range positioner which comprises a one or two dimensional linear positioner which moves said focusing lens and a one or two dimensional linear positioner which moves said surface, or (e) a wide range positioner which comprises a one or two dimensional galvanometer scanner and one or two dimensional linear positioner which moves said surface, or (f) a wide range positioner which comprises a one or two dimensional galvanometer scanner and a one or two dimensional linear positioner which moves said galvanometer scanner relative to said surface, or (g) a wide range positioner which comprises a flying lens scanner and a one or two dimensional linear positioner which moves said surface, or (h) a wide range positioner which comprises a flying lens scanner and a one or two dimensional linear positioner which moves said flying lens scanner relative to said surface, or (i) a wide range positioner which comprises a rotating polygon and a one or two dimensional linear positioner which moves said surface, or (j) a wide range positioner which comprises a rotating polygon and a one or two dimensional linear positioner which moves said rotating polygon relative to said workpiece, or (k) a wide range positioner which comprises a rotating turntable which moves the surface formed by one or more workpieces and a linear positioner which moves said focusing lens relative to said turntable, or (l) a wide range positioner which comprises a rotating turntable which moves the surface formed by one or more workpieces and a one or two dimensional galvanometer scanner, or (m) a wide range positioner which comprises a rotating turntable which moves the surface formed by one or more workpieces and a flying lens scanner, or (n) a wide range positioner which comprises a rotating table which moves said focusing lens over the surface formed by one or more workpieces and a one or two dimensional linear positioner which moves said surface, or (o) a wide range positioner which comprises a rotating polygon and a rotating turntable which moves the surface formed by one or more workpieces, or (p) a wide range positioner, the focusing lens being fixed or being moved by said wide range positioner at approximately constant speed during a scan, the focusing lens being a microscope objective.

Another aspect of the invention, with respect to a fluorescence scanner, is a scanning apparatus constructed and controlled to scan a laser beam across an extended surface to excite fluorophores associated with features on the surface and to detect fluorescence with respect to the features scanned, characterized in that the scanning apparatus includes at least one inertia-less deflector associated with a deflector control that changes the angle of the laser beam during scan of a feature to prolong the incidence of the laser spot on the region of the feature inwardly of its boundary during the course of the scan.

Another aspect of the invention is a computer program in machine readable form adapted to perform the steps of converting generally continuous motion to stepped motion across a micro-array of spaced locations of density of at least 400 per square centimeter, preferably, of density of at least 1000 per square centimeter.

The invention also features a medium carrying information configured to cause a microscope scanner or a laser beam positioner to progressively change the angle of a beam passing through it in accordance with generally continuous motion of a mechanical portion of the scanner or beam positioner through which the beam passes, to cause the beam to dwell on a location on an object in a field of at least 400 locations per square centimeter, preferably at least 1,000 locations per square centimeter, and to step to a next feature in the field, and dwell upon it, in a repetitive manner. In preferred embodiments, the medium carrying the information is configured to determine control signals applied to an inertia-less deflector of the microscope scanner or laser beam positioner, preferably the inertia-less deflector being part of a microscope scanner or a laser beam positioner constructed with any of the aspects or features that have previously been described.

Another aspect of the invention is a medium carrying information configured to determine control signals applied to an inertia-less deflector of a microscope scanner or a laser beam positioner to change the angle of a beam passing through it in accordance with motion of a mechanical portion of the scanner or beam positioner through which the beam passes, to cause the beam to stabilize, i.e. stop or dwell, upon a selected location on an object despite the motion of the mechanical portion, in preferred embodiments the medium being configured to determine control signals for an inertia-less deflector which is part of a scanner or laser beam positioner in which the motion comprises settling motion of the mechanical portion of said microscope scanner or laser beam positioner at an address.

The invention also features a medium carrying information configured to cause a machine to superimpose a dwell on motion of a beam that would otherwise be moving continuously across an array of closely-spaced locations.

Another aspect of the invention is a medium carrying information configured to cause a high speed fluorescence scanner to collect fluorescence data based upon periodic dwell of a fluorophore-exciting focused laser beam upon successive features of an array and assign detected data to respective locations on the array.

Still other features of the invention are a method of scanning or positioning a laser beam characterized in employing the computer program or medium of any of the above descriptions, a method of scanning or positioning a laser beam characterized in employing any of the apparatus features that have been described, and a method of scanning or positioning a laser beam characterized in both employing a scanner or laser beam positioner according to any of the embodiments described and in implementing the computer program or employing any of the media just described.

According to another aspect of the invention, a method is provided of reading fluorescence from features arrayed on a surface at density in excess of 400 features per square centimeter, preferably at density in excess of 1000 features per square centimeter, comprising exciting fluorophores of the features by scanning a laser spot over the surface and detecting fluorescent photons from respective features, characterized in that, while scanning proceeds, causing a laser spot, the area of which is a significant fraction of the area of a respective feature, to dwell at a position inwardly from boundary regions of the feature and to step relatively quickly to the next feature. In preferred embodiments, the features are arranged at a density in excess of 10,000 features per square centimeter, in certain preferred embodiments, at density in the range between 40,000 and 1,000,000 features per square centimeter. In preferred embodiments, the laser spot is greater than about five micrometers in dimension, sized to occupy at least about 10% of the area of the feature, and is implemented by the scanner or laser beam positioner of any of the descriptions above.

The invention also features any of the scanners or beam positioners described, further constructed and arranged for randomly accessing features at locations on said surface with said scanning or positioning apparatus and conducting a sweeping scan of a respective feature by said inertia-less deflector. In certain embodiments, the sweeping scan is implemented in a manner to detect the location of features on said surface. In certain embodiments, the inertia-less deflector comprises two inertia-less deflector modules arranged to act along different coordinates and the scanner or positioner is constructed and arranged to conduct a raster scan of said feature, in some cases the raster scan being implemented in a manner to image said feature.

In certain scanners or beam positioners using the above-described features for changing spot size, the apparatus is constructed and arranged to perform a stop and dwell scan of features on a surface employing a first laser spot size and to conduct a sweeping scan or raster scan with a laser spot size smaller than said first spot size.

Another feature of the invention is a microscope scanner, or laser beam positioner, comprising a scanning or positioning apparatus constructed and controlled to scan or position a focused spot (e.g. a laser spot) over locations on an extended surface addressed by the optical path from a focusing lens, the scanning apparatus including an inertia-less deflector and a deflector control, characterized in that said inertia-less deflector is associated with a first deflector lens which focuses through a hole in a mask, and a second deflector lens arranged such that said first and second deflector lenses create an image on the focusing lens at the same position on the lens over the range of angles of deflection of said deflector, thereby causing said optical path to rotate about said focusing lens during deflection of said deflector, said mask arranged to block light other than that deflected in first order by said deflector, the focal lengths and locations of said first and second deflector lenses, in conjunction with the initial diameter of a defined input beam and the focal length of said focusing lens determining the diameter of said focused spot on said surface.

Preferred embodiments of this feature are characterized in further comprising a lens-changing mechanism, such as a turret, for switching between several sets of said first deflector lens, said mask, and said second deflector lens, enabling the diameter of said focused spot to be varied by moving said lens-changing mechanism. In preferred embodiments a turret has first and second lens carriers spaced apart along the optical path, carrying respectively all of the first deflector lenses and second deflector lenses, and masks associated with respective lens sets are disposed between said lens carriers. In preferred embodiments, the deflector comprises at least two deflector modules arranged to act along different coordinates and in preferred embodiments the size of said laser spot is adapted to be varied between a relatively large spot size for reading fluorescence and a smaller size for edge detection or imaging.

BRIEF DESCRIPTION OF FIGURES

FIG. 6A shows a prior art example in which a focused laser spot which is very small compared with an array element scans many times across each element.

FIG. 6B shows a contrasting situation in which a larger focused laser spot dwells on each array element, and then steps very rapidly to the next array element.

FIG. 20A shows a variable spot size mechanism.

FIG. 20B shows a detenting mechanism within the variable spot size mechanism of FIG. 20A.

FIGS. 26A through 26F show the application of the invention to finding the precise locations of edges of features.

Figure 1:
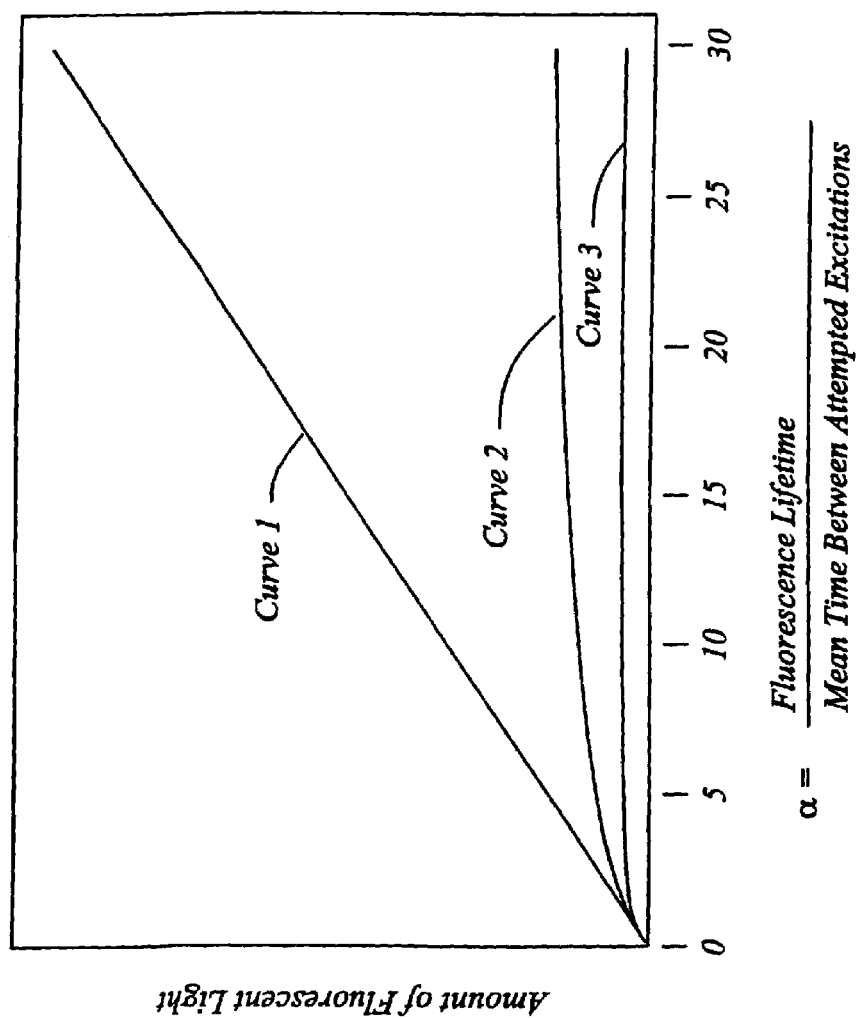
FIG. 1 shows the variation of fluorescent light with incident laser power, showing the effect of fluorophore saturation.

Attention is also called to the Computer Program Listing Appendix that is incorporated by reference.

EMBODIMENTS THAT OVERCOME LIMITS POSED BY FLUOROPHORE SATURATION

As previously mentioned, in microscopic analysis, in many instances fluorescent tags are used to show presence of compounds of interest. A fluorescent molecule, referred to as a fluorophore, after being excited from its ground state, remains in an excited state for a long time by atomic standards, the mean duration of which is typically 4 nanoseconds. This time is referred to as the fluorophore's fluorescence lifetime $\tau$. In practical situations, when the fluorophore de-excites it emits at most one photon, referred to in what follows as a fluorescent photon to distinguish it from the photon which excited the fluorophore. Fluorophores can be excited by light from many sources, by electron beams, etc., but in micro-array and other biochemical applications a traveling focused laser spot has been the most advantageous means of excitation. Therefore in the following discussion we refer to the photon which excited the fluorophore as a laser photon.

In the majority of fluorescence applications the time between excitations is long compared with the fluorescence lifetime. However when scanning over a fluorophore with a focused laser spot the mean time between attempts to excite a fluorophore can become comparable to or less than the fluorescence lifetime. The probability P that a fluorophore will become excited in a short time dt is equal to the product of the number of laser photons incident on the fluorophore per unit area in time dt and the cross section of the fluorophore $\sigma$.

$$P = J_1 \times dt \times \sigma.$$

$J_1$ is the laser photon flux, i.e., the number of incident laser photons per unit area per unit time. The cross section $\sigma$ can be considered an effective area of the fluorophore and is in principle calculated using quantum mechanics. The value of $\sigma$ for typical commercially viable fluorophores is $2 \times 10^{-20}$ square meters. The detection of fluorescence is enhanced by having the cross section be as large as possible, so an unusual fluorophore, R-Phycoerythrin, with a cross section of $50 \times 10^{-20}$ square meters has come into use. In the absence of saturation, detection of fluorescence is also enhanced by having the laser photon flux (i.e. the intensity of the laser spot) be as high as possible short of damaging the workpiece or having the laser be too expensive.

The number of fluorophores per unit area that are in an excited state, denoted by N, increases due to the incident laser flux and decreases due to de-excitation. The number of fluorescent photons emitted per unit time and per unit area $J_2$ is equal to the quantum yield Y times the number of fluorophore de-excitations per unit time and per unit area. For most fluorophores used with micro-arrays Y is greater than 0.5 and less than 1. The laser beam usually spends a time long compared with 4 nanoseconds to move across a fluorophore, so N is approximately constant. In other words, the excitations are in equilibrium with the de-excitations.

The concept of fluorescence lifetime is that it provides a measure of the natural rate of de-excitation of a fluorophore, in the form that the rate of de-excitation is equal to one divided by the fluorescence lifetime.

If the total number of fluorophores per unit area is denoted by $N_0$ the number of fluorophores per unit area which are not excited and therefore are eligible to be excited by an incident laser photon is $N_0 - N$.

The above facts are converted to equations as follows:

$$dN/dt = (N_0 - N)(P/dt) - N/\tau = 0$$

Solving this for the fraction of fluorophores which are excited, $N/N_0$, yields:

$$(N/N_0) = J_1\sigma/(J_1\sigma + 1/\tau)$$

The rate of emission of fluorescent photons per unit area is $$J_2 = Y(N/\tau) = Y(N_0/\tau) \times (J_1\sigma+1/\tau)) \qquad \text{(Equation 1)}$$

I have noted a salient property, which I demonstrate by Equation 1. One can increase laser photon flux $J_1$ as much as one wants, but the fluorescent photon flux will be limited, i.e. it will not exceed $YN_0/\tau$.

I have realized further that the objective in design and use of a high speed fluorescent scanner, should not be to obtain the most fluorescent photons per unit area per unit time, but rather should be to obtain the most fluorescent photons per array element per unit time. According to the invention, I achieve this by illuminating a relatively large fraction of the area of an array element at any instant of illumination, and employ a moderated laser flux (photons per unit area) that reduces fluorophore saturation. The following analysis shows the benefits obtained.

The properties of the Equation 1 are expressed in FIG. 1 in a way that is independent of particular values for cross section, laser photon flux, and fluorescence lifetime. The abscissa of FIG. 1 is a dimensionless number $\alpha$=the laser photon flux at the center of the focused laser spot times $\sigma$ times $\tau$. The number $\alpha$ is therefore also equal to the fluorescence lifetime divided by the mean time between attempts to excite a fluorophore. Examination of Equation 1 shows that in the case of a uniform intensity spot $\alpha=1$ corresponds to $J_2$ being half its asymptotic value in the laser spot.

Curve 3 in FIG. 1 shows $J_2$, the fluorescent photon flux for a uniformly illuminated spot, and Curve 2 in FIG. 1 shows the fluorescent photon flux for a laser spot realizable in practice, which has a Gaussian distribution, i.e., a photon flux which decreases with distance r from the center of the focused laser spot as $\exp(-8(r/w)^2)$, where w is the width of the photon flux distribution between 1/e squared power points. Curve 1 in FIG. 1 shows what the fluorescent photon flux would have been in the absence of saturation.

If one changes the units on both axes of FIG. 1 to photons per square meter per second, the slope of Curve 1 is equal to the number of fluorophores per square meter, $N_0$, times the cross section $\sigma$ times the quantum yield Y. The asymptotic value of Curve 3 in that case is equal to Y times $N_0$ divided by $\tau$.

If a 5 milliwatt laser emitting 532 nanometer light is used, and this laser light is focused into a Gaussian spot whose 1/e squared diameter is 2.5 micrometers, $J_1 = 0.546 \times 10^{28}$ photons per square meter per second. If the cross section $\sigma = 50 \times 10^{-20}$ square meters, the rate of attempts to excite each fluorophore, $J_1\sigma = 27.3 \times 10^8$ per second. This is more than ten times the natural rate of de-excitation, $1/\tau = 2.5 \times 10^8$ per second. This means that more than 90% of the laser power or laser photons achieve no useful result and are wasted.

FIG. 6A shows the small focused spot used to scan arrays at present, in which many scans are made over each array element. FIG. 6B shows, according to the invention, a larger focused laser spot that is incident upon an array element for a dwell period, as the laser spot effectively stops and "stares" at (dwells upon) a relatively large area of the array element. The above analysis shows this to be much more effective.

The analysis so far shows that a larger focused laser spot, provided according to the invention, can maximize the amount of fluorescent light detected. I also realize that other important benefits are obtainable with a larger spot out of consideration that the focus of the laser beam on the array is never perfect. Lack of perfect focus arises from imperfections in the measurement of focus, inaccuracies in the actuators used to move the workpiece into focus, and most seriously, the lack of flatness in the workpiece. Five micrometer deviations from perfect flatness are typical. In general, therefore, the focus will vary as the laser spot scans across the workpiece, and this is equivalent to saying that the diameter of the focused laser spot will vary over the workpiece. For each different spot diameter there corresponds a different value of $\alpha$, and hence a different efficiency in use of the laser photons. To the extent that the focus height of the workpiece is not known accurately everywhere on it, this change in $\alpha$ leads to an error in the measurement of fluorescence.

Figure 2:
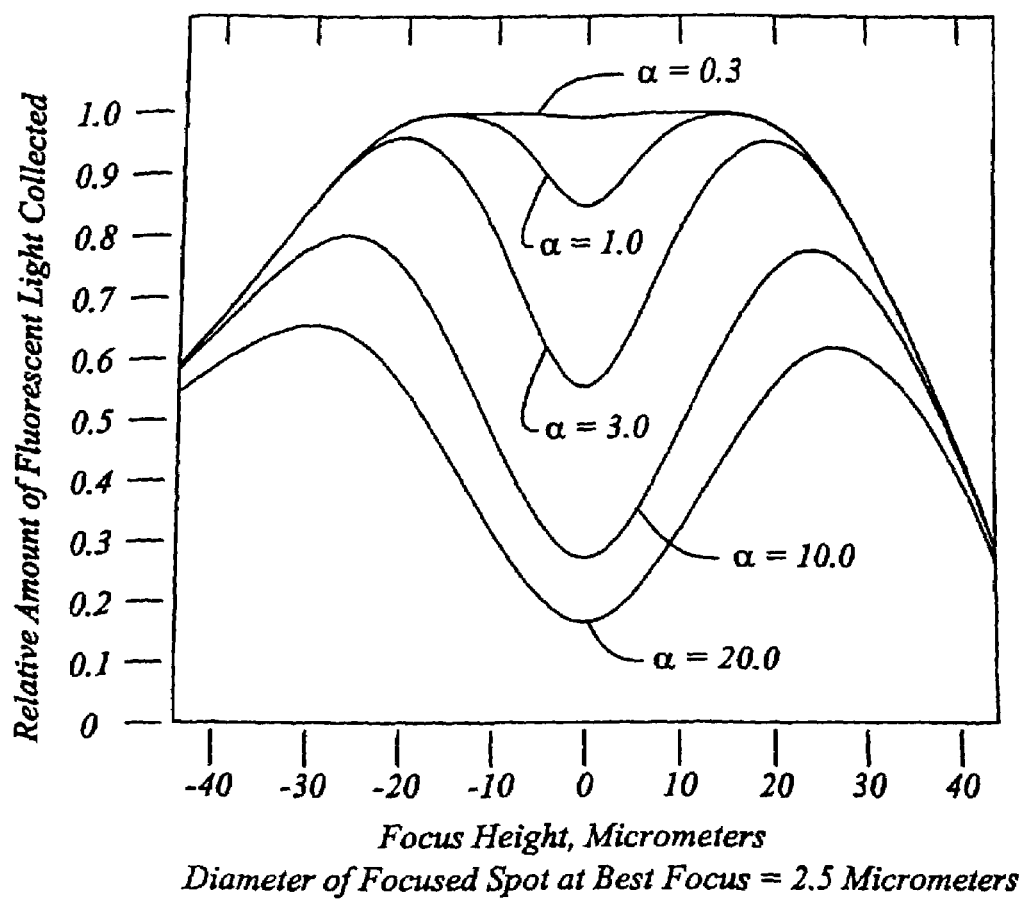
FIG. 2 shows the variation of amount of fluorescent light collected as a function of focus height, for the case of a 2.5 micrometer diameter focused laser spot.

FIG. 2 shows the variation in the measured number of fluorescent photons as focus varies for $\alpha$ at the center of the focused spot=0.3, 1, 3, 10, and 20 for the case that the diameter of the laser spot at best focus is 2.5 micrometers. The dips in the centers of the curves are due to the saturation effect, while the decreases above 20 micrometers above best focus and below 20 micrometers below best focus are due to the action of the pinhole in the confocal microscope that is typically employed to detect fluorescent photons.

A 2.5 micrometer spot has been considered by some as optimum, in the absence of saturation, for scanning in the conventional fashion array elements whose width and height (X and Y dimensions in the plane of the array) are 20 micrometers. With the given desire to decrease size of the array elements and increase the number of them in a given area, one might therefore have considered a 1.25 micrometer spot to be optimum for scanning array elements whose width and height (X and Y dimensions) are 10 micrometers.

Figure 3:
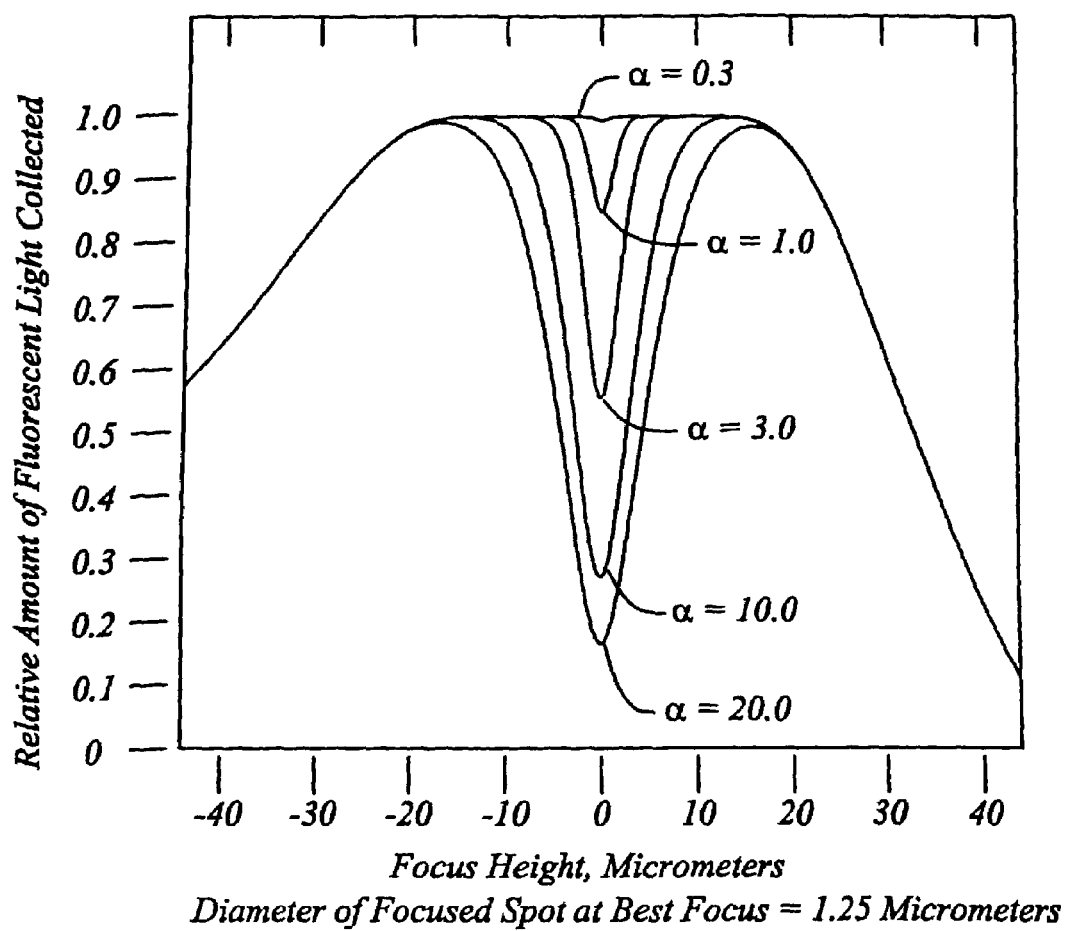
FIG. 3 shows the same quantity as FIG. 2, but for a 1.25 micrometer diameter focused laser spot.

FIG. 3 shows the case of a 1.25 micrometer diameter spot. The rapid variation in fluorescent light with focus implies that sub-micrometer control over focus and flatness would be necessary in order to achieve accurate measurements, which would be impractical or at least only possible with considerable added expense.

I recognize the advantage that, for a given laser power, the laser photon flux $J_1$, and hence the parameter $\alpha$, is proportional to the inverse square of the diameter of the focused laser spot. Therefore, when one uses a 10 micrometer diameter spot centered on a 20 micrometer array element, for example, the value of $\alpha$ is 16 times less than when a 2.5 micrometer spot is used, and the range of focus heights corresponding to a 10% change in spot size is also increased by a factor of 16.

Thus, by using an enlarged spot, as made possible according to the invention, problems with focus and flatness of the workpiece can be dramatically overcome.

When comparing a conventional 2.5 micrometer spot with a 10 micrometer diameter spot, the analysis of saturation above shows that the present invention could provide the ability to utilize 16 times more laser power than with a 2.5 micrometer spot. Scanning continuously with a 2.5 micrometer diameter spot results in about half the time spent collecting fluorescent light from boundary regions and the space between array elements, light which typically is ignored in the measurements. Therefore the present invention can provide as much as 32 times more fluorescent light, and a better signal to noise ratio by a factor of $\sqrt{32}=5.7$, for a given time spent scanning an array, than would be achieved using conventional techniques.

The increased signal to noise ratio implies that practice of this invention can provide a threshold for detecting statistically significant amounts of fluorescence which is 5.7 times lower, for a given scan time, than would be achievable with conventional techniques.

The pair of spot sizes used in the above comparison, 2.5 and 10 micrometers, were chosen to represent currently available feature sizes in micro-arrays produced by photo lithographic techniques, such as 20 micrometers. These spot sizes address a situation in which there is less priority on throughput than on avoiding bright fluorescence in the border region between array elements.

If instead, twice the throughput was desired, and there was not so great a concern about bright border regions, then a 15 micrometer diameter spot would be an appropriate choice for implementation of the present invention and even greater advantages would be obtainable.

The detailed description of the optical design procedure, given later, allows one to pick optimal spot sizes based upon a wide range of criteria. The variable spot size mechanism, described later, enables a scanner to provide these spot sizes. While the illustrated embodiment of the variable spot size mechanism shows only three spot sizes, a mechanism to handle six or ten spot sizes, for example, can readily be provided following these principles.

One system effective for performing this method comprises, in combination, a scanning apparatus comprising an inertia-less deflector and a wide range positioner, a control which comprises computer software and electronic hardware which commands the positions of the wide range positioner and the inertia-less deflector, a laser, a focusing lens, the combination constructed and arranged to position a focused laser spot on an extended surface provided e.g. by a workpiece and to hold the focused laser spot stationary relative to the surface for a time between 10 and 1000 microseconds, and to move the laser spot a few spot diameters from one specific location on the surface to another in less than ten percent of the time during which the focused laser spot is stationary, the scanning apparatus constructed and arranged to address an area of at least twenty by twenty spot diameters, larger than the area the inertia-less deflector could address by itself.

Preferably, the system additionally comprises a fluorescence detector, the laser being selected so that the laser spot excites fluorescence from the addressed location and fluorescent light travels from the location through the focusing lens and into the fluorescence detector, and further comprising computer software and electronics system for collecting data from the fluorescence detector and assigning the data to respective locations on the surface.

Preferably, in the optical train to the detector, a pinhole is arranged in a confocal relationship, such that light from the laser spot passing through the pinhole has a cross-section substantially less than the pinhole, the image being moved over a range within the pinhole dependent upon the range of advance of the scan during a dwell period.

In a preferred embodiment the fluorescence detector comprises a tube lens, a pinhole, and a photodetector such as a photomultiplier, in which the focusing lens, the tube lens, and the pinhole combine to effectively form a confocal microscope, and further comprises an emission filter which passes fluorescent light and rejects laser light.

EXAMPLES OF OTHER EMBODIMENTS

In biological applications in which an array element is deposited as a droplet of liquid, the locations of the individual array elements are not precisely controllable. Therefore it becomes desirable to measure the location of each array element. Measuring such locations has been a byproduct of previous commercial methods of scanning biological arrays, because those methods produce a high resolution picture of the entire array. This high resolution picture has come at a high cost in throughput, and has involved the use of a small focused laser spot, which in turn stimulates the problem of fluorophore saturation that has been overcome by the present invention. According to another aspect of the present invention, provision is included for a preliminary scan of the array, performed rapidly, for the purpose of locating the array elements, spending a small fraction of the time, in an example approximately 20 microseconds per array element, 20 microseconds being typically 10% of the time spent measuring fluorescence from an array element with preferred embodiments of the invention.

In one implementation, during the 20 microsecond time of the preliminary scan, the inertia-less deflector is employed to make a limited number, e.g. ten or more, scans across the periphery of each array element in order to measure its location. Then, once all the locations are known, the normal mode of "stop and dwell" is employed to make accurate measurements of the fluorescence from the array. This is particularly useful for the case of arrays with imperfect geometry.

In another implementation, the wide range positioner of a scanning apparatus is used to scan an array in the same way as was done prior to this invention, except that the scan speed is faster, since the purpose of this scan is not to make accurate fluorescence measurements, but to determine locations, such as the locations of fiducials or bright array elements. During this mode of operation, the inertia-less deflector can be kept at a constant angle during the scan, and so introduces no varying deflection to the beam passing through it. The advantage of this method and system is that existing software for locating the array and for calibrating wide range positioners may be used without modification. Furthermore, the amplitude of the RF waveform applied to the deflector can be reduced to attenuate the beam, e.g. to protect the fluorophores from bleaching during this preliminary scan.

In another implementation or another operating mode, the wide range positioner is capable of random access positioning rather than being confined to fixed-track scanning. For performing a locating function, the wide range positioner moves the laser beam to the neighborhood of successive fiducials, and the inertia-less deflector then is controlled to scan the fiducials. The scanning may be done in raster fashion, providing a picture and exact location of each fiducial, for example, or of other isolated, small regions.

During any of the procedures being described, a variable spot size mechanism may be used to provide a smaller spot than that used for a "stop and dwell" mode of operation, and the amount of laser light may be reduced by controlling the amplitude of the RF waveform sent to the inertia-less deflector.

The general aspect of the present invention that employs a step of finding the location of an array or of individual array elements is not of course restricted to the procedures just described, many other techniques being useful.

Biochemical arrays have recently been used in conjunction with mass spectrometers in order to measure the different masses of molecules present within an array element. For this, a nitrogen laser, providing a very short pulse of light, has been used to dislodge molecules from a substrate. Where it is desired to heat the molecules to a well defined temperature, so that they may undergo specific chemical reactions or evaporation, the mode of motion provided by this invention is employed to advantage. The system is employed to cause a laser beam to dwell for a relatively long time on an array element, and then switch quickly to the next array element, again in a "move, stop and dwell, move" sequence. The system preferably is controlled to avoid collecting information from the boundary areas between array elements, as is the case with detection of fluorescence. This can make use of identical optics, software, and electronics, except for the fact that the components for detecting fluorescent light would not be needed.

Wide range positioners, for example those discussed below, are commonly used in the different field of repair of memory integrated circuits. In these systems a wide range positioner directs a laser beam onto successive conductors or links, which are then vaporized by pulses from a q-switched (very short pulse) laser. The wide range positioners in these systems usually move in "random access mode", rather than in repetitive scanning mode. According to still another aspect of the present invention, as will be described, an inertia-less deflector is arranged for life science microscopy, memory repair, or other random access system, to increase throughput by counter moving the beam in controlled relation to sensed settling movements of the mechanical scanning system, to achieve a "stopped" beam despite persisting oscillatory movement of the mechanical system. This decreases the time required for the laser beam to be accurately aimed, effectively increasing throughput.

Use of the techniques of the invention for other purposes will occur and are within the scope of the invention.

Description of Illustrative Embodiments

Figure 7:
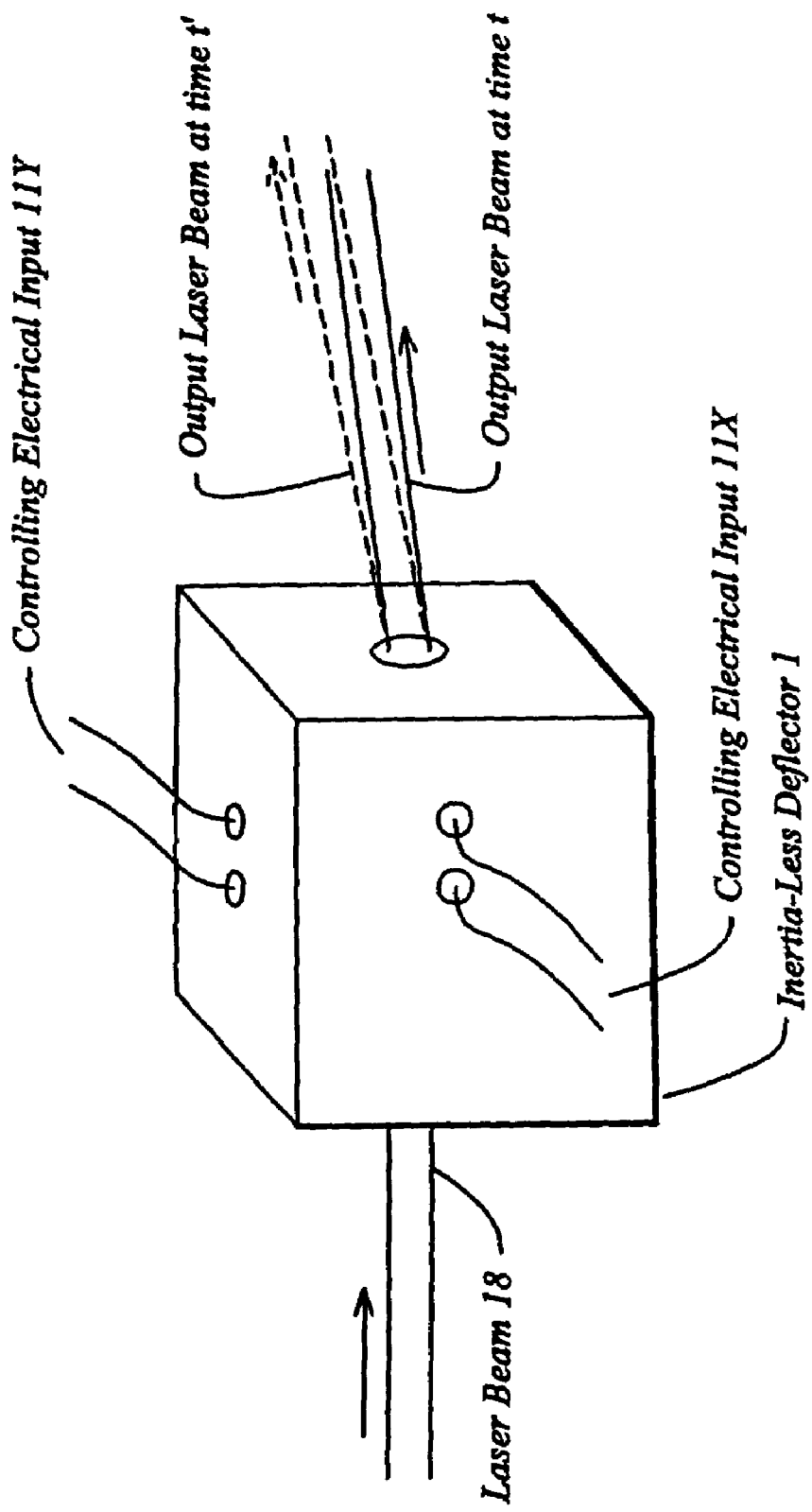
FIG. 7 diagrammatically illustrates an inertia-less deflector, indicating that it causes the direction of the laser beam passing through it to change with time.

With reference to FIG. 7 embodiments of the invention employ a laser beam 18, and an inertia-less deflector 1 which changes the direction of the laser beam by small angles, typically less than 10 milliradians. The deflector is used with a focusing lens which forms a focused laser spot on a workpiece. At selected times, the inertia-less deflector is capable of moving the focused laser spot a few spot diameters in a very short time, typically less than one microsecond. FIG. 7 suggests in exaggerated manner the change in direction the inertia-less deflector imparts to the laser beam by showing different directions of the laser beam at different times t and t'.

In preferred embodiments, the position of the focused laser spot relative to the workpiece is the sum of contributions from the inertia-less deflector and a wide range positioner. The sum can be achieved in a wide range of ways, by using different types of wide range positioners and combining the wide range positioner with the inertia-less deflector in a variety of ways, some of which are illustrated below. The wide range positioner contributes motion that enables the focused laser spot to perform its action over an area typically of several square centimeters.

Figure 8:
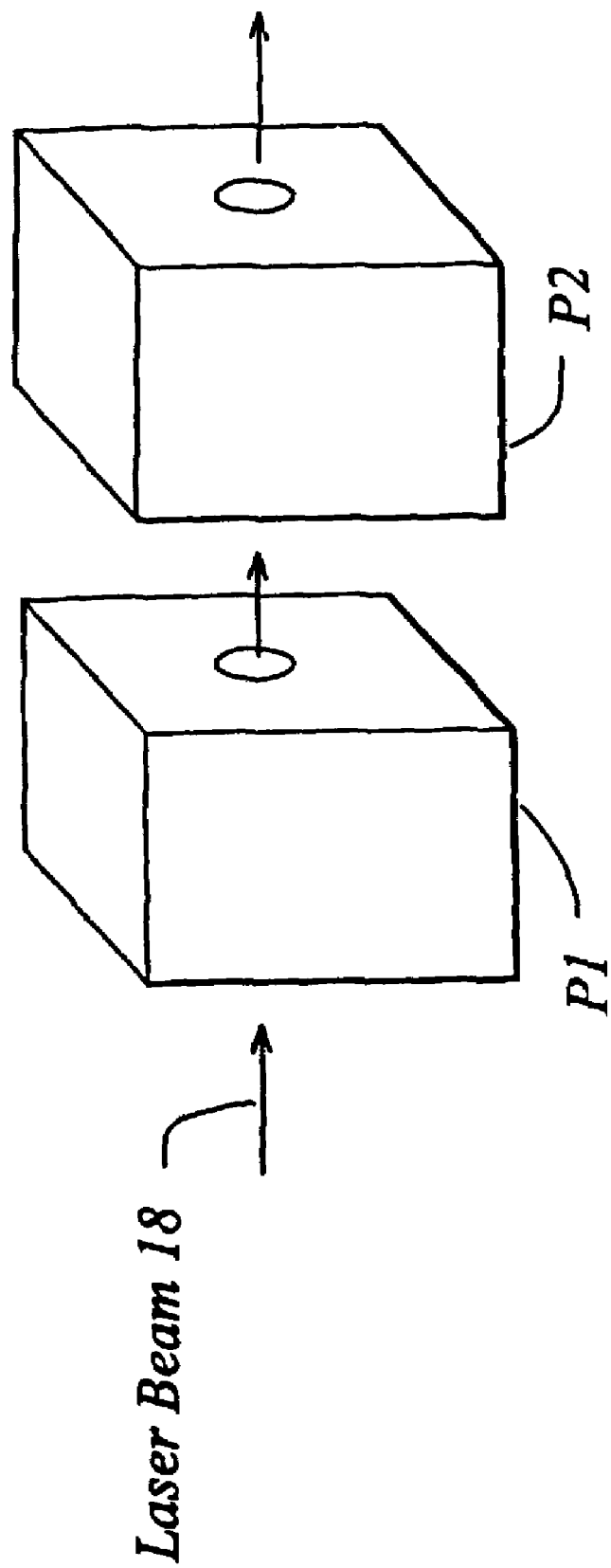
FIG. 8 illustrates two positioners, intending that one be an inertia-less deflector and one a wide range positioner, indicating that the position of the focused laser spot is a sum of contributions from both the inertia-less deflector and the wide range positioner.

FIG. 8 illustrates the summing action of the inertia-less deflector and the wide range positioner which are arranged in sequence. In most cases the inertia-less deflector acts on the laser beam first, in which case P1 indicates the inertia-less deflector while P2 indicates the wide range positioner. In other cases P1 indicates the wide range positioner and P2 indicates the inertia-less deflector.

Typically the wide range positioner moves in a manner that is known or is determined and its position and speed become known to a control system for the inertia-less deflector. The control system causes the focused laser spot to move between successive precise positions on the workpiece and, at each position, remain stationary relative to the workpiece for a time which can be 100 or more times longer than the time spent moving between positions. In embodiments of the invention the wide range positioner does not need to move to precise locations, have high speed, or have its motion depend critically on the position of the workpiece. In many embodiments its motion can be autonomous as in a predetermined, inexpensive raster scan pattern in which it moves at constant speed during each traverse of the pattern. By associating with the wide range positioner, position transducers capable of micrometer or sub-micrometer accuracy, then the method and system enable the inertia-less deflector to ensure that the focused laser spot is positioned with accuracy equal to that of the position transducers.

Figure 9:
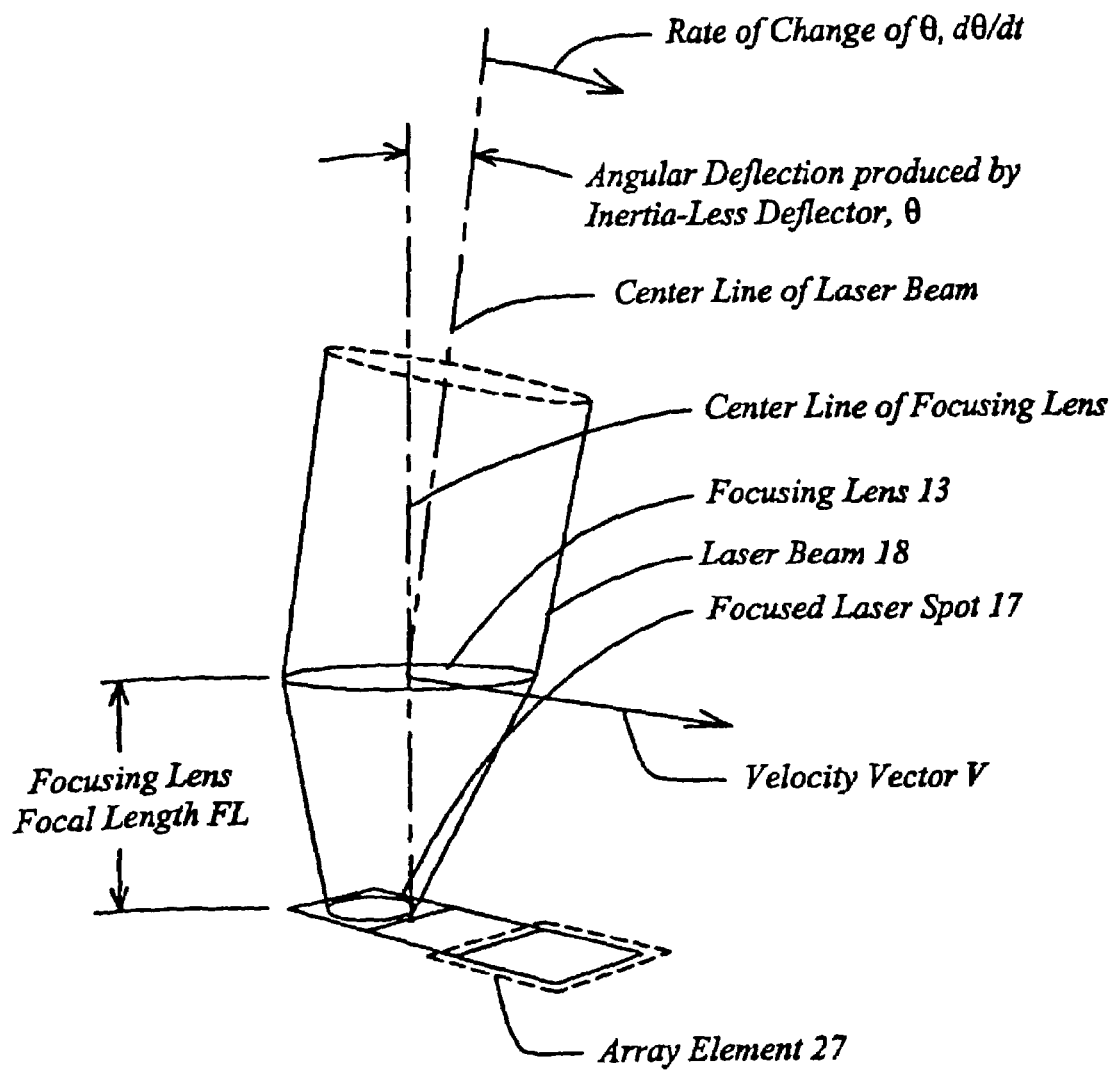
FIG. 9 shows the geometry of a focusing lens, a laser beam, a focused laser spot, and array elements, indicating the contributions of the system of FIG. 8 to the motion of the laser beam and the focused laser spot.

For illustrating the stop, dwell and move actions of a laser spot, FIGS. 10A through 10L show the position of a focusing lens 13 relative to a workpiece, a focused laser spot 17, and the laser beam 18 at twelve progressively increasing times t1 through t12, while FIG. 9 labels certain components and quantities. Though illustrating surface features in general, the positions to which the laser beam is aimed are labeled in FIG. 9 as array elements 27 according to the most important uses of the invention that are contemplated at present.

FIG. 9 shows the velocity V of the focusing lens 13 relative to the workpiece 19. By "relative to the workpiece" is meant that general aspects of the invention apply whether the focusing lens moves and the workpiece is stationary, or the workpiece moves and the focusing lens is stationary, or that both move.

In any case, the velocity V is contributed by the wide range positioner of whichever design.

As indicated elsewhere, the particular combinations disclosed have special advantages and are considered important and novel detailed aspects of the invention.

Figure 10:
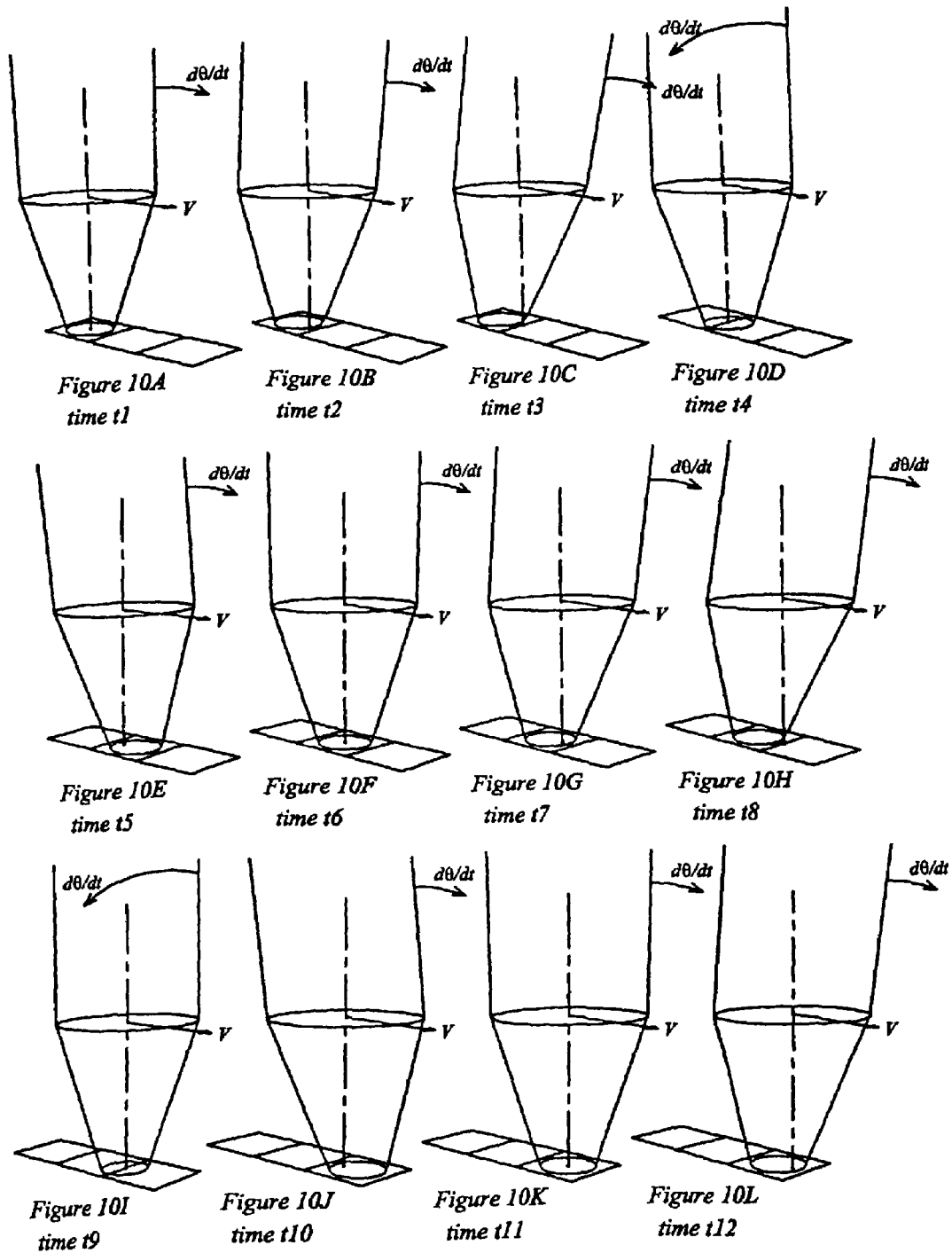
FIGS. 10A through 10L show the features illustrated in FIGS. 8 and 9 at twelve successive times.

Referring to FIGS. 10A through 10C, during times t1, t2, and t3 the focused laser spot is stationary relative to the workpiece and is centered on the first of the three array elements shown. During these times the motion of the focused laser spot contributed by the inertia-less deflector cancels the motion contributed by the wide range positioner. At time t4 the inertia-less deflector suddenly switches the position of the focused laser spot to the center of the second of the three array elements, where it remains centered during times t5 through t8. At time t9 the inertia-less deflector suddenly switches the position of the focused laser spot to the center of the third of the three array elements, where it remains centered during times t10 through t12. This process continues in the X direction while the width of the entire array is traversed. Then the wide range positioner moves approximately the height of an array element in the Y direction of the array and another scan across the array occurs. In most, but not all, wide range positioners the wide range positioner reverses its direction of X motion at the same time that it increments its position in Y. This process continues until the entire Y dimension of the array is traversed.

Figure 11:
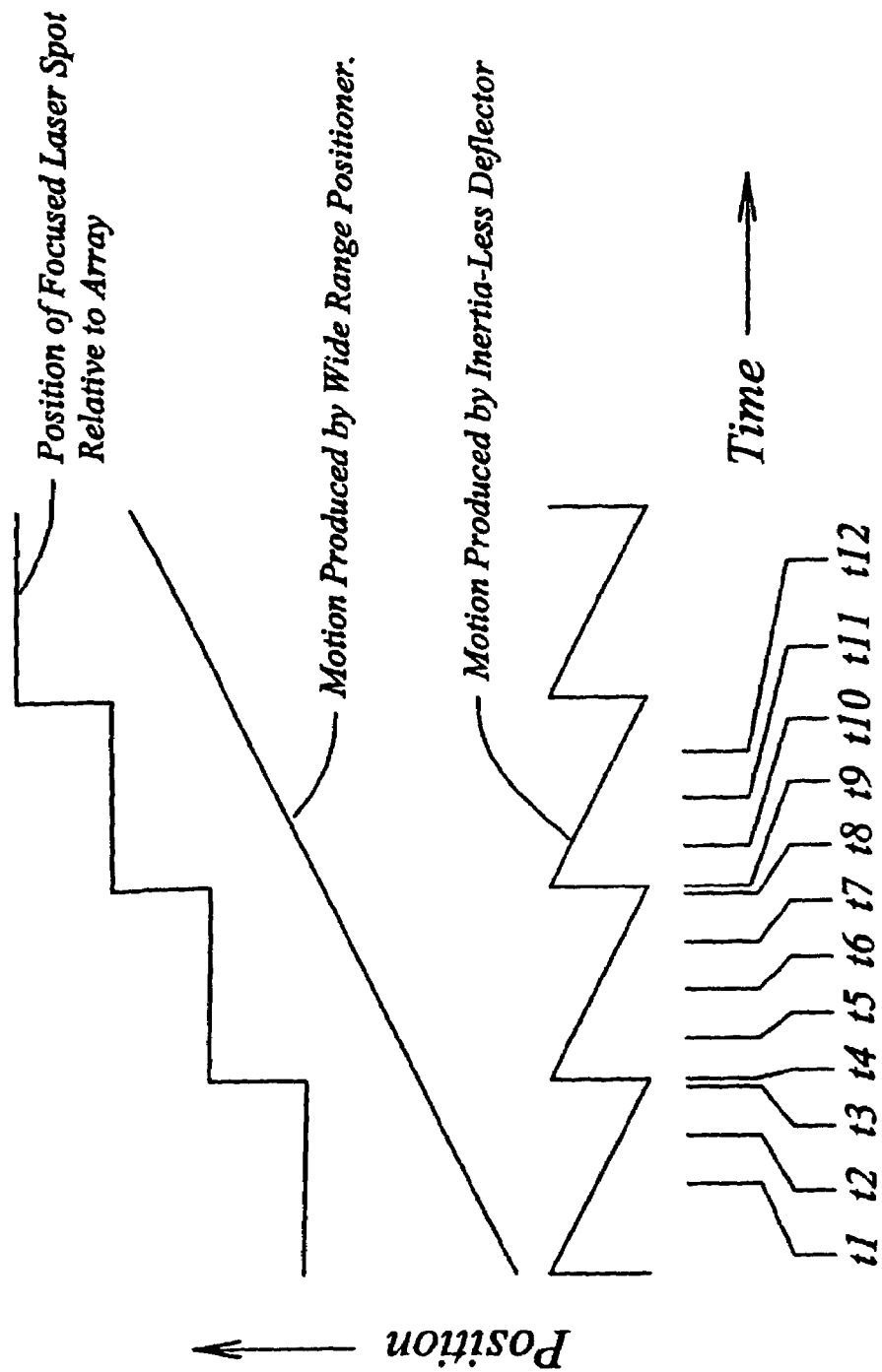
FIG. 11 shows the motion shown in FIGS. 10A through 10L in the form of graphs of position versus time.

FIG. 11 illustrates the same motion as shown in FIGS. 10A through 10L, but in the form of graphs of position versus time. FIG. 11 shows the motion of the focused laser spot due to the wide range positioner alone, in the case illustrated, a straight line with approximately constant speed, the inertia-less deflector alone, a sawtooth, and the position of the laser spot resulting from the action of both the wide range positioner and the inertia-less deflector, a stair step, the spot being stationary and effective over a large preponderance of the total time elapsed. The times indicated in FIG. 10A through 10L are also indicated in FIG. 11.

FIG. 9 shows that the inertia-less deflector makes its contribution by rotating the laser beam by an angle θ relative to the axis of the lens that forms the focused laser spot, in this case focusing lens 13. Lens 13, for instance, is a low mass scan lens of a flying lens scanner, the larger scan lens of a galvanometer scanner, or a microscope objective if the scanner design is such that the focusing lens is stationary or is subjected to limited acceleration. Furthermore the optical design ensures that the laser beam rotates about the lens, with its position on the lens remaining constant as it rotates. In the case illustrated, the velocity VD of the focused laser spot contributed by the inertia-less deflector is equal to the focal length of the focusing lens FL times the rate of change of θ, dθ/dt. A typical focal length is 4 millimeters, and a typical wide range positioner velocity is 100 centimeters per second. The velocity contributed by the inertia-less deflector is minus the velocity of the wide range positioner for a typical time of 200 microseconds, and then is greater than typically 20 meters per second in the opposite direction during the short time in which the position of the focused laser spot switches from one array element to the next.

For the application being illustrated, the velocity of the wide range positioner V is approximately constant in the sense that its change in a time t6–t1, the time per array element, is two or more orders of magnitude smaller than the peak value of VD.

Figure 12:
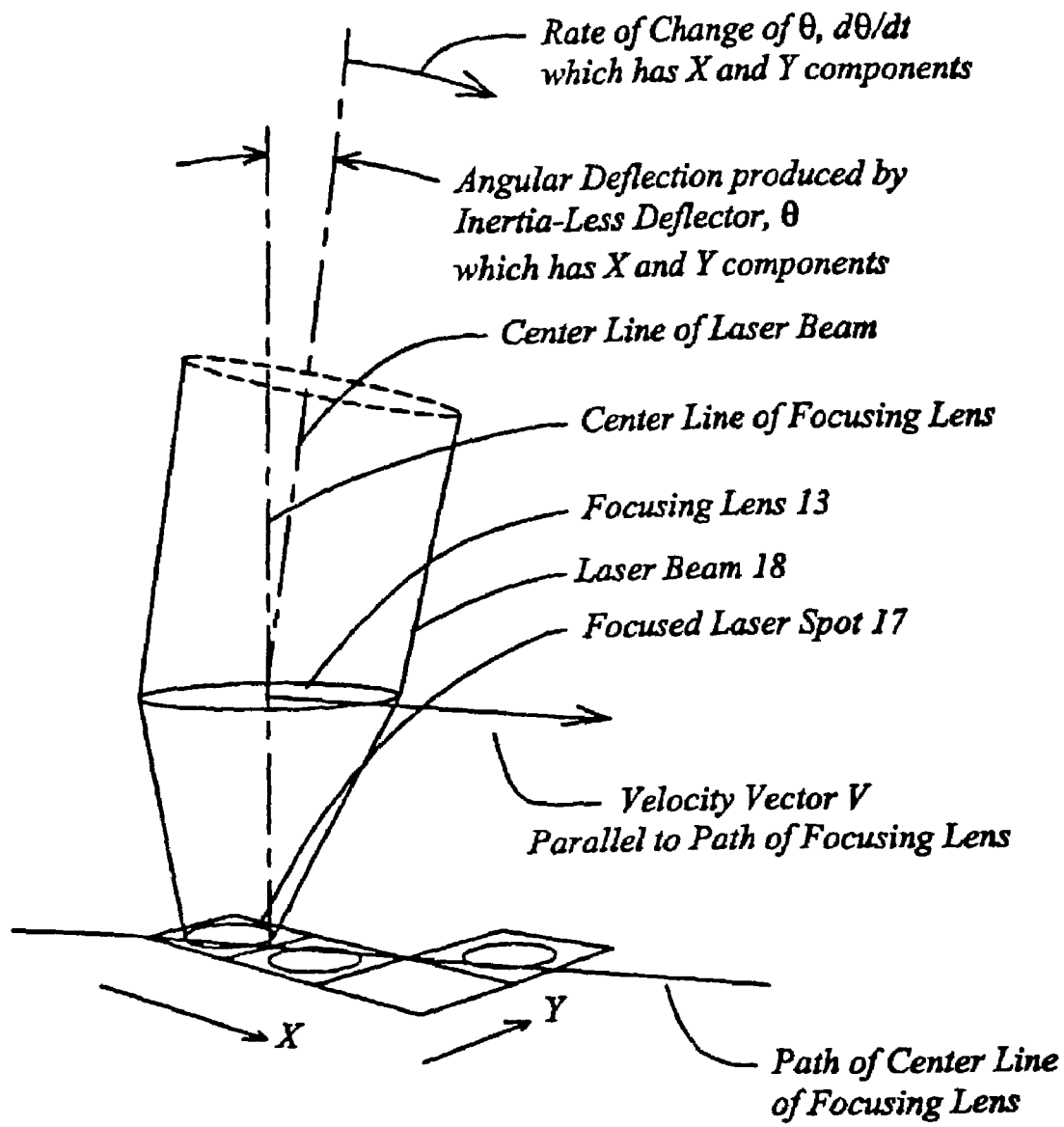
FIG. 12 shows the geometry of FIG. 9 generalized to the case that the wide range positioner has velocity components in both X and Y directions.
Figure 13:
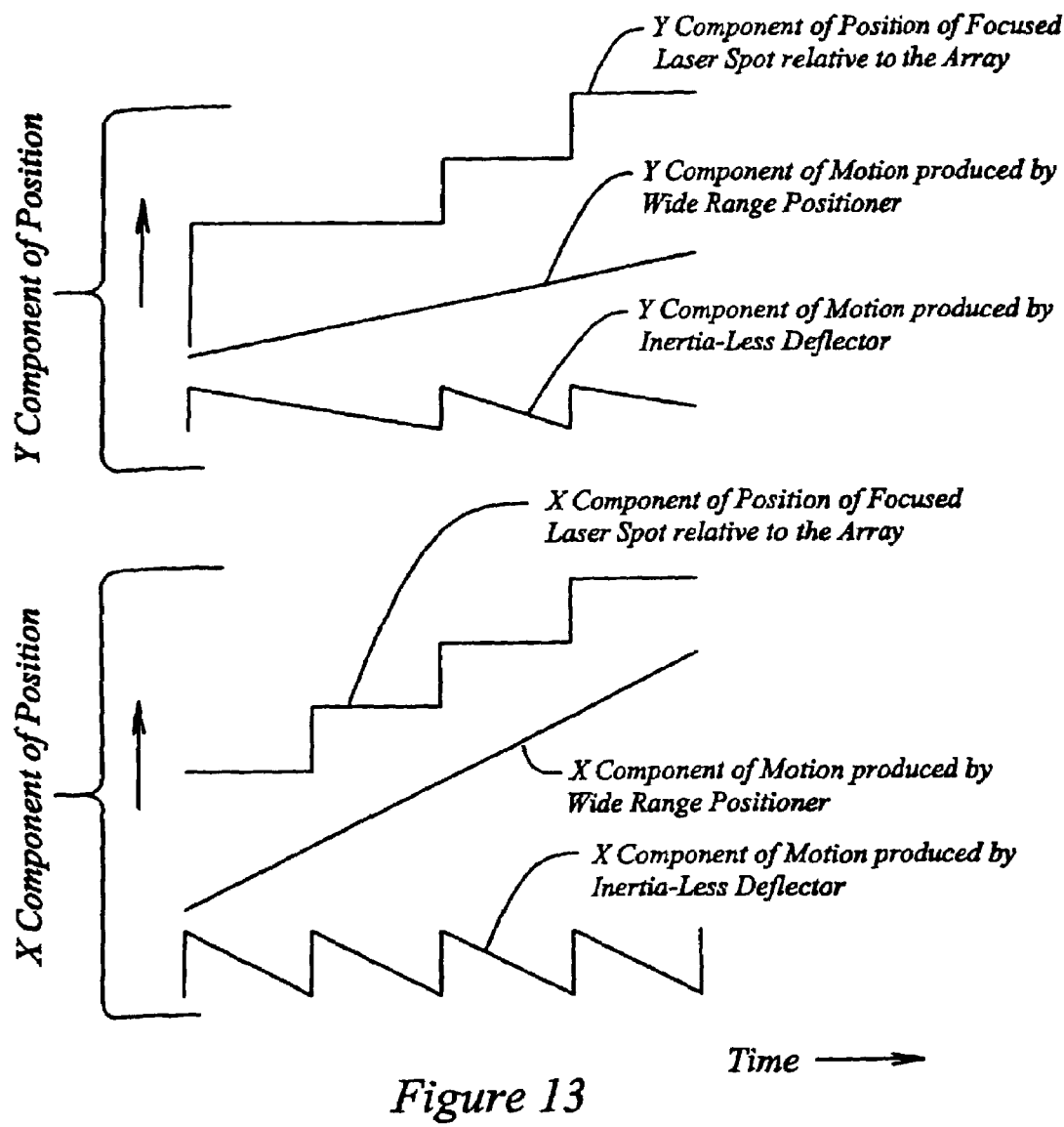
FIG. 13 shows the motion shown in FIG. 12 in the form of graphs of components of position versus time.

FIGS. 9, 10A through 10L, and 11, for simplicity of exposition, show motion in only one dimension, such as would occur in the case that the array elements have perfect geometry and are aligned perfectly relative to the axis of a one dimensional inertia-less deflector and one axis of a wide range positioner. It is preferred generally, however, that the inertia-less deflector have two (or perhaps more) axes and a more general case is illustrated in FIGS. 12 and 13. In FIGS. 12 and 13 X and Y components of motion relative to the workpiece are shown. FIG. 13 also shows that while the inertia-less deflector's motion in X, the faster of the two motions shown, appears regular, the motion in the perpendicular direction is typically not so regular, with the angle θ and its rate of change dθ/dt changing from one array element to the next.

An example of hardware and software for implementing the above described motion will be described later, as will other modes of operation which provide advantages over existing equipment.

FIG. 7 shows that the inertia-less deflector has controlling electrical inputs 11X and 11Y for the most common case, in which the inertia-less deflector has two orthogonal axes, X and Y.

In the usually preferred case, associated with the wide range positioner are position transducer outputs, referred to later as 12X and 12Y. Position transducer outputs are typically employed in array scanners. The array elements 27 are typically only a few tens of micrometers wide and accurate knowledge of the wide range positioner's position within a few micrometers to a few tenths of micrometers is desired.

Excitation of Fluorescence from Biochemical Arrays

Figure 4A:
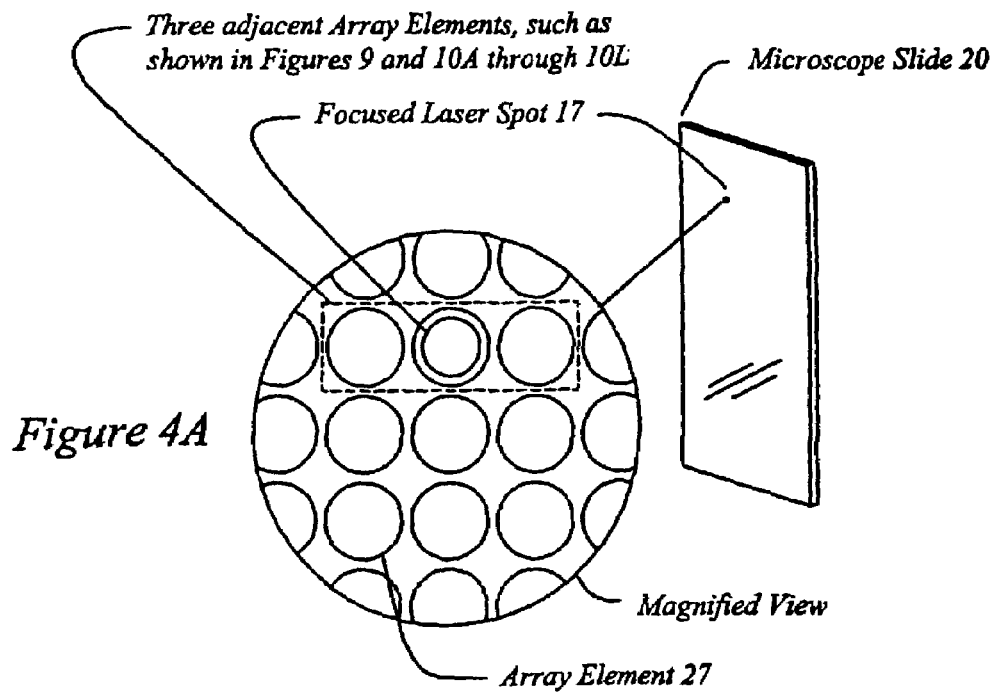
FIGS. 4A and 4B respectively show spotted arrays and photolithographic arrays, particular examples of micro-arrays of biochemical material.
Figure 4B:
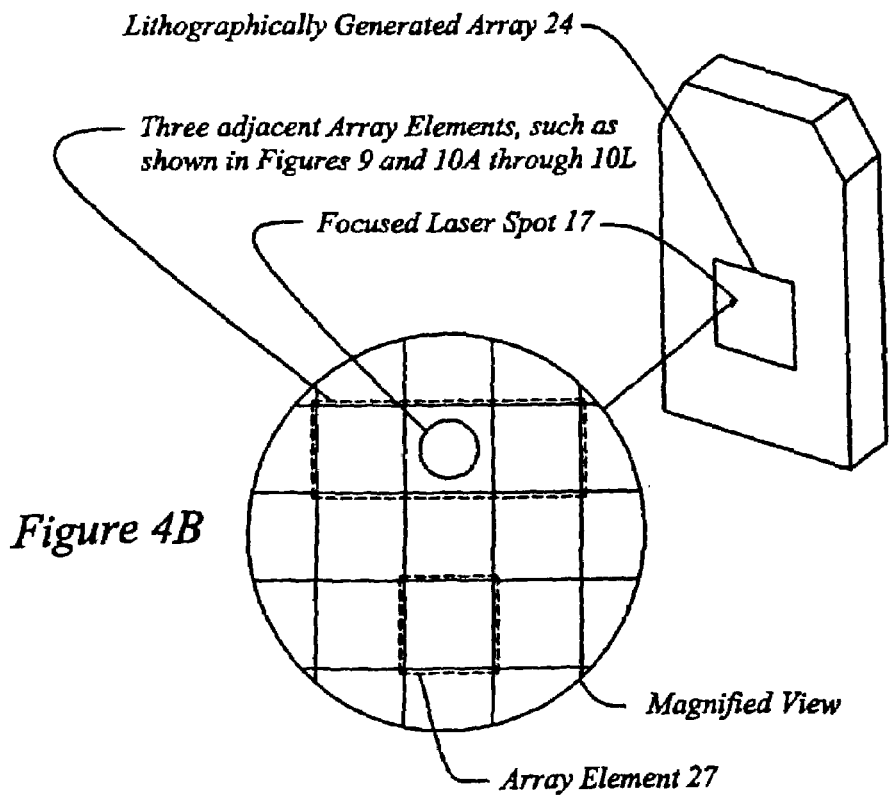

As has been explained, an important and novel broad aspect of the invention is the excitation of fluorescence from biochemical arrays, and the efficient detection of fluorescence from each element of an array in succession. In general, the invention applies to all kinds of biochemical arrays, including those having at least 400 features per square centimeter, and those having at least 1000 features per square centimeter. The invention is particularly applicable to far higher densities. Such arrays are illustrated in FIGS. 4A and 4B. In FIG. 4A the array elements 27 are approximately circular and are members of a spotted array, which has been deposited on the surface of a workpiece 19, here a microscope slide 20. Diameters of such array elements range from 50 to 500 micrometers, with the pitch between array elements being between about one and two times the diameter of each array element, leading to array densities between about 100 and 100,000 per square centimeter.

In FIG. 4B the array elements are rectangular and are generated photolithographically, rather than by depositing droplets of liquid as is the case for spotted arrays. The array is shown attached to a cartridge such as is used in the GeneChip® manufactured by Affymetrix Inc. For these arrays the X and Y dimensions of each element range between 10 and 50 micrometers and the x and y pitches between array elements are equal to their X and Y dimensions, leading to array densities between about 40,000 and 1,000,000 per square centimeter. The high positioning accuracy provided by this invention makes it possible to position the focus laser spot accurately in the center of any of these elements.

In the case of photolithographically generated arrays the border region between adjacent elements often exhibits much brighter fluorescence than does the center of either element. The invention, by aiming the focused laser spot at the centers of array elements, avoids the measurement errors and wasted time associated with collecting light from the border regions.

Figure 5A:
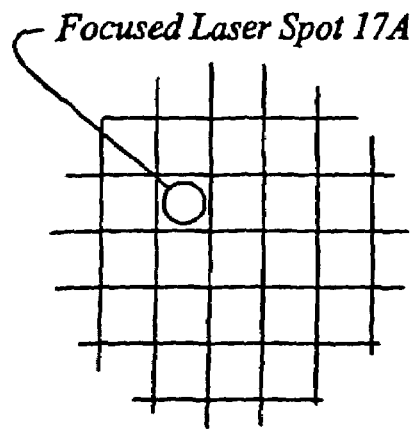
FIGS. 5A through 5F show different array geometries to which the invention is applicable.
Figure 5B:
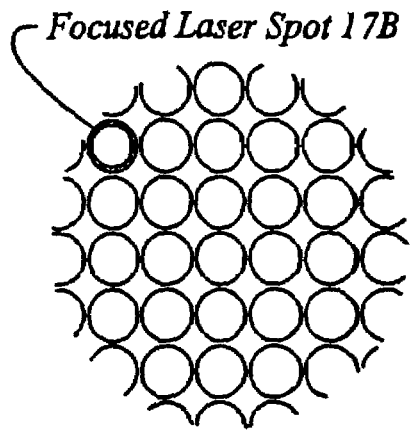
Figure 5C:
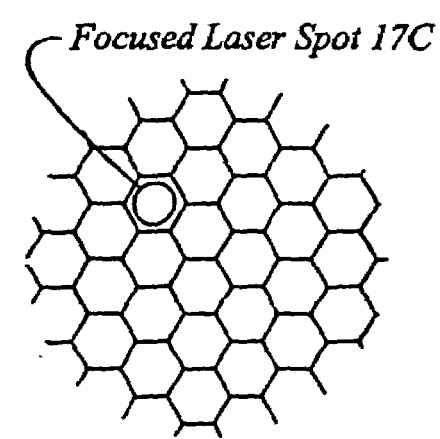
Figure 5D:
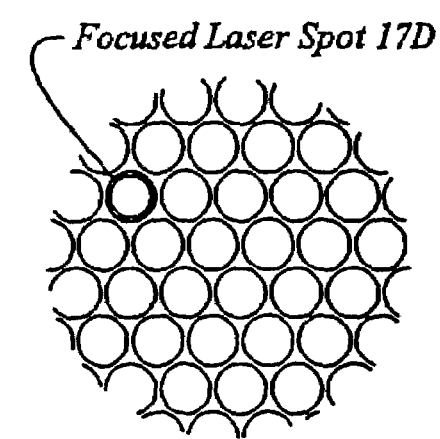

FIGS. 5A through 5F, a series of different arrays, illustrate that a wide range of arrays can be scanned. In each of FIGS. 5A through 5F a typical position and relative size for the focused laser spot 17 is shown. FIG. 5A shows a perfectly regular photolithographically generated array described above and FIG. 5B shows a spotted array with perfect spacing between the array elements. FIGS. 5C and 5D are similar to 5A and 5B, but show hexagonal close packed arrangements of the array elements rather than a rectangular arrangement.

Figure 5E:
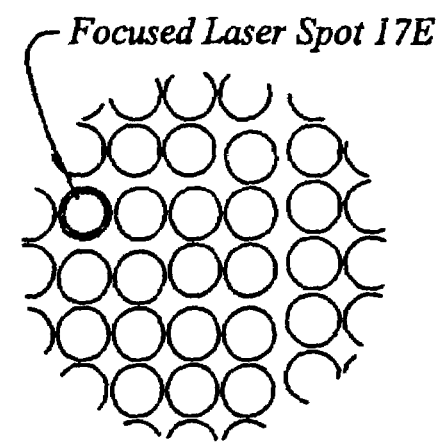
Figure 5F:
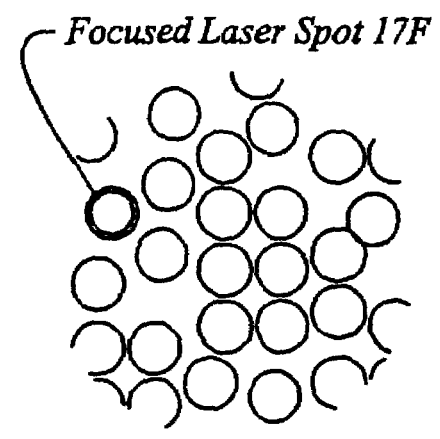

FIG. 5E shows a spotted array in which there are errors in the location of the array elements typical of those errors found in practice. FIG. 5F shows a "random array", such as would be encountered when the array elements are the ends of optical fibers or are fluorescent beads.

According to another aspect of the invention a second mode of operation, referred to as "acquisition mode", enables the same scanner to handle the cases shown in FIGS. 5E and 5F as well as it handles the cases of perfect geometry shown in FIGS. 5A through 5D.

Acquisition mode consists of scanning the array at higher speed and higher spatial resolution than that used when making accurate fluorescence measurements. Either reflected laser light or fluorescent light (or both) from the array elements is measured as a function of position indicated by the position transducer outputs of the wide range positioner. Not only are the positions of array elements measured, but also the positions of fiducial marks, if present, are measured as well. The Affymetrix GeneChip®, for example, contains fiducial marks in two forms: a reflective chrome border surrounding the array and especially bright array elements on the periphery of the array. In acquisition mode the inertia-less deflector may either be kept at a constant deflection, and not enter into the operation, or it may be moved rapidly to scan the spot around the edges of the features or fiducial marks in order to locate them better. A provision for varying the size of the focused laser spot, which can facilitate the acquisition mode is described later.

Details of a preferred overall system for detecting fluorescence by the "stop and dwell" technique will now be described with reference to FIG. 15.

When collecting fluorescent light from a thin layer of fluorescent material, such as occurs in biochemical arrays, the signal to noise ratio is enhanced by rejecting spurious light from above or below the plane containing the fluorescent material of interest. A confocal microscope, invented by Minsky, rejects such spurious light. The fluorescence detector 32, shown in FIG. 15, in combination with the focusing lens 13, implements a confocal microscope 35, by means of a tube lens 36, and a pinhole 37. Following the pinhole is a photodetector such as a photomultiplier 38.

The focusing lens and the tube lens combine to form an image 64 of the focused laser spot in the plane of the pinhole. In many confocal microscopes of the past the pinhole's diameter has been made only slightly larger than the image of the focused laser spot. However with embodiments of the present invention the inertia-less deflector would cause the image to move away from the center of such a pinhole and to change the fraction of the light that would pass through the pinhole whose diameter is only slightly larger than the image of the focused laser spot. The use of the inertia-less deflector in the manner presented here therefore might seem to conflict with the use of a confocal microscope.

I recognize, however, that the optimum pinhole diameter is not equal to slightly more than the diameter of the image of the focused spot but is approximately ten times larger, and that a range of five spot diameter's worth of motion of the image for instance can be provided within the pinhole with negligible decrease in light transmission through the pinhole. I note that the amount of background light originating above or below the focal plane of the focusing lens and allowed to pass through this larger pinhole is small, while in fact significant other benefits are achieved. The larger pinhole allows for the workpiece to be slightly out of focus and not to be perfectly flat. The larger pinhole also allows one to use very light-weight scan lenses such as molded aspheric lenses which are not color corrected. The larger pinhole still limits collection of spurious light to that coming from approximately 50 micrometers above the focal plane of the focusing lens to 50 micrometers below the focal plane. This range of heights is much smaller than the range from which a non-confocal system accepts light. The confocal microscope with a larger pinhole provides approximately the same advantage over a non-confocal system as does a confocal microscope with a smaller pinhole, while accommodating the movements of the laser beam according to the invention.

Figure 15:
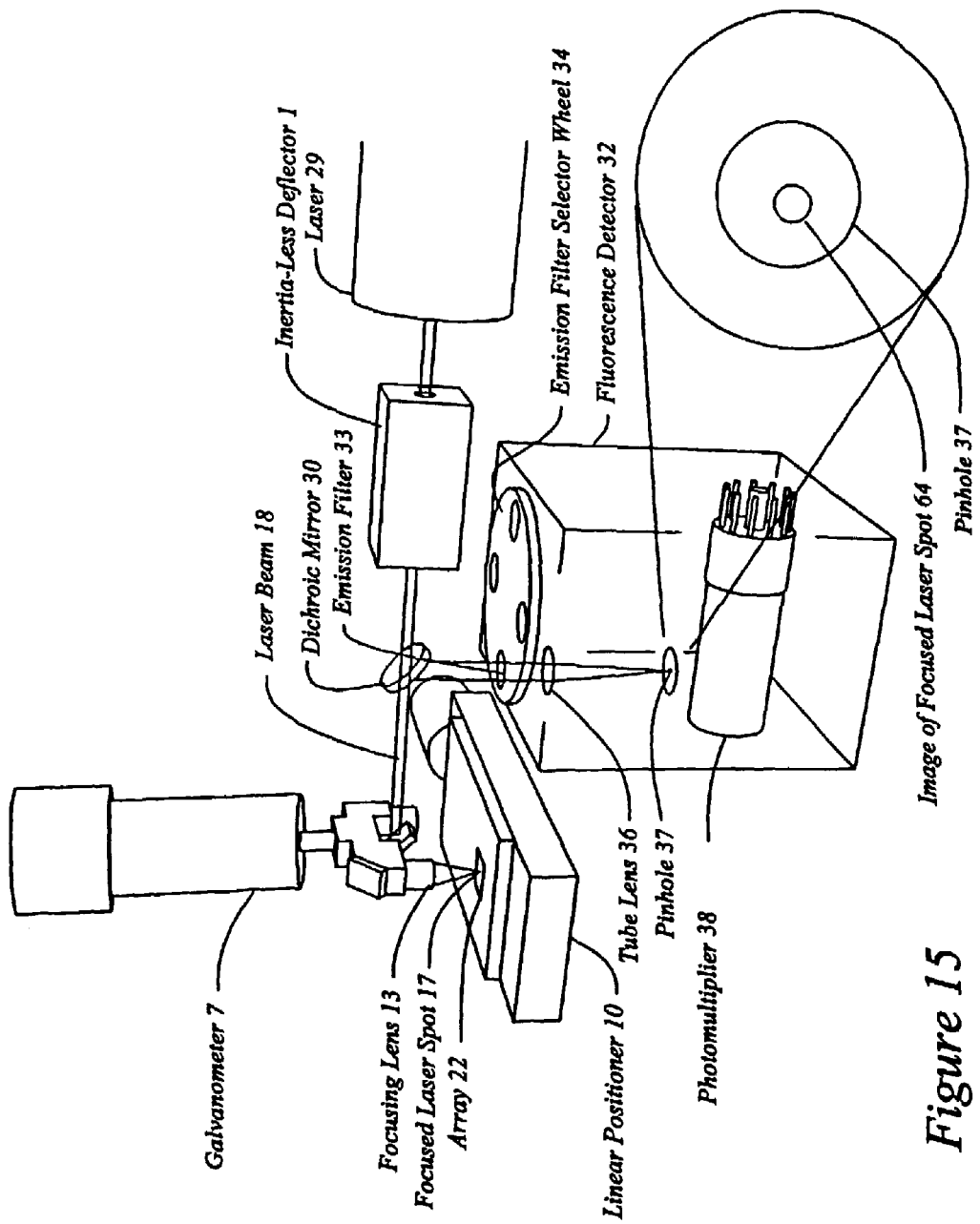
FIG. 15 shows a preferred embodiment of the invention which overcomes limits posed by fluorophore saturation when detecting fluorescence, and by a blow-up shows the image of the focused laser spot moving within the pinhole of confocal optics of the embodiment.

In addition to the confocal microscope components, FIG. 15 shows the laser 29 which provides the laser beam 18, an emission filter 33, which passes fluorescent light and rejects laser light, and an emission filter selector wheel 34 in which the emission filter is mounted. The emission filter selector wheel allows for the selection of several different emission filters and allows for selection of filters which pass reflected laser light rather than fluorescent light.

The tube lens 36 typically has a focal length between 50 and 75 millimeters, and the pinhole 37 a diameter between about 0.5 and 2 millimeters.

Preceding the fluorescence detector is a dichroic mirror 30 which passes laser light and reflects fluorescent light coming from the array so that the fluorescent light goes into the fluorescence detector.

Not shown in the figures are conventional components such as a computer, an operator terminal, a mechanical handler and focusing mechanism for the workpiece, power supplies, data collection electronics, and electronics for the wide range positioner. A preferred embodiment of electronics for driving a pair of acousto-optic deflector modules is described later.

Examples of Inertia-Less Deflectors and Embodiments Employing Them

The inertia-less deflector may for instance be an acousto-optic deflector, described generally in the book Design and Fabrication of Acousto Optic Devices, edited by A. P. Goutoulis, et al. (Marcel Dekker, New York, 1994) or an electro-optic deflector, described generally in section 9.7 of Introduction to Optical Electronics, by Amnon Yariv (Holt, Rinehart and Winston, New York 1976.)

In most applications of acousto-optic deflectors it is important that the acousto-optic deflector be able to operate over a range of ten to 100 or more spot diameters. Electro-optic deflectors, being incapable of such a large range, are seldom considered. For important aspects of the present invention however I recognize that a range of only two or three spot diameters is adequate, and that electro-optic deflectors can be used to implement the present invention. Electro-optic deflectors are simpler than acousto-optic deflectors. Because of present cost and availability considerations, however the presently most preferred embodiments of the inertia-less deflector, shown in FIGS. 15 and 16, comprises two acousto-optic deflector modules 4, one for the X axis and one for the Y axis.

Preferred embodiments of the invention employ many different wide range positioners. FIGS. 14A through 14I show respectively different wide range positioners in conjunction with an inertia-less deflector, a focusing lens and a workpiece.

Figure 14A:
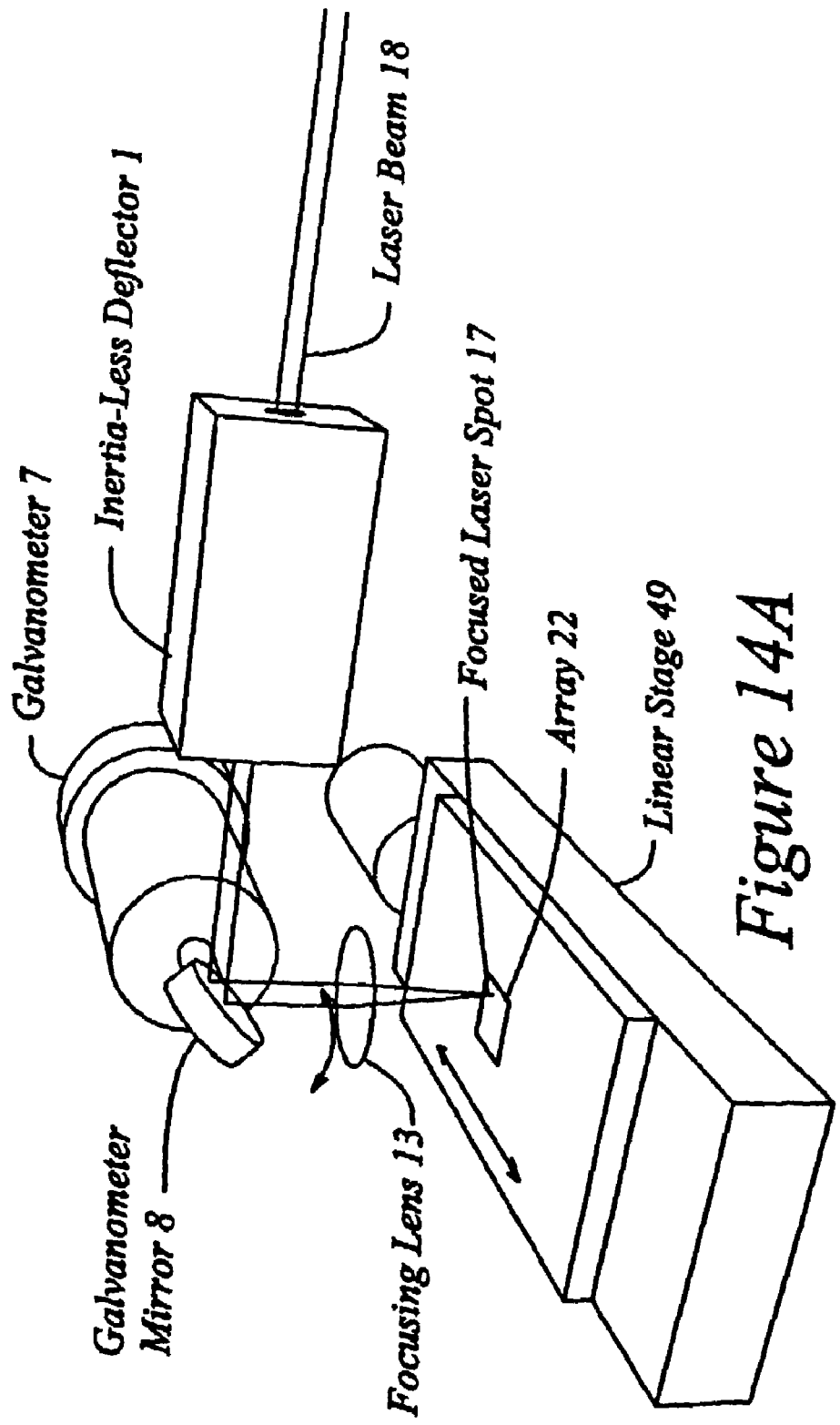
FIGS. 14A through 14I show respectively different wide range positioners in conjunction with an inertia-less deflector, a focusing lens, and a workpiece.

In FIG. 14A the wide range positioner is a combination of a single axis galvanometer scanner 7 which moves the focused laser spot rapidly in the X direction and a linear stage which moves the workpiece slowly in the Y direction. This architecture (of the wide range positioner) is used, for example, in array scanners manufactured by Agilent Corporation.

Figure 14B:
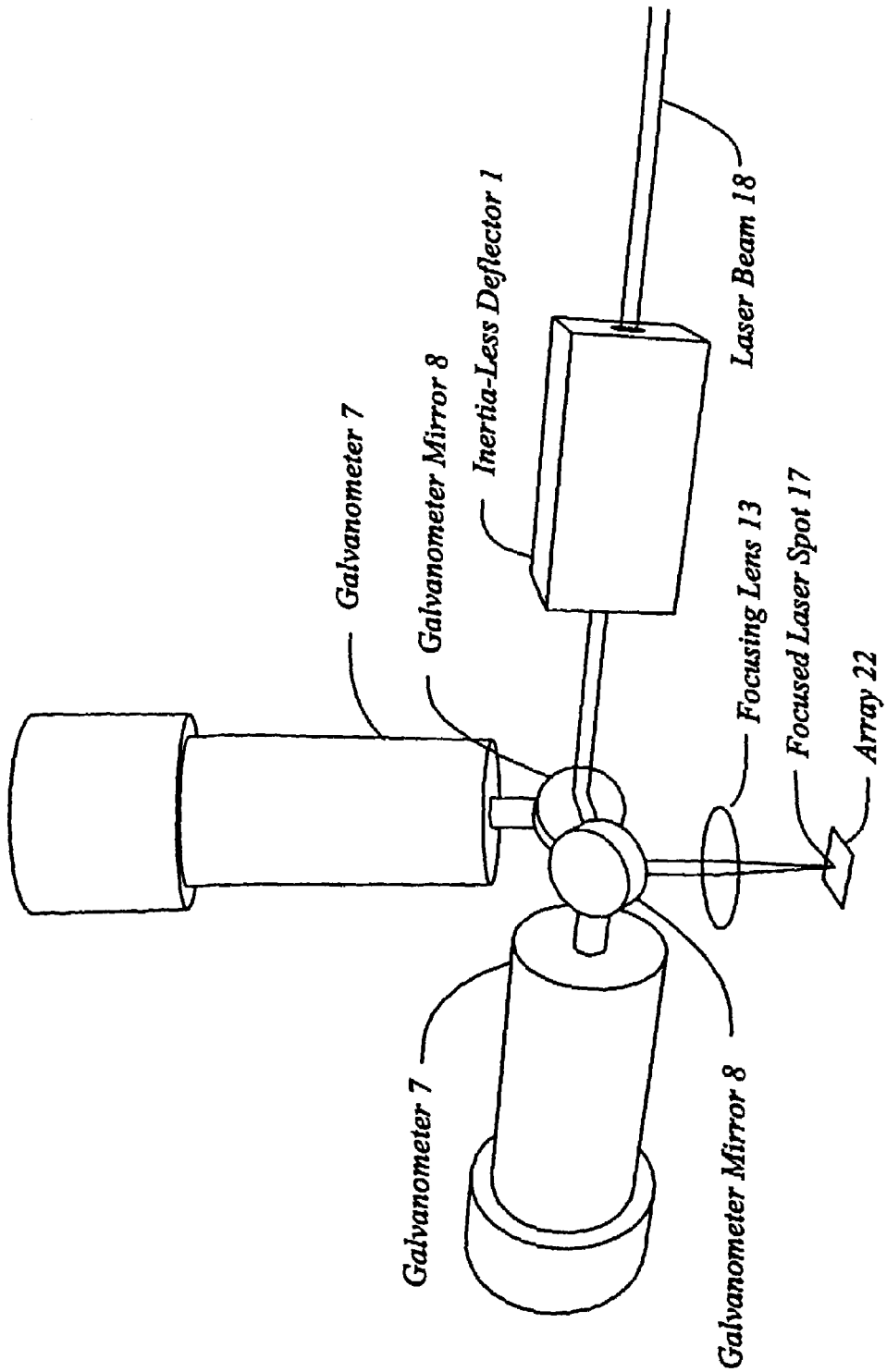

In FIG. 14B the wide range positioner is a two axis galvanometer scanner, two galvanometers being orthogonally arranged.

Figure 14C:
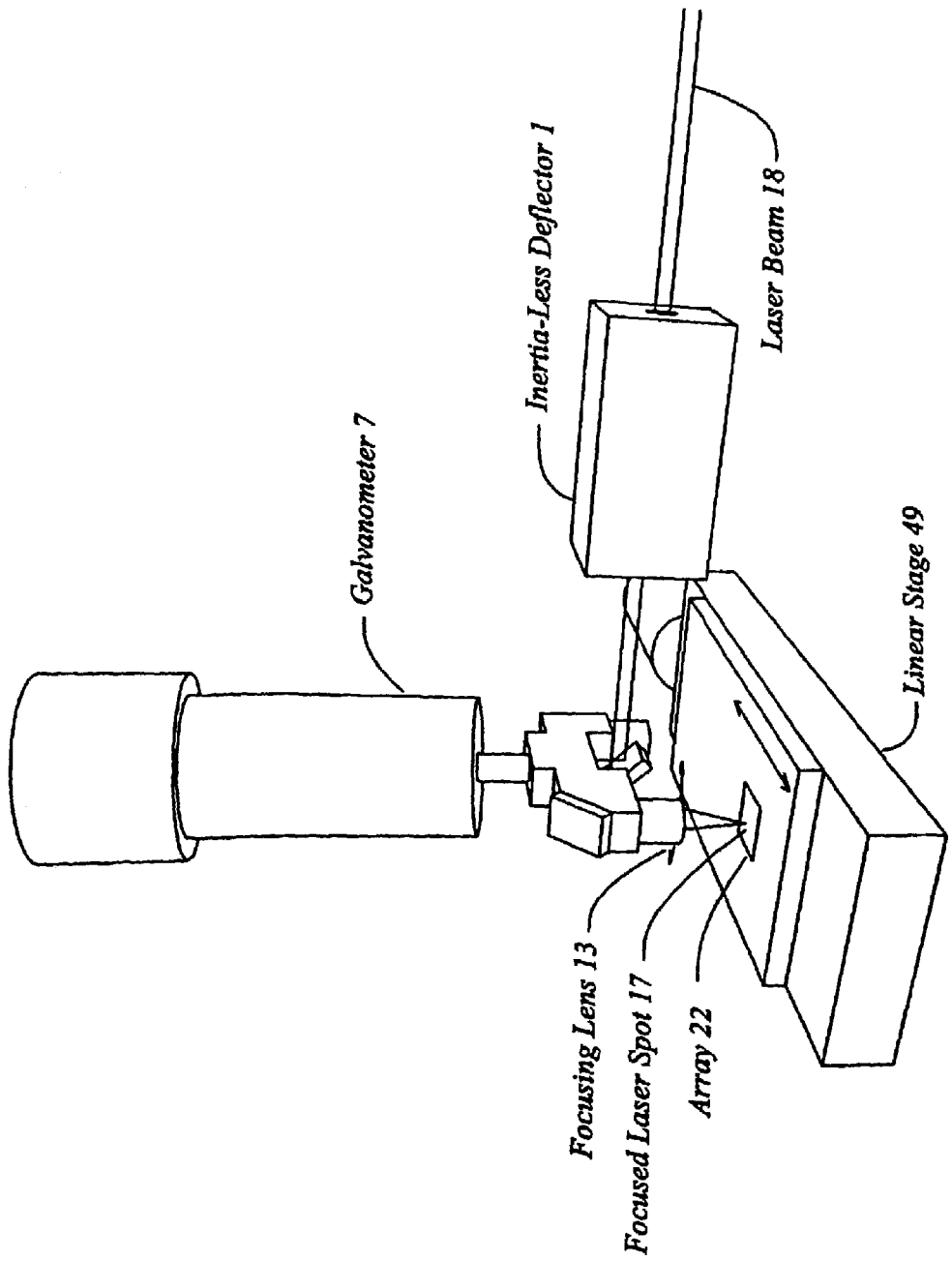

In FIG. 14C the wide range positioner is a flying lens scanner 9, in which a galvanometer moves a very small lens and the focused laser spot rapidly back and forth in an arc while a linear stage 49 moves a workpiece slowly in the Y direction as in FIG. 14A. This architecture is used in array scanners manufactured by Affymetrix, Inc. and is described in my U.S. Pat. Nos. 6,185,030 and 6,201,639, the entire disclosures of which are hereby incorporated by reference as if fully set forth.

Figure 14D:
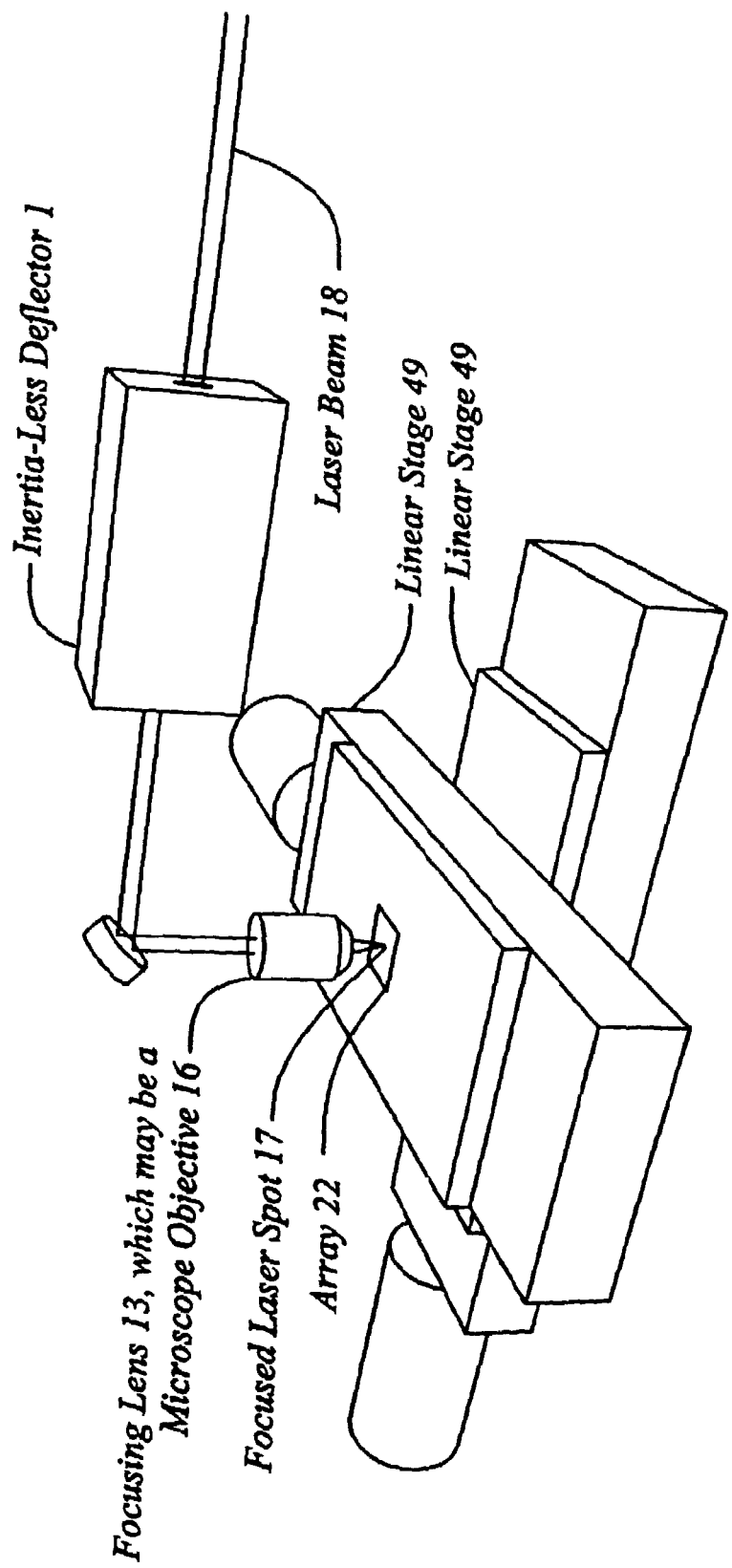

In FIG. 14D the wide range positioner is a two axis linear positioner comprising linear stages 49 which move the workpiece respectively in X and Y directions while the focusing lens remains stationary, with acceleration less then 5 Gs. In this case the focusing lens can advantageously be a commercial microscope objective 16 and the illustration in FIG. 8 of the laser beam passing through both the wide range positioner and the inertia-less deflector does not apply. The relative motion of the focused laser spot and the workpiece is still the sum of contributions from both the wide range positioner and the inertia-less deflector as shown in FIGS. 9, 10A through 10L, 11, 12, and 13. This architecture is used, for example, in array scanners manufactured by Perkin-Elmer Corporation.

Figure 14E:
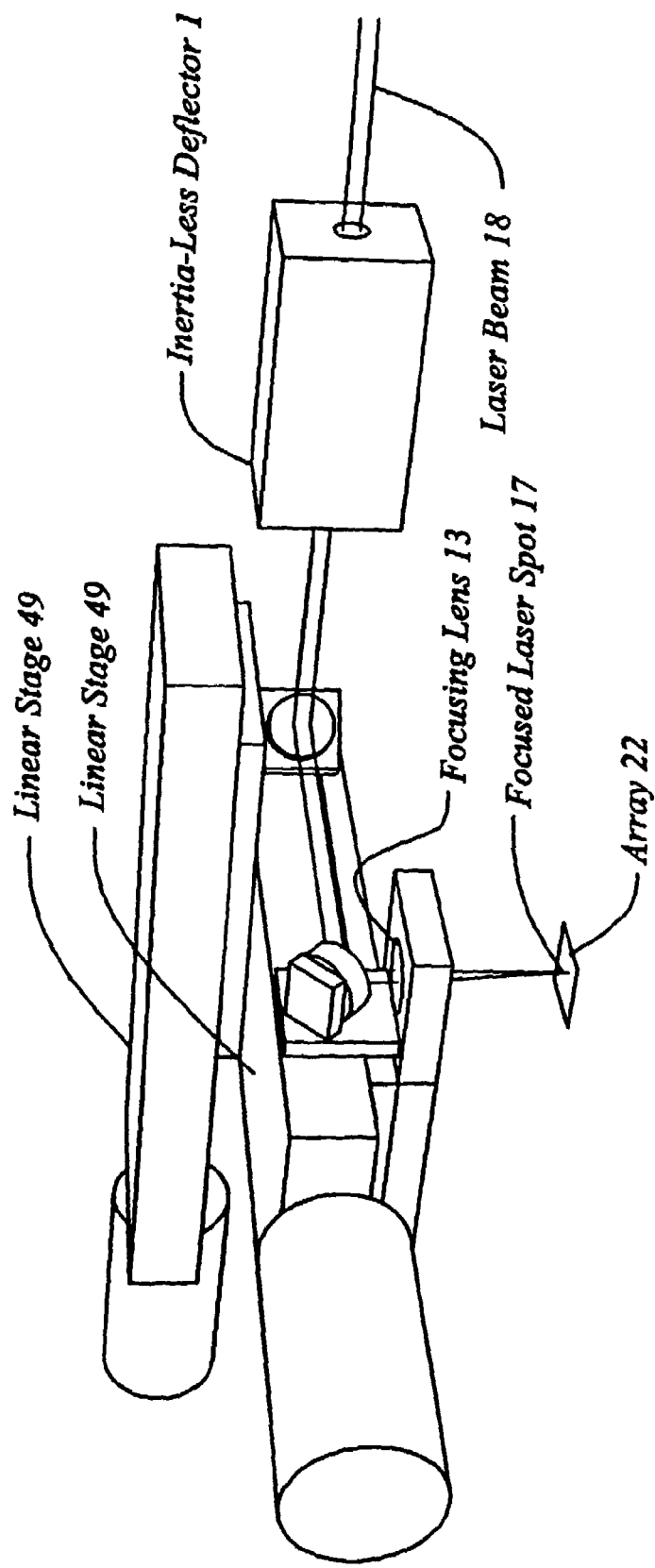

In FIG. 14E the wide range positioner is a two axis linear positioner comprising two linear stages 49 which move the focusing lens respectively in X and Y directions while the workpiece remains stationary. The inertia-less deflector and the laser may either be moved on the positioner or be stationary. In the stationary case a moving mirror which provides a 90 degree change in laser beam direction is provided. As in FIG. 14D the focusing lens may be a commercial microscope objective. Depending upon the arrangement selected, this case is one in which the wide range positioner may act on the laser beam prior to the inertia-less deflector.

Figure 14F:
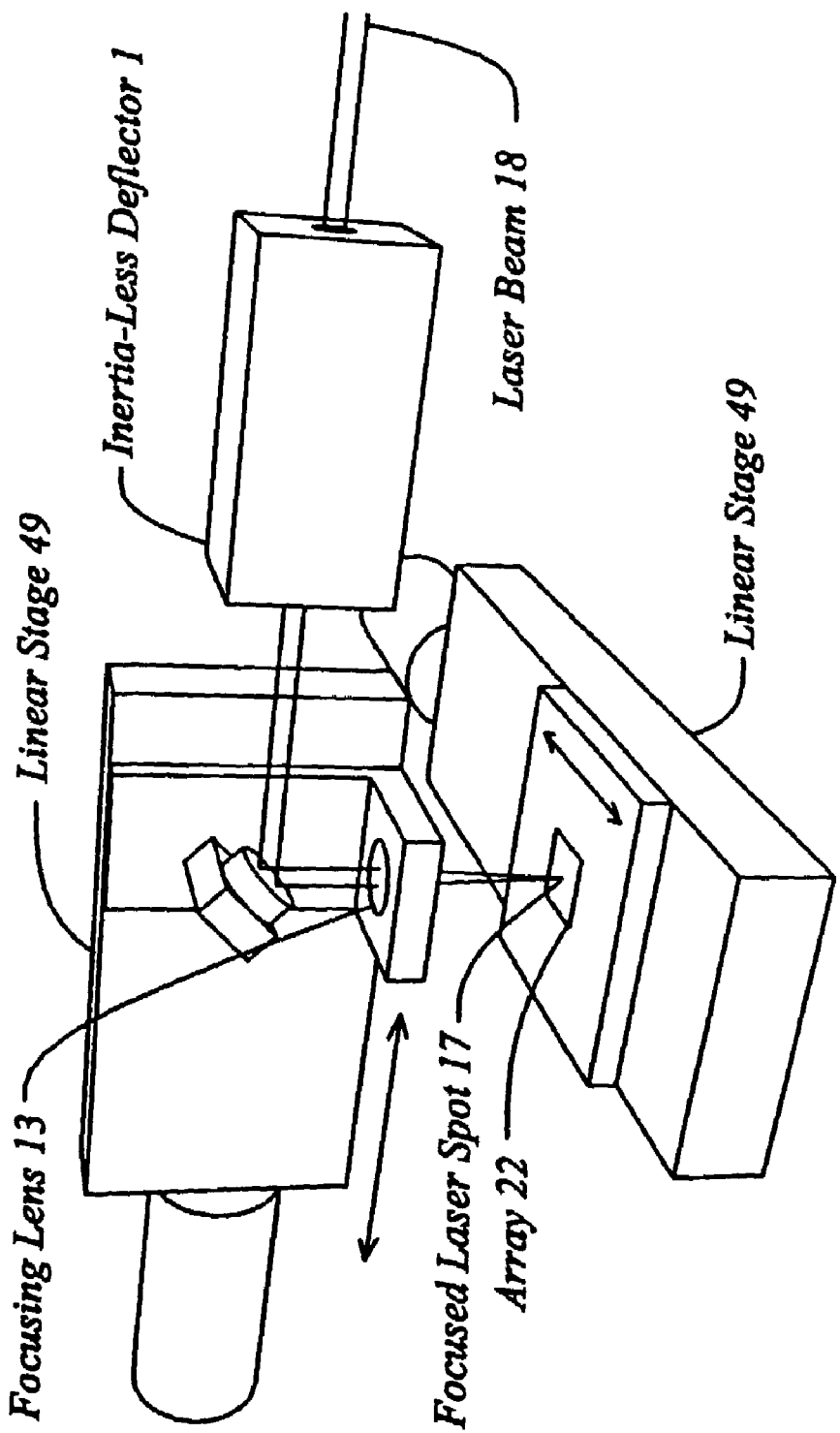

In FIG. 14F the wide range positioner is a two axis linear positioner which moves the workpiece in the X direction and the focusing lens in the Y direction. The laser and inertia-less deflector may either move or be stationary, as in FIG. 14E, but no mirror for changing laser beam direction by 90 degrees is needed.

Figure 14G:
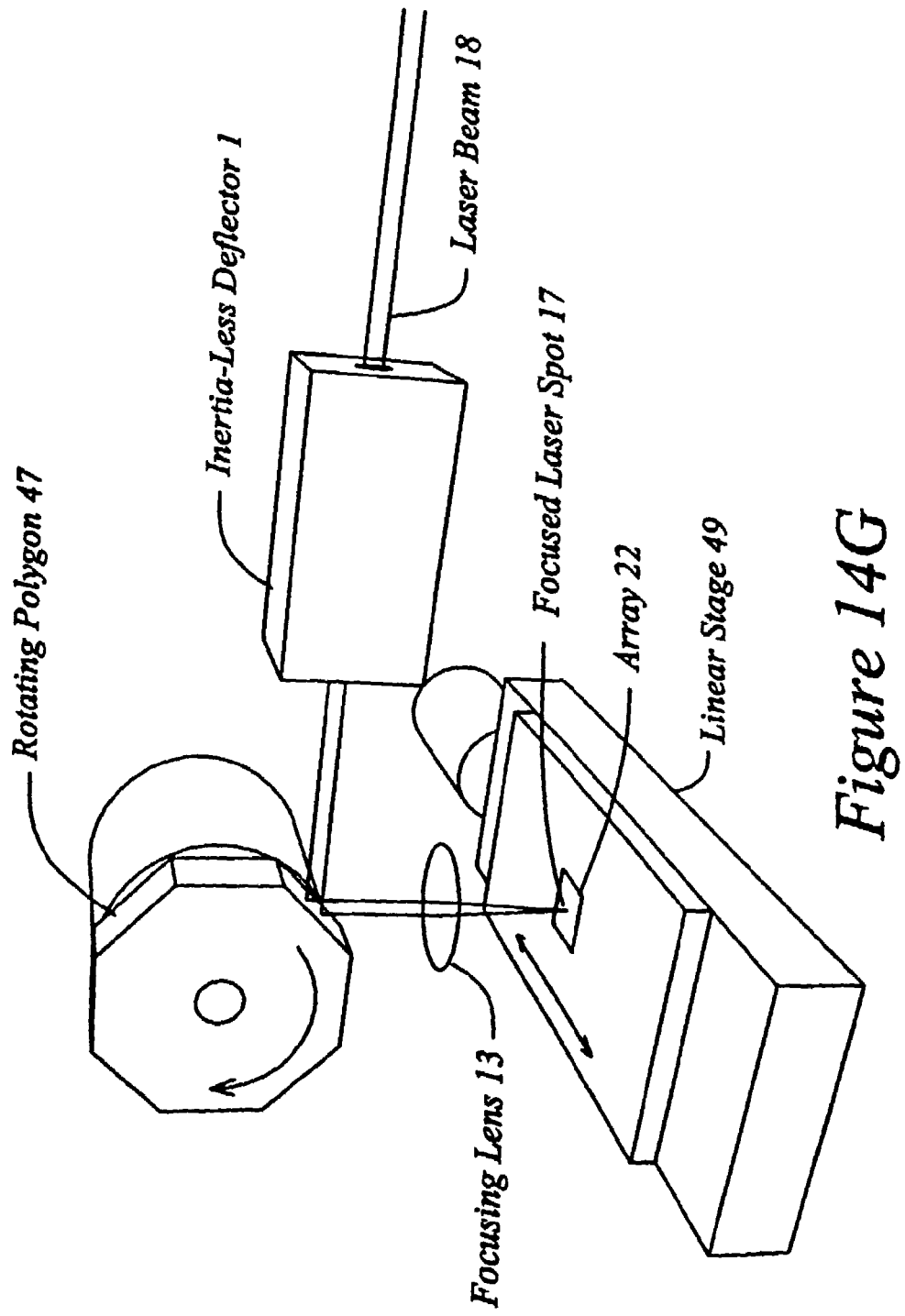

In FIG. 14G the wide range positioner is a rotating polygon 47 which moves the focused laser spot rapidly in the X direction while a linear stage moves the workpiece more slowly in the Y direction.

Figure 14H:
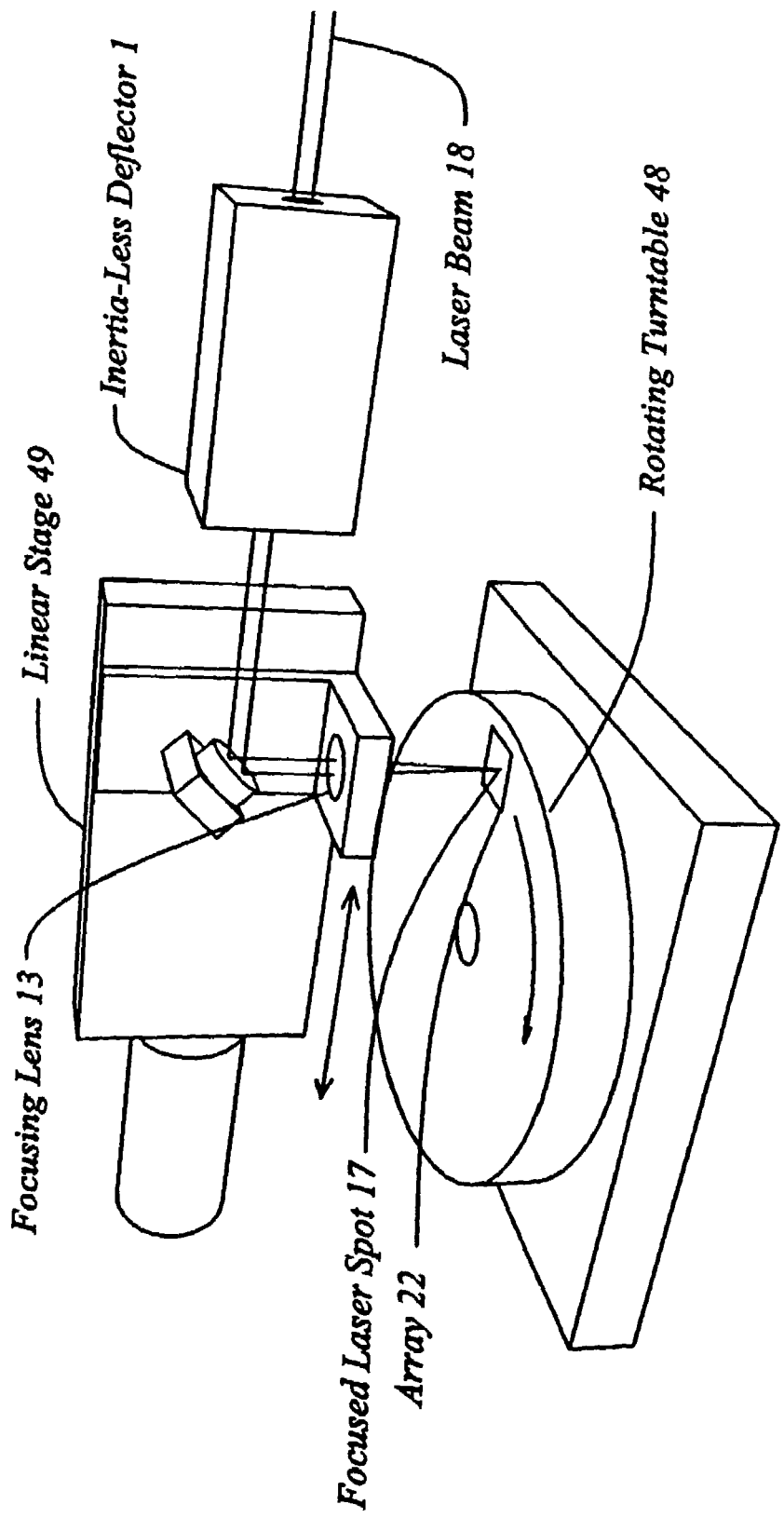

In FIG. 14H the wide range positioner is a rotating turntable 48 in combination with a linear stage which moves the focusing lens and the focused laser spot in the radial direction. In this case the turntable carries one or more workpieces. This and the case shown in FIG. 14G are examples in which reversal of motion in the X direction does not occur.

Figure 14I:
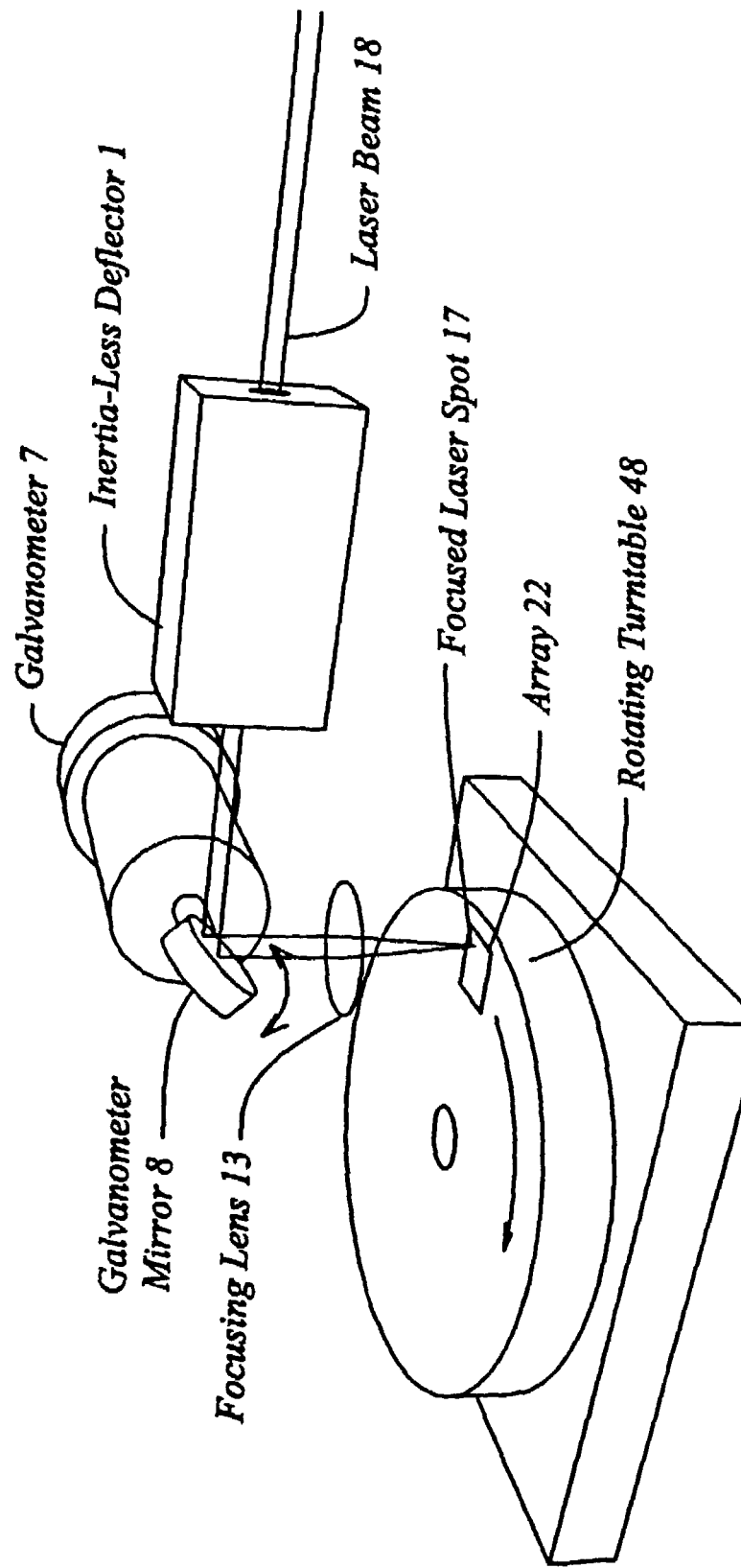

In FIG. 14I the wide range positioner is a rotating turntable in combination with a single axis galvanometer scanner. The turntable carries one or more workpieces and the single axis galvanometer scanner scans the laser beam in the radial direction while the scan lens is stationary.

The particular focusing lens best employed in an embodiment depends largely on the type of wide range positioner employed. In the case that galvanometer scanners are used, a wide field lens, usually referred to as a scan lens, is required. In the case of the flying lens scanner a small molded aspheric lens, possessing a very small field of view, is optimum. The focusing lens in a flying lens scanner is also commonly referred to as a scan lens because it moves, even though it can have a very small field of view. The most convenient lens, offering both high numerical aperture and low cost, is the microscope objective, and is the lens of choice when the lens is stationary or moves with low acceleration. When, as in the preferred embodiment, the lens collects fluorescent light, it is vital that it have high numerical aperture. The invention is useful with scanners in which the numerical aperture of the lens may be as low as 0.25, as employed for instance in scanners available from Agilent, however preferably the numerical aperature is at least 0.50, and preferably higher. Having high numerical aperture usually dictates that there is only space for one lens which both delivers laser light and collects fluorescent light. This requirement implies that in many cases the galvanometer scanners have a disadvantage since the wide field lenses used with them do not have numerical apertures as large as those of small field of view lenses.

DETAILS OF PREFERRED EMBODIMENTS EMPLOYING AN ACOUSTO-OPTIC DEFLECTOR

Figure 16:
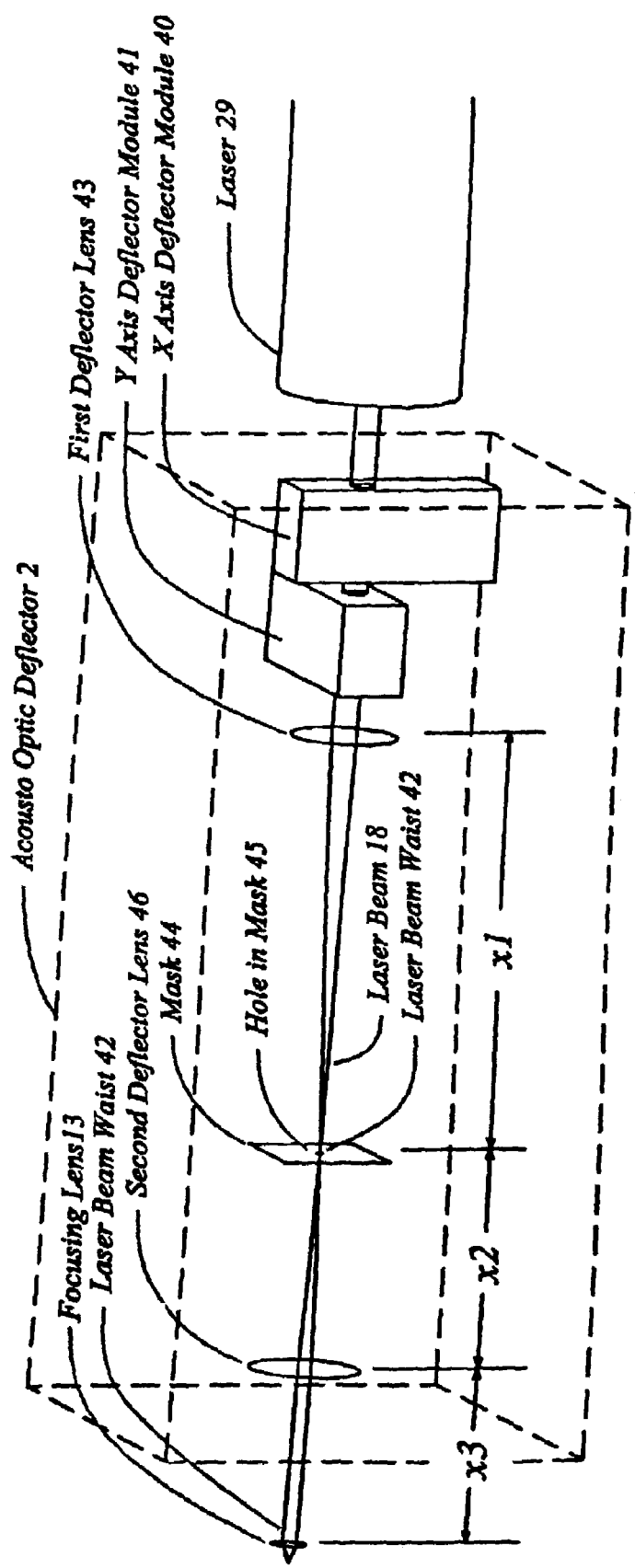
FIG. 16 shows a preferred embodiment of an acousto-optic deflector.

FIG. 16 shows that in the preferred embodiment of the acousto-optic deflector the approximately parallel laser beam 18 first enters two commercially available acousto-optic deflector modules, an x axis deflector module 40 and a y axis deflector module 41. These modules deflect a large fraction, approximately 85%, of the laser light over a small angular range, typically less than ten milliradians. The laser beam next enters a first deflector lens 43 which focuses the laser beam on the plane of a mask 44. The mask contains a hole which passes the large fraction of laser light. The area of the mask outside the hole blocks the remaining laser light, which has either not been deflected or has been deflected by multiples of the angle of the light which passes through the hole. Since the amount of laser power used in this application is small, the mask can absorb the laser light without damage. Also, since the laser light is in the visible range, the acousto-optic deflector modules have high efficiency, permitting simple implementation.

After passing through the hole in the mask, the laser beam passes through second deflector lens which restores the laser beam to being approximately parallel. The laser beam then proceeds to the focusing lens 13. The laser beam may also reflect from one or more mirrors, not shown, provided, e.g., to conform the optical path to a small space. The laser beam may also pass through a dichroic mirror, also not shown, when the invention is applied to detecting fluorescence. The effect of these mirrors on the design below is only to require the provision of space between the second deflector lens and the focusing lens.

In general, the lens system associated with the inertia-less deflector preferably has all of the following properties. A. Over the range of angles of the deflected beam, the position of the laser beam on the focusing lens remains unchanged. B. It produces the selected focused spot size and C. It accommodates the desired angular range of deflection produced by the inertia-less deflector in its novel stop and dwell action.

The following examples for the preferred embodiment are given at a level of detail greater than that required for present purposes. The examples demonstrate the practicality of a detailed design. Those skilled in optics, electronics, and computer design can provide other selections and arrangements.

Example of Component Selection and Design for Inertia-Less Deflector and Optics

The desired diameter of the focused laser spot w4 is determined by the laser wavelength λ, the focal length of the focusing lens foclen3, and the diameter of the laser beam at the focusing lens w3 by the equation:

$$w4=(4/\pi)\times\lambda\times(foclen3/w3) \quad \text{(Equation 2)}$$

Throughout this analysis, whenever a laser beam diameter is referred to, it means the diameter of a Gaussian laser beam between its 1/e squared power points.

A convenient design procedure is first to choose the laser for its cost, quality, and appropriateness of its wavelength for exciting fluorescence in the range of fluorophores to be employed, and to choose the focusing lens as described below. These choices will fix the beam diameter w0 at the laser and the beam diameter w3 at the focusing lens.

The focal lengths and positions of the first and second deflector lenses are next calculated so as to simultaneously A. change the laser beam diameter from w0 to w3, B. make the laser beam parallel when it reaches the focusing lens, implying that there is a beam waist at the focusing lens, and C. form an image of the output of the acousto-optic deflector modules at the focusing lens.

Forming an image of the output of the acousto-optic deflector modules at the focusing lens ensures that while the acousto-optic deflector modules change the direction of the laser beam when it enters the focusing lens, the position of the laser beam at the focusing lens will be unchanged. Otherwise, if the position of the laser beam changed, some of the laser light might miss the focusing lens, with a reduction in the amount of laser power delivered to the workpiece and a corresponding reduction in the amount of fluorescent light generated.

The simplifying assumption used in the calculations below, that the x and y acousto-optic deflector modules and the first deflector lens are in the same place, results in an amount of motion of the center of the laser beam on the focusing lens whose effect is negligible.

The focusing lens is primarily chosen to have high numerical aperture, denoted by NA3, in order to collect as much fluorescent light as possible. The fraction of fluorescent light collected equals $0.5 \times (1-\sqrt{1-NA3^2})$. The numerical aperture provided by a small molded aspheric lens such as the Geltech 350340 is 0.62, and the numerical aperture provided by microscope objectives is similar. The molded aspheric lens is preferable in the case that the wide range positioner is a flying lens scanner, in which the mass of the focusing lens should be as small as possible.

The focusing lens is selected to have reasonable working distance, such as 1 millimeter. In the case that the arrays are on the far side of a thin sheet of glass, as is the case with the Affymetrix GeneChip®, the lens is selected to have spherical aberration that cancels the spherical aberration introduced by the sheet of glass.

Examples of suitable lasers are green helium neon lasers with wavelength $\lambda=543.5$ nanometers and beam diameter w0=0.8 millimeters and doubled neodymium vanadate lasers with wavelength $\lambda=532$ nanometers and similar beam diameter.

In the calculation that follows, when numerical values are used, the wavelength $\lambda$ will be 543.5 nanometers, the laser beam diameter at the laser w0=0.8 millimeters, and the focal length of the focusing lens foclen3 will be 3.97 millimeters, the focal length of a Geltech 350340 lens at a wavelength of 543.5 nanometers.

The calculation will be done for two different diameters of the focused laser spot at the workpiece, w4A=10 micrometers and w4B=5 micrometers. Quantities with A appended to their symbols apply to the 10 micrometer case and quantities with B appended to their symbols apply to the 5 micrometer case.

The calculation that follows takes into account at every step the fact that the laser beam diameter is strongly affected by diffraction. The distance from the laser beam waist in which the laser beam diameter increases by a factor of sqrt(2)=1.4142 due to diffraction is known as the laser beam's Rayleigh range $z_R$, which is given by $$z_R = (\text{laser beam waist diameter})^2/(4\lambda/\pi) \quad \text{(Equation 3)}$$

The laser beam waist is the point along the laser beam's path at which the laser beam's diameter is a minimum, the wavefront is flat, and the rays considered to comprise the beam are parallel.

In the present application $z_R$ is comparable with the distances between components, in contrast with the situation in which it is small compared with the distances between components and classical ray tracing may be used to calculate focal lengths and locations of lenses.

The two laser beam diameters at the focusing lens, for the 10 micrometer and 5 micrometer spot size cases, applying Equation 2, are $$w3A = (4/\pi) \times \lambda \times (\text{foclen}3/w4A) = 0.2747 \text{ millimeters and}$$

$$w3B = (4/\pi) \times \lambda \times (\text{foclen}3/w4B) = 0.5495 \text{ millimeters.}$$

The Rayleigh ranges of the laser beam entering the focusing lens, applying Equation 3 are:

$$zr3A = (w3A)^2/(4\lambda/\pi) = 109.066 \text{ millimeters and}$$

$$zr3B = (w3B)^2/(4\lambda/\pi) = 436.265 \text{ millimeters.}$$

The magnifications required of the combination of the first and second deflector lenses are $$mA = w3A/w0 = 0.3434 \text{ and}$$

$$mB = w3B/w0 = 0.6869.$$

Denote the focal length of the first deflector lens by foclen1 and its distance from the mask by x1. Denote the focal length of the second deflector lens by foclen2 and its distance from the mask by x2. Assume that the acousto-optic deflector modules are sufficiently close to the laser that the laser beam diameter within the acousto-optic deflector modules is equal to w0. This assumption will be removed in the later calculation for the case that focused spot diameter is made variable.

In order that the output of the acousto-optic deflector modules be focused on the focusing lens the distance from the second deflector lens to the focusing lens must be approximately $$x3 = \text{foclen}2 \times (x1+x2)/(x1+x2-\text{foclen}2), \quad \text{(Equation 4)}$$

as can be shown by classical ray tracing. Estimate that x3=100 millimeters, since this is an appropriate distance to accommodate the dichroic mirror and mirrors such as those involved in a flying lens scan arm.

The curvature of the wavefront of a laser beam as a function of the laser beam's Rayleigh range $z_R$ and the distance x from the laser beam's waist is $$cu = 1/(x \times (1+(z_R/x)^2)) \quad \text{(Equation 5)}$$

The curvature of the wavefront leaving the second deflector lens will therefore be $cu3 = 1/(x3 \times (1+(zr3/x3)^2)$. cu3A=4.56716 inverse meters. cu3B=0.49918 inverse meters.

The diameter of a laser beam as a function of the laser beam's Rayleigh range $z_R$, the laser beam's diameter at its waist $w_0$, and the distance x from the laser's beam waist is $$w = w_0 \times \sqrt{1+(x/z_R)^2} \quad \text{(Equation 6)}$$

The diameter of the laser beam at the second deflector lens will therefore be $w2 = w3 \times \sqrt{1+(x3/zr3)^2}$. w2A=0.3727 millimeters. w2B=0.5637 millimeters.

Pick a value for foclen2 assuming that the distance x3 will be greater than 100 millimeters. Pick foclen2A=100 millimeters and foclen2B=75.6 millimeters, both of which are focal lengths of lenses in the Newport Corporation catalog.

A lens changes the curvature of a wavefront such that the sum of the curvatures on either side of the lens is equal to one divided by the lens' focal length. The curvature of the laser wavefront just prior to the second deflector lens is therefore $$(1/\text{foclen}2) - cu3$$

One can combine equations 5 and 6 to show that by knowing the curvature of the wavefront entering the second deflector lens and the diameter of the laser beam at the second deflector lens one can know the value of the dimensionless parameter a2=x2/Rayleigh range of beam between deflector lens 1 and deflector lens 2=x2/zr2.

$$a2 = ((1/\text{foclen}2) - cu3) \times w_2^2/(4\lambda/\pi) \quad \text{(Equation 7)}$$

a2A=1.09066. a2B=5.84469.

The diameter of the laser beam waist between the first and second deflector lenses is equal to the diameter of the laser beam in the plane of the mask=w1=w3/sqrt(1+a2$^2$) from Equation 6.

w1A=251.89 microns. w1B=95.07 microns.

The Rayleigh range of the laser beam between first and second deflector lenses=zr2=w1$^2$/(4λ/π).

zr2A=91.6873 mm. zr2B=13.0958 mm.

The distances x2 are given by x2=a2/zr2.

x2A=100.00 mm. x2B=76.33 mm.

The focal length of the first deflector lens, the distance x1, and the initial laser beam diameter must be such as to produce the same values of w1 and zr2 as have been just calculated based upon the requirement of 10 and 5 micrometer diameters of the focused laser spot. One can calculate x1 by inverting Equation 6:

1+(x1/zr2)$^2$=(w0/w1)$^2$ x1=zr2×sqrt((w0/w1)$^2$−1)

x1A=276.39 mm. x1B=109.12 mm.

From x1 one can calculate the dimensionless ratio a1=x1/zr2, and from a1 the curvature cu1 of the laser beam as it leaves the first deflector lens. Since the laser beam entering the first deflector lens is assumed to have zero curvature, the focal length of the first deflector lens foclen1=1/cu1.

a1A=3.01446. a1B=8.35562.

foclen1=1/cu1=x1×(1+(1/a1)$^2$))

foclen1A=306.80 mm. foclen1B=110.69 mm.

The distance x3 from the second deflector lens to the focusing lens is calculated from Equation 4: x3A=136.18 mm. x3B=127.63 mm.

Since these values of x3 are not the 100 millimeters that was originally assumed, one iterates the above calculation using these values of x3. After three iterations the important values become:

| | |
|---|---|
| foclen1A = 291.2 mm. | foclen1B = 110.1 mm. |
| x1A = 264.9 mm. | x1B = 108.5 mm. |
| x2A = 126.3 mm. | x2B = 77.1 mm. |
| x3A = 134.3 mm. | x3B = 127.5 mm. |
| w1A = 0.240 mm. | w1B = 0.095 mm. |

The quantities described above are summarized in Table 1. Also tabulated in Table 1 are the focal lengths and separation of two catalog lenses C and D which may be used to make the first deflector lens.

TABLE 1

| Subscript letter used in text description | A | B |
|---|---|---|
| Diameter of focused laser spot, in micrometers | 10.0 | 5.0 |
| Distances, in millimeters from first deflector lens to: | | |
| Mask, x1 | 264.9 | 108.5 |
| Second deflector lens, x1 + x2 | 391.2 | 185.6 |
| Focusing lens, x1 + x2 + x3 | 525.5 | 313.1 |
| Focal lengths of lenses, in millimeters: | | |
| First deflector lens, foclen1 | 291.2 | 110.1 |
| Second deflector lens, foclen2 | 100.0 | 75.6 |

TABLE 1-continued

| Subscript letter used in text description | A | B |
|---|---|---|
| (catalog values) | | |
| Focusing lens, foclen3 | 3.97 | 3.97 |
| Magnification required of first and second deflector lenses = w3/w0 | 0.3434 | 0.6869 |
| Catalog lenses comprising first deflector lens, dimensions in millimeters: | | |
| Focal length C | 88.3 | 50.2 |
| Focal length D | −100.0 | −75.0 |
| Separation between lenses C and D | 18.6 | 9.4 |
| Diameter of laser beam, in millimeters | | |
| at laser and first deflector lens, w0 | 0.8 | 0.8 |
| in plane of mask, w1 | 0.240 | 0.095 |
| at second deflector lens, w2 | 0.3727 | 0.5637 |
| at focusing lens, w3 | 0.2747 | 0.5495 |
| at workpiece | 0.0050 | 0.0100 |
| Rayleigh ranges, in millimeters | | |
| between first and second deflector lenses, zr2 | 91.6873 | 13.0958 |
| between second deflector lens and focusing lens, zr3 | 109.066 | 436.265 |

The next task is to calculate the properties of the mask, the range of motion provided by the acousto-optic deflector modules and the RF frequency deviation required to produce this range of motion. The two most common commercially available acousto-optic deflector modules are made of tellurium dioxide and lead molybdate. The angular range capabilities of these two materials are very different, so one must calculate the angular range and the properties of the mask separately for the two materials.

Numbers are presented for a convenient RF center frequency, 80 Mhz, but other frequencies could be used as well. A representative tellurium dioxide acousto-optic deflector module is the Isomet model LS-55V, and a representative lead molybdate acousto-optic deflector module is the Isomet model 1705C. For a shear wave acousto-optic deflector using tellurium dioxide:

Denote the total range of motion required of the acousto-optic deflector as y4, and express it as a small multiple mu, of the diameter of the focused spot w4. Let the multiple be mu=6.

y4A=6×10=60 micrometers, y4B=6×5=30 micrometers.

The total angular range required of the acousto-optic deflector is h=m×mu×w4/foclen3.

hA=0.3434×6×10/3.97=5.19 milliradians.
hB=0.6869×6×5/3.97=5.19 milliradians.

The Bragg angle at 80 MHz acoustic frequency is g=laser wavelength/(2×sound wavelength)=0.5435×10$^{-6}$ meters× 0.8×10$^8$/(2×sound velocity of shear waves in tellurium dioxide=617 meters per second)=35.235 milliradians.

The frequency deviation from 80 MHz required is fd=(h/4 g)×80 MHz=2.945 Mhz, so the total range=5.89 MHz.

The modulation bandwidth provided by the Isomet model LS-55V (for reduction of MTF to 50% of peak value), mbw=40 MHz. The reduction from peak deflection efficiency implied by the frequency deviation of 2.945 MHz= (2×fd/mbw)$^2$=0.0216, which is negligible.

The distance between the undeflected and nominally (i.e., at 80 MHz) deflected laser beam at the mask, y2=2×g× foclen1. y2A=20.53 mm. y2B=7.762 mm.

The required width of the hole in the mask, with an additional 5 spot diameters added to relax alignment requirements is wm=h×foclen1+6w1. wmA=2.951 mm. wmB=1.1414 mm. Circular holes of 0.164 inch and 0.064 inch diameter will do the job equally well.

The time required for the acousto-optic deflector to change the direction of the laser beam, tslew=the width of laser beam w0 divided by the sound velocity of shear waves in tellurium dioxide=617 meters per second. tslew=1.3 microseconds. For a compression wave acousto-optic deflector using lead molybdate:

Again denote the total range of motion required of the acousto-optic deflector by y4, and express it as a small multiple mu, of the diameter of the focused laser spot w4. In this case let the multiple be mu=2.5. y4A=2.5×10=25 micrometers, y4B=2.5×5=12.5 micrometers.

The total angular range required of the acousto-optic deflector, is h=m×mu×w4/foclen3.

$$hA=0.3434\times2.5\times10/3.97=2.1625 \text{ milliradians.}$$
$$hB=0.6869\times2.5\times5/3.97=2.1625 \text{ milliradians.}$$

The Bragg angle at 80 MHz acoustic frequency is g=laser wavelength/sound wavelength=$0.5435\times10^{-6}$ meters×$0.8\times10^8$/(2×sound velocity of compression waves in lead molybdate=3630 meters per second)=5.99 milliradians.

The frequency deviation from 80 MHz required is fd=(h/4 g)×80 MHz=7.22 Mhz so the total range=14.44 MHz. The measured decrease in diffraction efficiency from its value at 80 MHz for 8 MHz deviation is 6.7%, which is acceptable.

The distance between the undeflected and nominally (i.e., at 80 MHz) deflected laser beam at the mask, y2=2×g×foclen1. y2A=3.489 mm. y2B=1.319 mm.

The required width of the hole in the mask, with additional 5 spot diameters added to relax alignment requirements is wm=h×foclen1+6w1. wmA=2.070 mm. wmB=0.808 mm. Circular holes of 0.115 inch and 0.045 inch diameter will do the job equally well.

The time required for the acousto-optic deflector to change the direction of the laser beam, tslew=the width of laser beam w0 divided by the sound velocity of compression waves in lead molybdate=3630 meters per second. tslew=0.22 microseconds.

The quantities determined by a tellurium dioxide acousto-optic deflector module and a lead molybdate acousto-optic deflector module are summarized in Table 2.

TABLE 2

| Deflector Material | Tellurium Dioxide | Lead Molybdate |
|---|---|---|
| Central RF Frequency, MHz | 80.0 | 80.0 |
| Bragg Angle at Central RF Frequency, g, milliradians | 35.235 | 5.99 |
| Total Angular Range, h, milliradians | 5.19 | 2.165 |
| Peak frequency deviation from Central RF Frequency, fd, MHz | 2.945 | 7.22 |
| For 10 micrometer diameter focused laser spots: | | |
| Distance between undeflected beam and beam deflected at Central RF frequency, at mask, y2A, millimeters | 20.53 | 3.489 |
| Width of opening in mask, wmA, millimeters | 2.951 | 2.070 |
| For 5 micrometer diameter focused laser spots: | | |
| Distance between undeflected beam and beam deflected at Central RF frequency, at mask, y2B, millimeters | 7.762 | 1.319 |
| Width of opening in mask, wmB, millimeters | 1.1414 | 0.0808 |
| Time tslew, microseconds | 1.3 | 0.22 |

Example of Electronics for Driving the Acousto-Optic Deflector

In the presently preferred embodiments, each acousto-optic deflector includes a piezoelectric transducer which launches sound waves into the optical medium, typically tellurium dioxide or lead molybdate. The piezoelectric transducer is driven by an RF waveform shown in FIG. 17. The time during which the RF frequency changes suddenly, when switching from one array element to the next, is shown as tslew. The much longer time, during which the RF frequency changes approximately linearly, is shown as tdwell. Tslew is typically one microsecond or less and tdwell is typically 200 microseconds. The RF waveform is provided by an RF power amplifier 75, shown in FIG. 18 as part of the analog electronics 70 for controlling either axis of the acousto-optic deflector.

Figure 17:
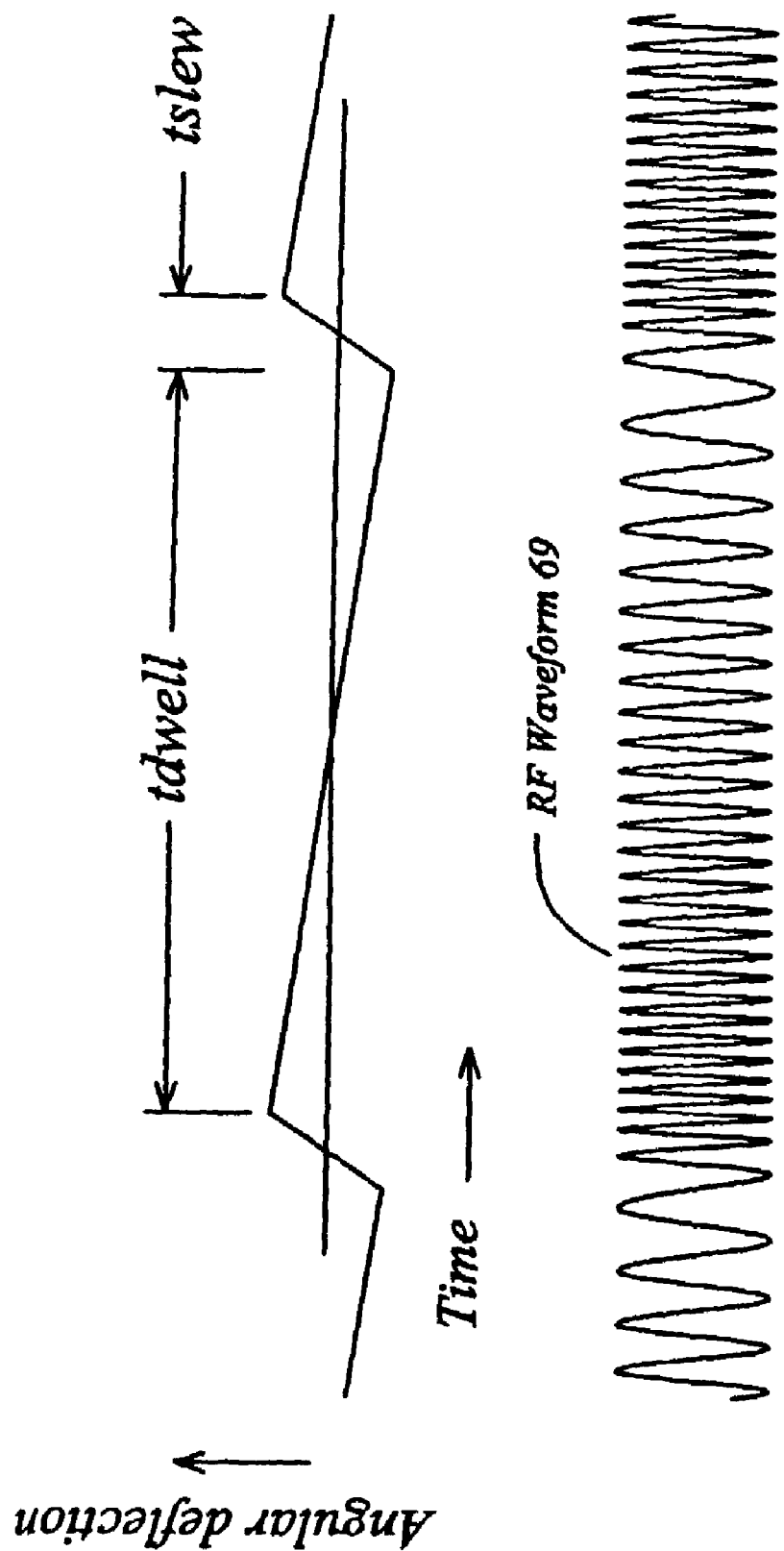
FIG. 17 shows an RF waveform applied to one axis of the acousto-optic deflector and the resulting deflection angle.
Figure 18:
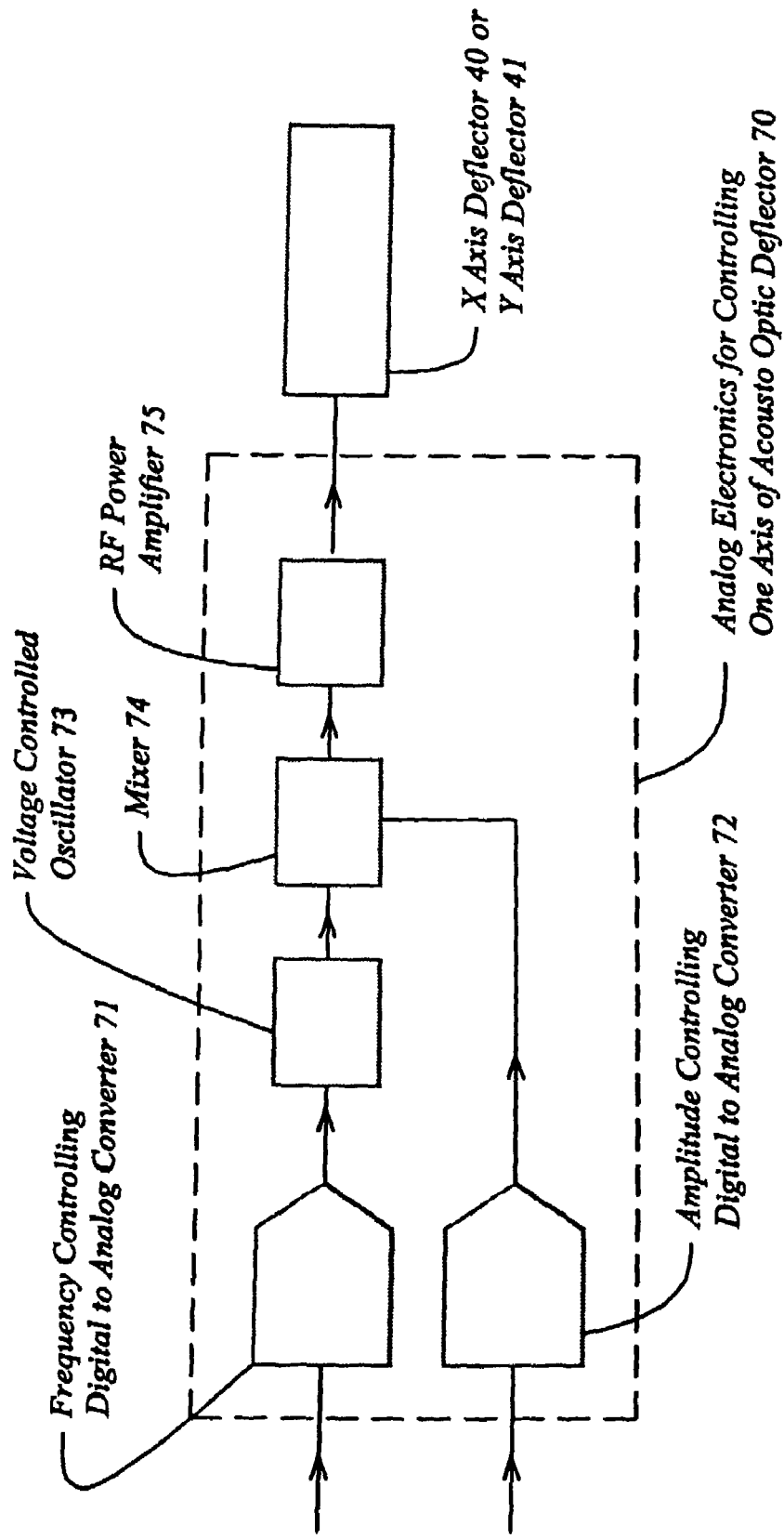
FIG. 18 shows analog electronics used to drive either axis of the acousto-optic deflector.

The angle by which light is deflected is proportional to the RF frequency, as shown in FIG. 17, so the angle is varied by varying the frequency provided by the voltage controlled oscillator 73. The variable voltage which controls the frequency of the voltage controlled oscillator is provided by a digital to analog converter, denoted by the frequency controlling digital to analog converter 71. Another digital to analog converter, the amplitude controlling digital to analog converter 72, is provided, in conjunction with the mixer 74, to control the amplitude of the RF waveform and hence the amount of deflected laser light.

When applied to exciting fluorescence, it is desirable not to apply laser light to a fluorophore unnecessarily, because fluorophores bleach, i.e., lose their ability to fluoresce. This invention, through the amplitude controlling digital to analog converter and the mixer, provides the ability to turn off the laser light in the case that an array element is scanned a second time. The software and digital electronics, described later, controls a signal named RF ON, that controls the digital number sent to the amplitude controlling digital to analog converter, and hence the laser power reaching the workpiece.

The ability to control the amount of laser power is desirable for other purposes, including: A. using attenuated reflected laser light to sense the position of reflective fiducials, and B. maintaining the laser power constant over time and from scanner to scanner.

Typical components for implementing the above described electronics include the Mini-Circuits ZHL-1-2W RF power amplifier, the Mini-Circuits SBL-1-1LH mixer, the Mini-Circuits ZOS-100 voltage controlled oscillator, and the Analog Devices AD566AJD 12 bit digital to analog converter.

The above digital to analog converters could be loaded with new values approximately every microsecond by a dedicated computer. Software to control such a computer is described below. It is simpler and less expensive, however, to have the new values provided by logic within a field programmable array (FPGA.) Using the FPGA relieves the computer which controls the system from responding to interrupts on a 1 microsecond time scale, and instead allows it to respond to interrupts on a 20 microsecond time scale.

FIGS. 19A through 19F show digital electronic circuitry which implements the same algorithm as the software. All the circuitry shown in FIGS. 19A through 19F, with the exception of the semiconductor memory for storing the fluorescence data and a crystal oscillator, can fit into an FPGA which costs very little. The circuitry as shown uses static random access memory (SRAM) for storing the data, but it would be easy to add memory refresh circuitry within the FPGA to enable it to use less expensive dynamic random access memory (DRAM.) A typical FPGA suitable for this task is the Altera EPF6016.

Example of Operation of a Field Programmable Gate Array (FPGA)

Figure 19A:
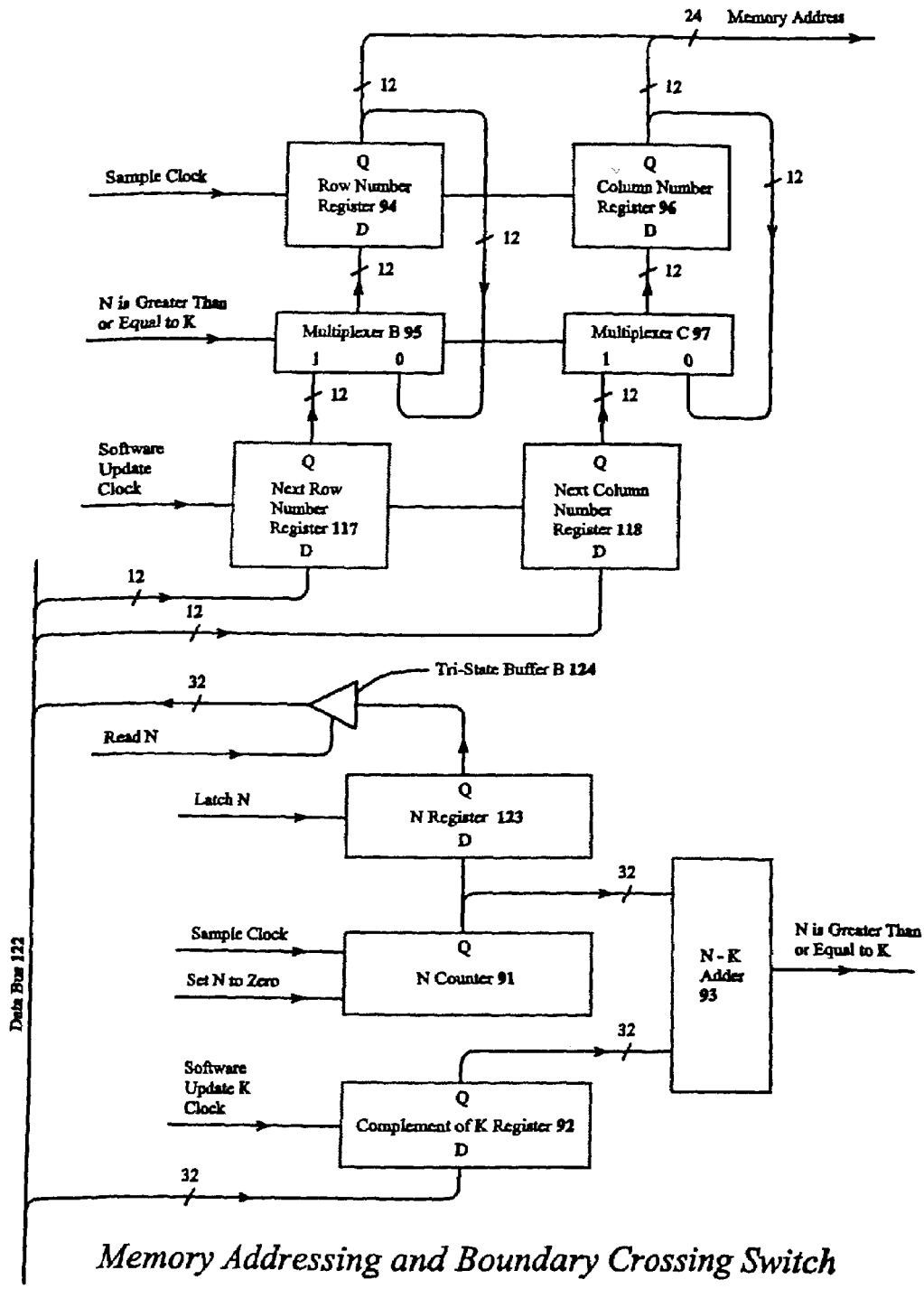
FIGS. 19A through 19F show digital electronics used to control the acousto-optic deflectors and to collect fluorescence data.
Figure 19B:
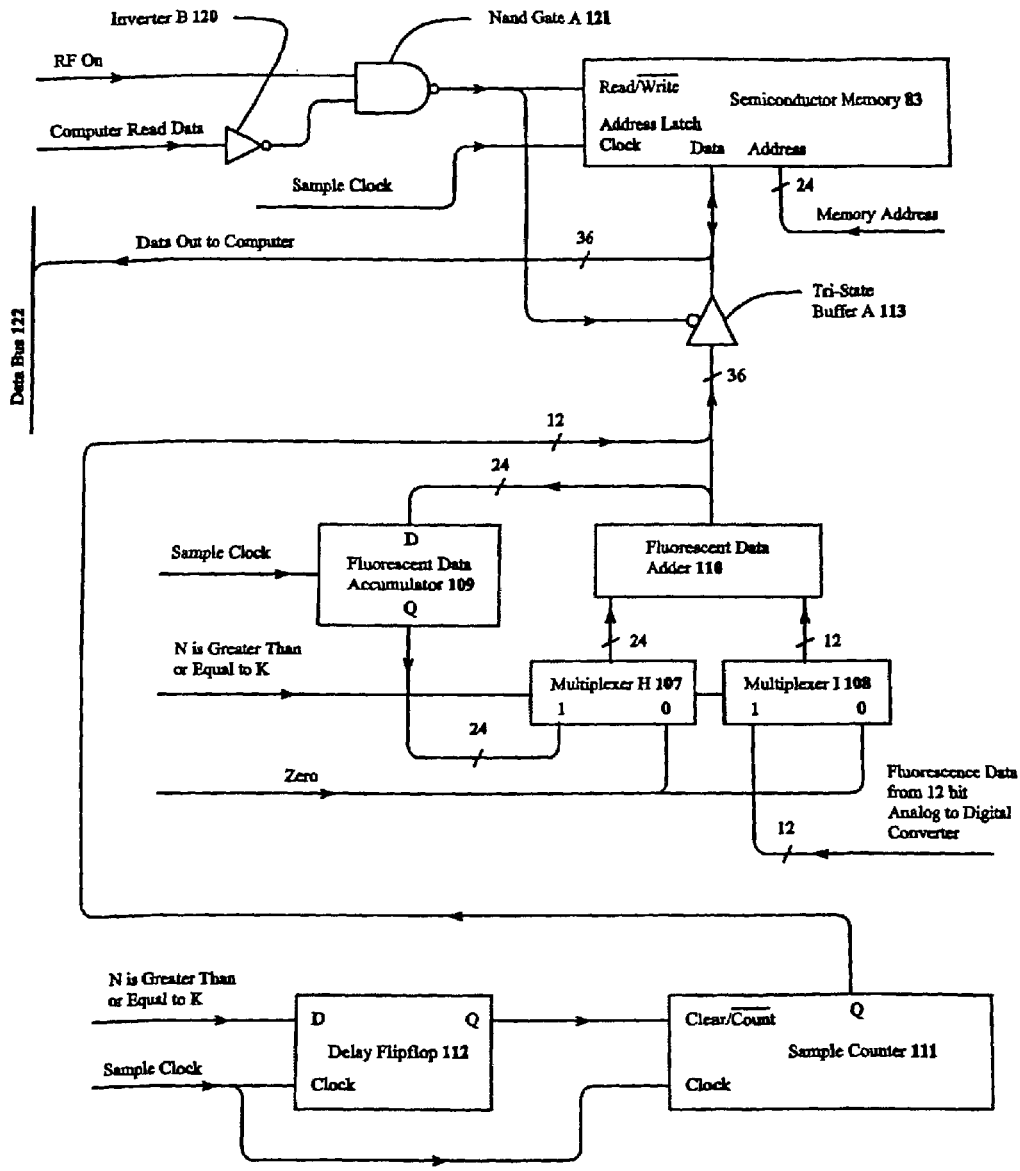
Figure 19C:
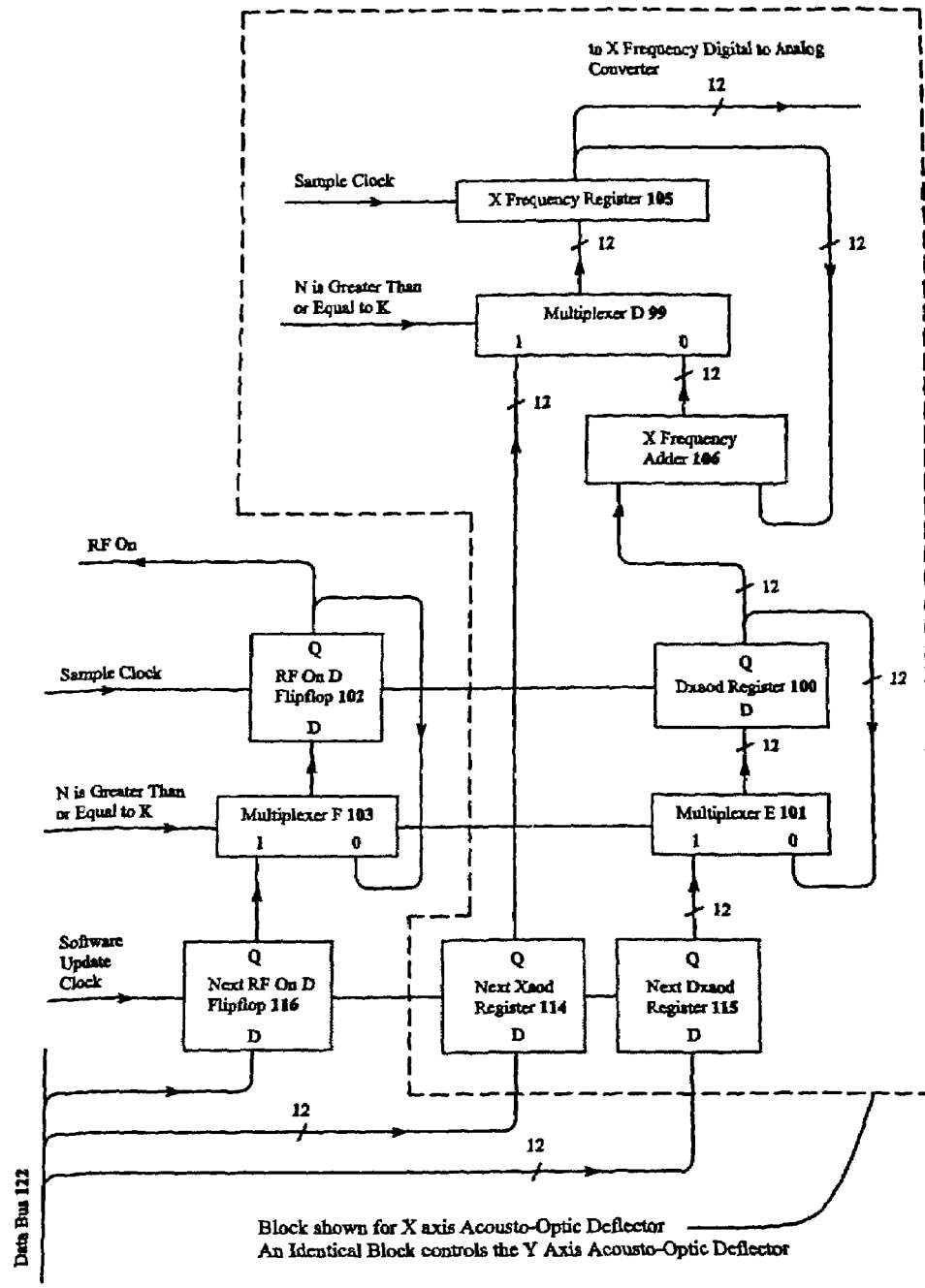
Figure 19D:
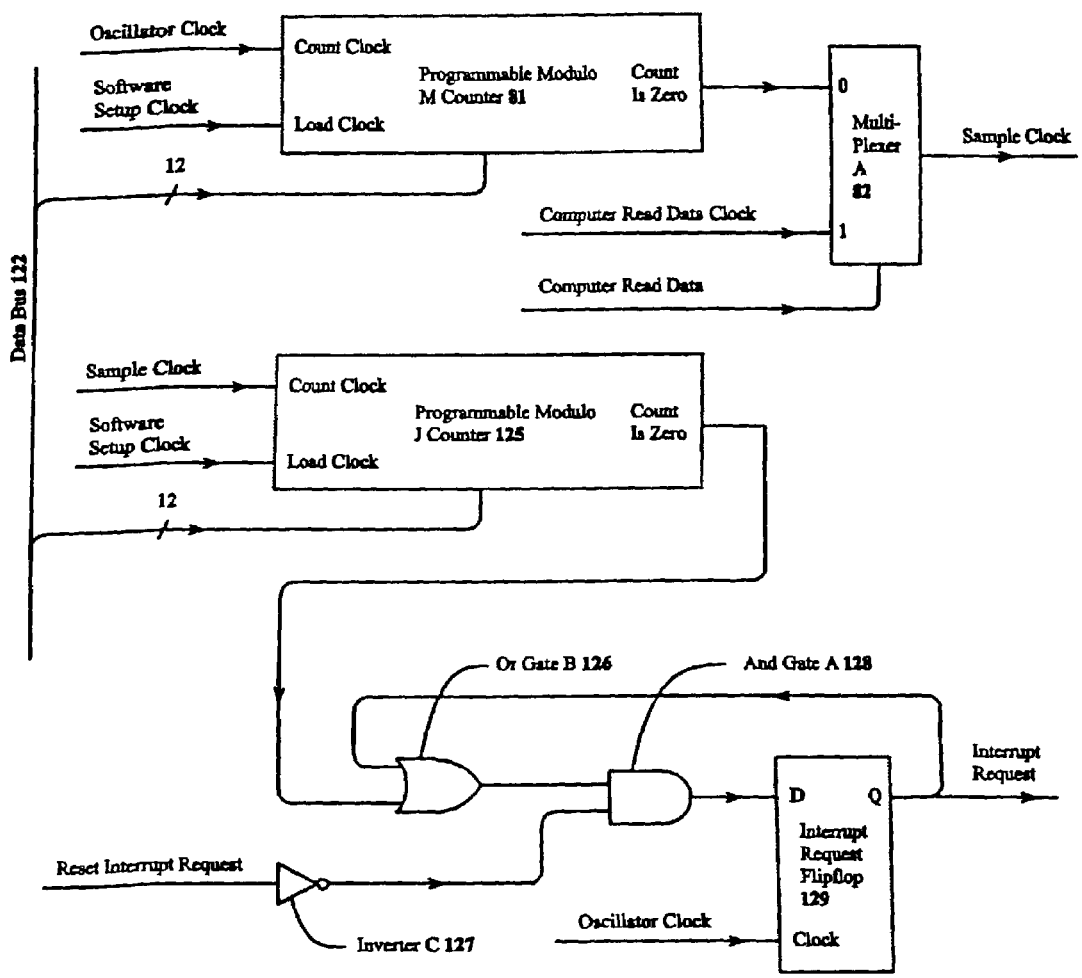
Figure 19E:
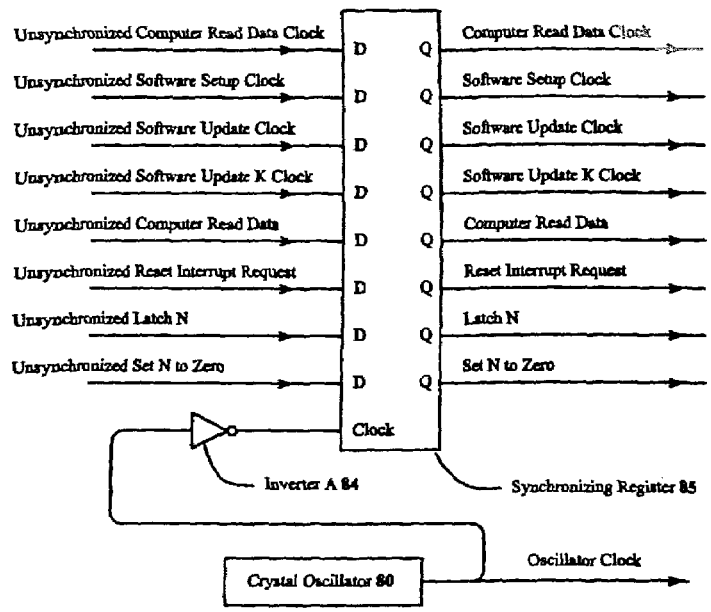

All timing is regulated by Crystal Oscillator 80, located outside the FPGA, shown in FIG. 19E, which generates a signal named "Oscillator Clock." The Crystal Oscillator operates at a frequency higher than the frequency of updates of the digital to analog converters (DACs) which control the generation of RF waveforms for the acousto-optic deflectors (AODs). A typical frequency for the Crystal Oscillator is 40 MHz and a typical update frequency is 1 MHz.

The Programmable Modulo M Counter 81, shown in FIG. 19D, divides the Crystal Oscillator's frequency by a factor m, which is loaded into the Programmable Modulo M Counter by software via the signal "Software Setup Clock", enabling software selection of the update frequency. For the frequencies given above the value of m is 40. The output of the Programmable Modulo M Counter is labeled "Count is Zero." "Count is Zero" is true, i.e., at a high logic level, for one period of the Crystal Oscillator once per m pulses from the Crystal Oscillator. Multiplexer A, 82, selects whether the "Count is Zero" signal or a clock controlled by software, labeled "Computer Read Data Clock" is used as the clock signal named "Sample Clock" which is the clock which drives most of the process of updating the DACs serving the AODs.

When the signal named "Computer Read Data", provided by software, is true, "Sample Clock" is equal to "Computer Read Data Clock." This situation occurs after scanning an array, when software reads out from the semiconductor memory 83, shown in FIG. 19B, the fluorescent data that has been stored during the scan. Inverter A 84, shown in FIG. 19E, produces a clock signal whose rising edge occurs at the time of the trailing edge of the clock from the Crystal Oscillator, ensuring that it does not occur at a time near the rising edge of the signal "Sample Clock". This in turn ensures that the eight signals used by software, "Computer Read Data Clock", "Software Setup Clock", "Software Update Clock", "Software Update K Clock", "Computer Read Data", "Reset Interrupt Request", "Latch N", and "Set N to Zero" do not change state at or near the time that "Sample Clock" goes from false to true.

Each of the eight D Flipflops within Synchronizing Register 85 has the property that its Q output changes state to match the state of its D input when its clock input changes from a false to a true state. This ensures the eight Q outputs change state a very short time, typically less than 3 nanoseconds, after the output of the Crystal Oscillator changes from a true to a false state.

The function of "Software Update Clock" is to enable entry of the new values for the quantities xaod, yaod, dxaod, dyaod, rf on, the next row number, and the next column number, described in the software description below. The function of "Software Update K Clock" is to enable entry of a new value of the complement of the number k into the Complement of K Register 92 shown in FIG. 19A. K is the value of n at which the digital logic switches from keeping the focused laser spot centered on one array element to keeping the focused laser spot centered on the next array element.

Figure 19F:
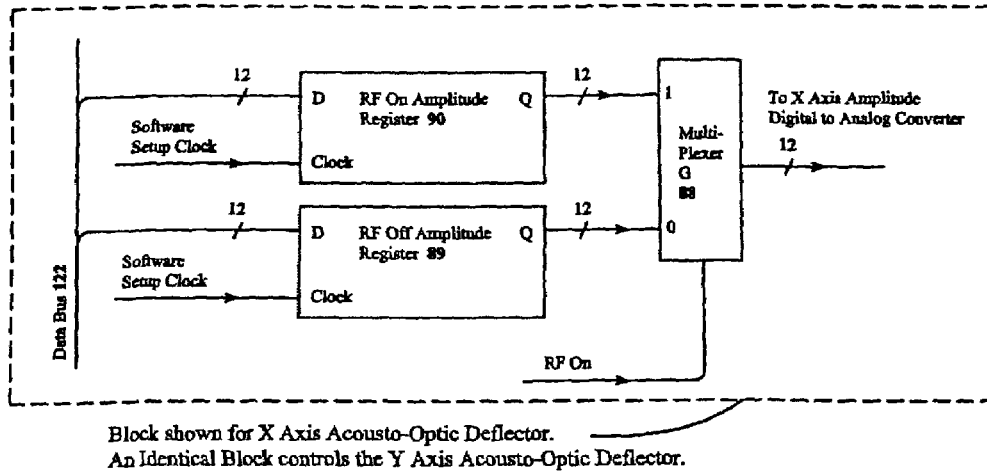

The function of "Software Setup Clock" is to enable entry of quantities which would normally be entered only before a scan starts: the number m described above, the number j into the Programmable Modulo J Counter 125, shown in FIG. 19D, the amplitude value for the RF waveform when the RF signal is to be off into RF Off Amplitude Register 89, shown in FIG. 19F, and the amplitude value for the RF waveform when the RF signal is to be on into the RF On Amplitude Register 90, also shown in FIG. 19F.

J is the number of occurrences of "Sample Clock" between interrupts to the computer, and is typically 20.

Operation of the FPGA during the time when the wide range positioner is near the middle of an array element is characterized by the number k being greater than the number n contained in the N Counter 91 shown in FIG. 19A. The complement of k is contained in the Complement of K Register 92. The N–K Adder 93 forms the sum of n and minus k, i.e., the difference n–k. The precise value of n–k is not used; only the information whether n–k is positive or negative is used. When n–k is positive (including zero) the output of the N–K Adder labeled "N is Greater Than or Equal to K" is true.

First the case in which "N is Greater Than or Equal to K" is false will be described. In this case at every time that "Sample Clock" goes from false to true the following things occur:

A. The row number in the array, i.e., the contents of Row Number Register 94, are made equal to their current value, i.e., they are unchanged, because Multiplexer B 95 connects the Q outputs of the Row Number Register to the D inputs of the Row Number Register.

B. Similarly, the column number in the array is unchanged through the similar action of Column Number Register 96 and Multiplexer C 97.

C. Similarly, the value of dxaod is unchanged through similar action of Dxaod Register 100 and Multiplixer E 101, shown in FIG. 19C.

D. Similarly the value of dyaod is unchanged. This value is held by a Dyaod Register, not shown, whose operation is identical to that of the Dxaod Register. The dashed section of circuitry shown in FIG. 19C depicts circuitry specific to the x axis acousto-optic deflector. Identical circuitry to that in the dashed section controls the y axis of the acousto-optic deflector.

E. The state of the RF waveform, i.e., whether the RF waveform is on or off, is similarly unchanged through similar action of the RF On D Flipflop 102 and Multiplexer F 103.

F. Multiplexer D 99 allows the output of the X Frequency Adder 106 to enter the X Frequency Register 105. The two inputs to the X Frequency Adder are the output of the X Frequency Register and the output of the Dxaod Register. When "Sample Clock" goes from false to true the X Frequency Register is therefore updated to contain a number which is larger by dxaod than the previous value of the contents of the X Frequency Register. This provides the angular velocity of the laser beam that cancels the x component of the velocity of the wide range positioner. As noted above, there is a Y Frequency Register, a Y Frequency Adder, etc. that operates in identical fashion.

G. As shown in FIG. 19B, the output of the Fluorescent Data Adder 110, is entered into the Fluorescent Data Accumulator 109. The two inputs to the Fluorescent Data Adder are the most recently acquired fluorescent light measurement from the analog to digital converter (ADC) serving the fluorescence detector, and the current contents of the Fluorescent Data Accumulator. Thus, with every occurrence of "Sample Clock", a number proportional to the amount of fluorescent light is added to the value in the Fluorescent Data Accumulator.

H. The number of additions to the Fluorescent Data Accumulator is approximately constant from one array element to the next, but its value will vary by a small amount, typically less than 3%, from one array element to the next. Therefore the number of additions per array element is counted in the Sample Counter 111, shown in FIG. 19B. The contents of the Sample Counter are incremented once for every occurrence of "Sample Clock" provided that "N is Greater Than or Equal to K" was false prior to the previous occurrence of "Sample Clock". A delay of one period of "Sample Clock" is provided by Delay Flipflop 112 so that a value of zero is entered into the Sample Counter during the time that the focused laser spot is moving rapidly from one array element to the next I. Data from the Fluorescent Data Accumulator and from the Sample Counter passes through Tri State Buffer A 113 to the bi-directional data input-output pins of the semiconductor memory and is entered into the Semiconductor Memory on the rising edge of the "Sample Clock" signal. Note that if the focused laser spot remains centered on an array element for 200 occurrences of "Sample Clock", for example, progressively increasing values are entered into the same location in the Semiconductor Memory. Only the last of these values is kept, and the entry of the other values causes no harm. The clock input to the Semiconductor Memory latches the values of the address inputs to the Semiconductor Memory, which is necessary because the address inputs would otherwise change immediately after the last occurrence of "Sample Clock" for an array element.

Next the case in which "N is Greater Than or Equal to K" is true will be described. In this case at every time that "Sample Clock" goes high the following things occur:

A. The Q output of the Delay Flipflop goes to the true state, in preparation for the zeroing of the Fluorescent Data Accumulator and the Sample counter, which is to occur one period of "Sample Clock" later.

B. A new value of xaod held by the Next Xaod Register 114, shown in FIG. 19C, is entered into the X Frequency Register via Multiplexer D.

C. A new value for dxaod is entered into the Dxaod Register from the Next Dxaod Register 115 via Multiplexer E.

D. Similarly new values of Yaod and Dyaod are entered into circuitry identical to that for the x axis of the acousto-optic deflector.

E. A new value for the variable "RF On" is entered into the RF On D Flipflip from the Next RF On D Flipflop 116 via Multiplexer F.

F. A new value for the row number is entered into the Row Number Register from the Next Row Number Register 117, shown in FIG. 19A, via Multiplexer B.

G. Similarly a new value for the column number is entered into the Column Number Register from the Next Column Number Register 118 via Multiplexer C. Together the outputs of the Row Number Register and the Column Number Register form the address inputs to the Semiconductor Memory, labeled "Memory Address."

One period of "Sample Clock" after the events described immediately above the following things occur:

A. The contents of the Fluorescent Data Accumulator are set equal to zero as described above. The delay of one period is provided by the Delay Flipflop.

B. The contents of the Sample Counter are similarly set to zero.

Prior to the signal "N is Greater Than or Equal to K" becoming true, software calculates the value of k that determines when this is to occur. It uses the "Software Update K Clock" to enter the complement of this value of k into the Complement of K Register 92. Just prior to this time, software enters the next values of xaod, dxaod, yaod, dyaod, rf on, the next row number and the next column number into registers as follows:

Xaod into the Next Xaod Register, dxaod into the Next Dxaod Register, yaod and yyaod into the corresponding registers for the y axis, rf on into the Next RF On D Flipflop, the next row number into the Next Row Number Register, and the next column number into the Next Column Number Register.

The eight software generated signals which are inputs to the Synchronizing Register, and have the qualifier "Unsynchronized" at the beginning of their names, shown in FIG. 19E, all must have durations greater than the time between successive pulses from the Crystal Oscillator, 25 nanoseconds in the case of a 40 MHz Crystal Oscillator Frequency, in order that the output signals from the Synchronizing Register, without the qualifier "Unsynchronized" perform their desired functions.

Note also that since "Software Setup Clock" and "Software Update Clock" each clock several different registers, it will usually be convenient for there to be several different clocks, such as "Software Update Clock 1", "Software Update Clock 2", etc., one for each register. The exposition is simpler if just one "Software Update Clock" is described because all of the several different clocks share the same timing requirements.

The operation of the FPGA is simplest if the "Software Setup Clock" which clocks the Programmable Modulo M Counter is used only prior to scanning an array. The "Software Setup Clock" which clocks the RF On Amplitude Register or the RF Off Amplitude Register, holding values for the x amplitude digital to analog converter, may be used at any time.

For a small fraction of the total time the wide range positioner will pass over an array element that it has scanned on a previous scan, and the next array element in the column will be accessed on the next scan. In this case the scanner will be idle until the next column is reached. For this situation the value of "RF On" is false. When "RF On" is false the value in the RF Off Amplitude Register, rather than the value in the RF On Amplitude Register, is sent to the x axis amplitude digital to analog converter by the action of Multiplexer G 88, shown in FIG. 19F.

Also, when "RF On" is false, the output of Nand Gate A 121, shown in FIG. 19B, becomes true, switching the Semconductor Memory from write mode to read mode, inhibiting entry of any new fluorescent data. The output of the Nand Gate A also causes Tri State Buffer A to "tri-state" its outputs, i.e., not pass fluorescent data to the data input-output pins of the Semiconductor Memory, since these pins act as outputs when the read/write bar input to the semiconductor memory is true. The request from the computer to read data from the Semiconductor Memory, "Computer Read Data", since an inverted version of it also enters Nand Gate A, causes the same results when "Computer Read Data" is true as described when "RF On" is true. The inversion of the signal "Computer Read Data" is done by Inverter B 120, shown in FIG. 19B.

When software calculates values of xaod, yaod, k, etc., it needs to know the position of the wide range positioner and it needs to know the time corresponding to its measurement of the wide range positioner's position. This measurement of time is provided by the N Register 123, shown in FIG. 19A. At any time that software makes the signal "Latch N" go from false to true, the value held in the N Counter is copied into the N Register. Subsequently software makes the signal "Read N" go true, and puts the value of the N Register onto the Data Bus 122, shown in FIGS. 19A, 19B, 19C, 19D, and 19F.

The Data Bus is shown as one bi-directional bus through which all data passes to and from the computer, as if the digital logic described above resided within a computer. This need not be the case. The data from the N Register and from Semiconductor Memory could travel on different paths, separate from paths carrying data from the computer, for example. Data to the computer could first go to one or more parallel to serial converters and then be sent serially to the computer, for example. Data from the computer could similarly arrive at the FPGA from one or more serial to parallel converters. The serial to parallel and parallel to serial converters could be contained within the same FPGA as the above described digital logic. Generation of the eight or more control signals entering the Synchronizing Register from the computer could similarly be done by the FPGA's decoding a serially sent command which is different for each of the control signals.

A source of regular clock pulses completely separate from the above described circuitry could generate interrupts to the computer, with the only requirement being that there be no more than approximately 50 microseconds between pulses if the dwell time, tdwell, per array element is 200 microseconds, for example. However circuitry shown in FIG. 19D may be used to generate the regular interrupts in a more regular fashion, i.e., one computer interrupt per j occurrences of the signal "Sample Clock". The output of the Programmable Modulo J Counter, "Count is Zero", is true for one period of "Sample Clock" once every j occurrences of "Sample Clock." When "Count is Zero" is true the Q output of the Interrupt Request Flipflop 129, named "Interrupt Request", goes true the next time that "Oscillator Clock" goes true. Or Gate B 126 and And Gate A 128 ensure that this happens and that "Interrupt Request" remains true until "Reset Interrupt Request", a signal initiated by software, goes true. "Reset Interrupt Request" going true makes the output of And Gate A go false, and therefore the Q output of the Interrupt Request Flipflop go false after the next occurrence of "Oscillator Clock." The signal "Reset Interrupt Request" is inverted by Inverter C 127.

When the scan of an array is complete the computer reads the accumulated data from the Semiconductor Memory by making the signal "Computer Read Data" become true, by repetitively loading different numbers into the Next Row Number Register and the Next Column Number Register, in order to generate a desired value for "Memory Address", and by generating "Sample Clock" pulses. The "Sample Clock" pulses are copies of the software initiated signal "Computer Read Data Clock", rather than copies of the output of the Programmable Modulo M Counter, because of the action of Multiplexer A.

Variable Diameter of Focused Laser Spot

In most optical scanners the diameter of the focused laser spot is chosen to give the best possible spatial definition. In embodiments of the present invention, for excitation of fluorophores, the phenomenon of fluorophore saturation is dealt with by using a new criterion for the diameter of the focused laser spot, preferably also employing steps to fill a significant area of each array element with the focused laser spot.

According to another aspect of the invention, a mechanism enabling change of laser spot size is included in a preferred scanner, enabling different, selectable modes of operation of the scanner, see FIG. 20C, described below. Thus potential conflicts between the desire, at times, to have spatial resolution and the desire, at other times, to have the focused laser spot be large e.g. in order to reduce the photon flux seen by a fluorophore are accommodated.

One use of the mechanism is for finding the location of array elements relative to the coordinate system of the wide range positioner, which is addressed by scanning the array twice. The purpose of the first scan, conducted with a small laser spot size, is to find the locations of features in the array and the purpose of the second scan, conducted with a larger laser spot size, is to measure fluorescent intensity. The first scan takes much less time than the second scan.

In theory, if fiducial marks were well separated on an array, the first scan could be done with a large spot, without sacrificing any accuracy in locating the array. However in current commercial systems a 2.5 micrometer diameter focused laser spot is employed, and for practical reasons it can be advantageous to use this small spot size diameter in embodiments of the present invention. This is achieved according to the invention by providing a scanner whose spot size can be changed quickly, and under computer control, employing two sets of lenses and masks and a mechanism for changing spot size.

In another case, an element of an array may have internal structure, as is often the case with spotted arrays, which it is desired to image. In this case, the mechanism for varying spot size enables, with the same instrument, measurement of fluorescence with a large laser spot and formation of a raster scan image of the internal structure using a smaller laser spot.

In addition to having 2.5 micrometer diameter focused laser spots for locating the array, or producing a raster scan, in some circumstances it is advantageous, according to the invention, to have one scanner which has optimum diameter for dwelling upon both 10 micrometer and 20 micrometer width array elements. Given a mechanism for switching between two sets of lenses and two masks, by only a small amount of additional provision, three sets of lenses and three masks, for 2.5, 5, and 10 micrometer diameter focused laser spots are advantageously provided.

A variable spot size mechanism 50 which provides computer controllable selection of three first deflector lenses, three masks, and three second deflector lenses is shown in FIG. 20A. The variable spot size mechanism carries a lens or a mask on each of nine disks 51 mounted on a shaft 52. The smaller of the three circular areas on each disk holds a lens or a mask, and the larger two circular areas are holes through which the laser beam 18 may pass unimpeded. The shaft is supported at each end by end bearings 53 which are mounted in end brackets 54. The shaft and disks are rotated by a motor 55 which drives one of the disks through a drive belt 56. In order that the shaft rotate between three precisely defined positions, there is a detenting mechanism 57 shown in detail in FIG. 20B. The detenting mechanism consists of a pair of dowel pins 58 pressed into one of the disks, a detent ball bearing 59 which is pressed against the pair of dowel pins by force provided by a spring 60. The detent ball bearing is attached to one end of a detent arm 61, which rotates about a fixed detent arm bearing 62 attached to the opposite end of the detent arm from the detent ball bearing. The force of the spring reduces any gaps between the outer race of the detent ball bearing and the dowels pins, the inner race of the detent ball bearing and the detent arm, between the inner race of the fixed detent arm bearing and the detent arm, and within the end bearings, so that the angular position of the disks and the shaft is highly repeatable. A solenoid 63 pulls the detent ball bearing out of contact with the dowel pins during the time that the motor is rotating the disks and the shaft.

Lens focal lengths, lens locations, and mask location to enable 2.5, 5, and 10 micrometer diameter focused laser spots under computer control are given in Table 3. These apply to the case that the laser is a green helium neon laser with 0.8 millimeter output beam diameter and 543.5 nanometer wavelength, the focusing lens has focal length of 3.97 millimeters, and the distance from laser to focusing lens is equal to 830.3 millimeters.

The focal lengths of the second deflector lens are chosen from those values in the Newport Corporation catalog which are available as 0.5 inch diameter piano concave or piano convex lenses. The focal lengths of the first deflector lens are achieved by combining catalog lenses with focal lengths shown as Focal Length C and Focal Length D in Table 3.

TABLE 3

| Diameter of focused laser spot, in micrometers | 2.5 | 5.0 | 10.0 |
|---|---|---|---|
| Distances, in millimeters, from laser to: | | | |
| First deflector lens | 425.4 | 456.0 | 292.2 |
| Mask | 505.1 | 597.1 | 572.3 |
| Second deflector lens | 605.5 | 687.6 | 697.6 |
| Focal lengths of lenses, in millimeters: | | | |
| First deflector lens, foclen1 | 77.58 | 135.0 | 278.9 |
| Second deflector lens, foclen2 | 100.0 | 88.3 | 100.0 |
| Catalog lenses comprising first deflector lens, dimensions in millimeters: | | | |
| Focal length C | 50.2 | 62.9 | 75.6 |
| Focal length D | −100.0 | −100.0 | −100.0 |
| Separation between lenses C and D | 14.9 | 9.5 | 2.7 |

The previous calculation, performed for 5 micrometer and 10 micrometer diameter focused laser spots separately, assumed, for simplicity, that the waist of the laser beam was coincident with the first deflector lens. The calculation of Table 3 instead takes into account the fact that the laser beam is diverging in the 292.2 to 456.0 millimeter distance from the laser to the first deflector lens.

In the case of a laser with a 0.8 millimeter diameter beam, the increase in diameter over a distance of 275 millimeters is only 4.33%. Recently lasers with small beam diameters, such as 0.1 millimeters have become available. Such a beam would expand to a diameter of 1.865 millimeters in a distance of 275 millimeters, larger than the optimum diameter for a typical acousto-optic deflector. In this case a lens or a set of lenses is inserted after the laser so as to produce a beam waist diameter in the 0.5 to 1 millimeter range located near the first deflector lens. A 118.2 millimeter focal length lens placed 118.8 millimeters from a laser with 0.1 millimeter beam waist diameter and 532 nanometer wavelength produces a 0.8 millimeter diameter beam waist 275 millimeters from the laser.

The distance from laser to the first deflector lens is made so large, i.e., greater than 275 millimeters, to accommodate two adjustable mirrors after the laser, space for the mechanism to switch lenses, and folding of the optical path so as to minimize the size of the overall package for the scanner.

The previous calculation also paid no attention to having the distance from the laser to the focusing lens be the same for all diameters of the focused laser spot, as is done here.

Figure 20C:
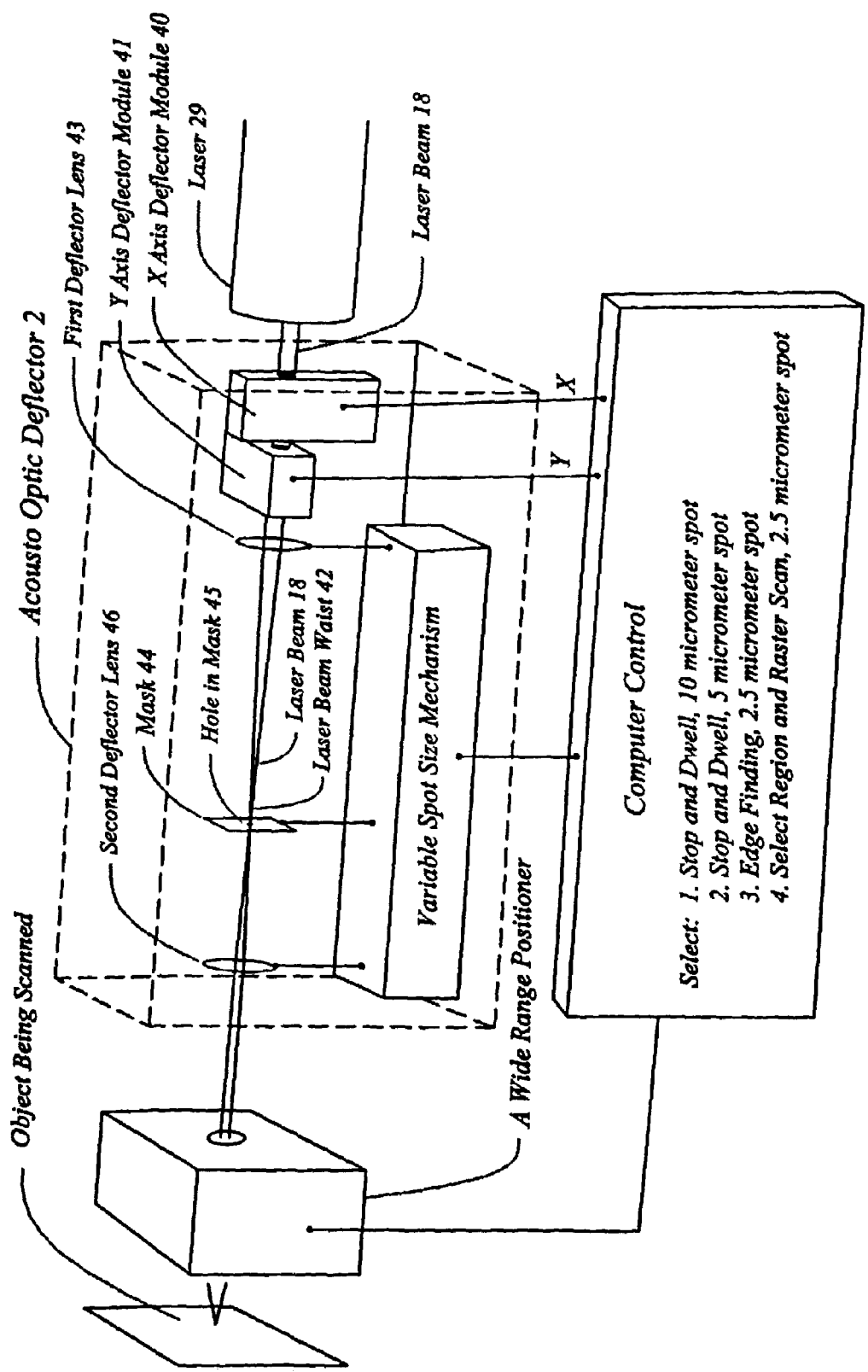
FIG. 20C illustrates a computer-controlled scanning apparatus having the optical arrangement of FIG. 20A and adapted to vary the laser spot size according to the required task.

In FIG. 20C is shown, generally, a scanner microscope system combining the inertia-less deflector and variable spot size mechanism of FIGS. 20A, the wide range positioner illustrated generally in FIG. 8 (specific implementations of which are illustrated in FIGS. 14A through 14I) and a suitable control system. As indicated, via computer control, the appropriate scan is commanded, and suitable control signals applied to the variable spot size mechanism of FIG. 20A, to the inertia-less deflector and the wide range positioner of FIG. 8. The apparatus can thus, by selection, perform a stop and dwell fluorescence scan with a 10 micrometer laser spot size, a stop and dwell fluorescence scan with a 5 micrometer laser spot size, an edge detection or array locating scan with a 2.5 micrometer laser spot size or a raster scan in a selected small region of an array or other object, employing the inertia-less deflector, using a 2.5 micrometer laser spot size. Advantageously, as previously mentioned, the apparatus may be programmed to perform a pre-scan for locating features employing the 2.5 micrometer laser spot size, and by use of the data acquired, a subsequent stop and dwell fluorescence scan is directed to the centers of the features in the array, even if they are irregularly positioned. Following this, the scientist or technician, or an automatic system, may call for certain addresses to be imaged, which is performed by a raster scan conducted by the inertia-less deflector which is taken to the appropriate address by the wide range positioner, or each of the features may be imaged in sequence. Such imaging permits examination of the details of the features, e.g. as a quality control check or as part of a scientific or clinical investigation. The feedback of position of the wide range positioner to the control for the inertia-less detector described immediately below can provide information that, by being taken in account in forming the raster scan drive signals, can permit the raster scan to be performed very quickly, before the mechanical system has settled.

Algorithm for Generating RF Frequencies

Either of the two RF frequencies is determined by the setting of a digital to analog converter which drives a voltage controlled oscillator. The setting of the digital to analog converter is changed at regular time intervals. The constancy of the time intervals makes the algorithm and the hardware implementation simplest, but is not absolutely necessary. A typical value for the time interval is one microsecond, chosen to be short compared with the dwell time on each feature, and comparable with the time required for the acousto-optic deflector to make a full scale change in the direction of the laser beam. When these criteria are met there is negligible penalty in discarding the fluorescent data from the one microsecond time interval during which the laser beam is making a full scale change in direction.

Current computer hardware can respond to an interrupt in much less than one microsecond, but often software, such as software to manage virtual memory, makes it impractical to respond once per microsecond. Therefore a good choice is to have tasks which must be done with sub-microsecond timing be done by digital logic in a field programmable gate array (FPGA). However it is simplest to describe the algorithm as if a computer responded to interrupts every microsecond. Then, depending on the computer's capabilities, one can readily partition the tasks in the algorithm between any combination of FPGA, non-programmable logic, microcontroller, personal computer, etc.

For time intervals as short as 20 microseconds, the speed of a flying lens scanner or a linear positioner may be considered constant, since the forces required to make the speed change significantly in such a short time are larger than those actually encountered. The algorithm of this preferred embodiment therefore treats the speed as constant over 20 microseconds when it predicts the position of the wide range positioner 20 microseconds into the future.

The algorithm to be described explicitly permits selection between the arc-shaped scans of a flying lens scanner, and the scans of a two dimensional linear positioner. The other wide range positioners will be seen to be special cases of these two, and can readily be implemented.

A feedback transducer in the slow positioner can yield accurate position information within one micrometer when interrogated once every 20 microseconds, therefore the algorithm presented here assumes that the position is interrogated once per 20 updates of the frequency driving the acousto optic deflector.

The wide range positioner can be constructed to have approximately constant speed in the x direction, in which case equal dwell times per feature are assured by making major changes in the RF frequency for the acousto optic deflector at the time the wide range positioner passes over the boundary between two adjacent features. One may decide to make the major changes at other times, in which case the algorithm may be more complicated. The dwell time per feature, tdwell, is greater than 20 microseconds in this embodiment, and this also makes the algorithm simpler.

Figure 21:
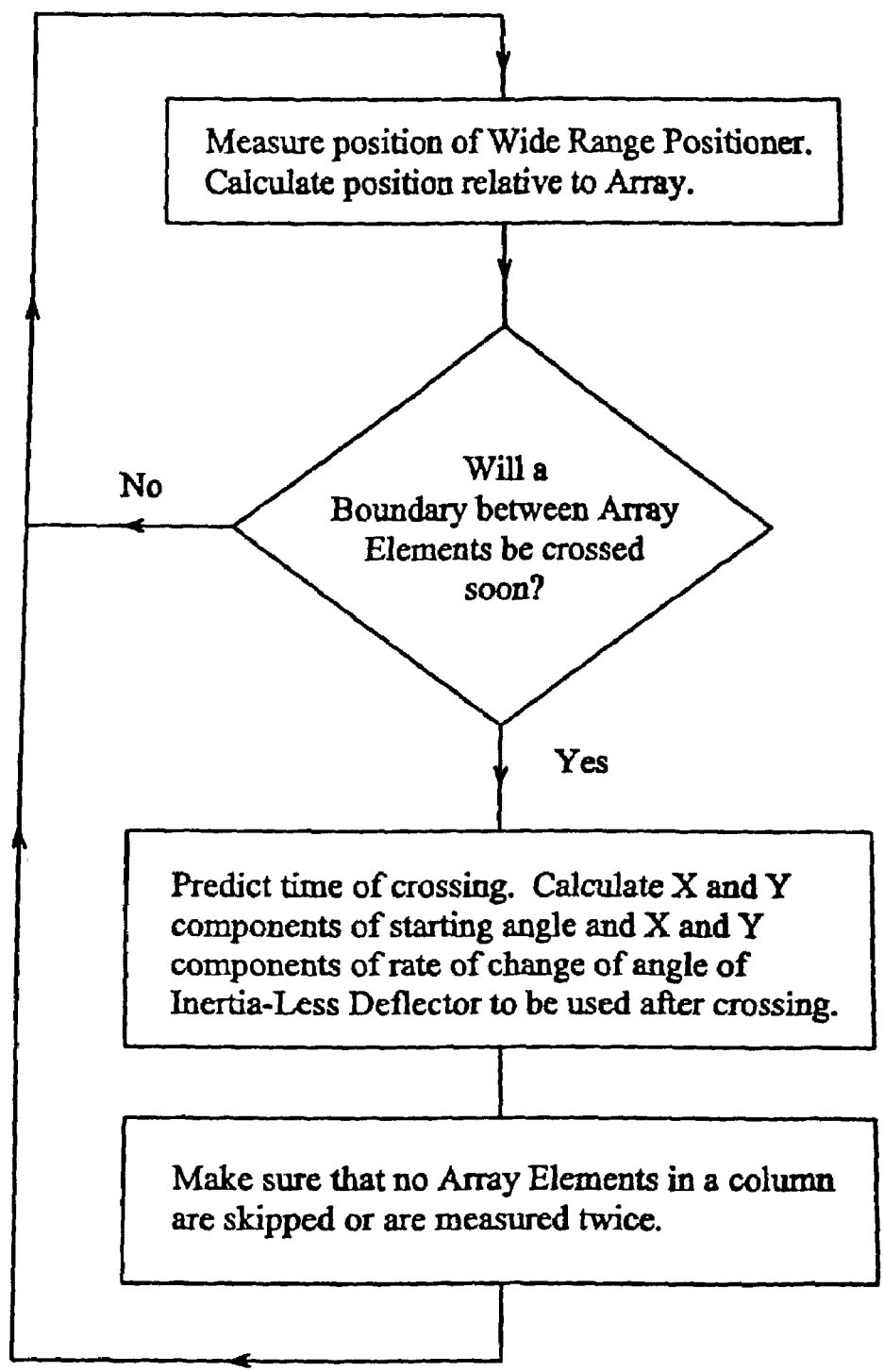
FIG. 21 is a simplified flow chart of background software tasks.
Figure 22:
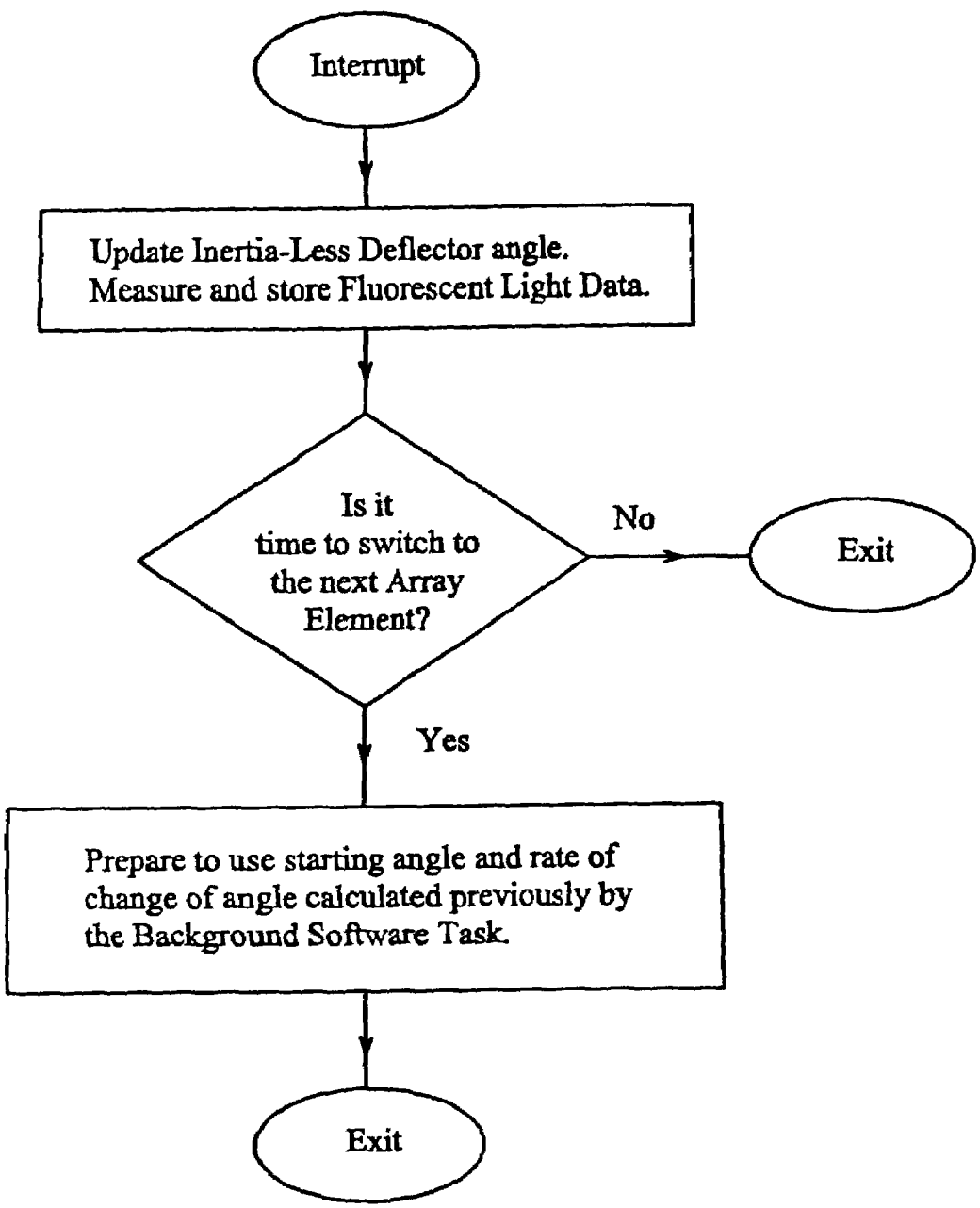
FIG. 22 is a simplified flow chart applicable to either an interrupt handler or digital logic to control the inertia-less deflector and acquisition of data on a microsecond time scale.

FIGS. 21 and 22 show a flowchart of an algorithm suitable to control the repeated "stop and dwell" action of the laser spot on successive array elements. The flowchart primarily shows the decisions that are made, typically when the wide range positioner passes over the boundary between two adjacent array elements in order to coordinate the action of the inertia-less deflector.

Figure 23A:
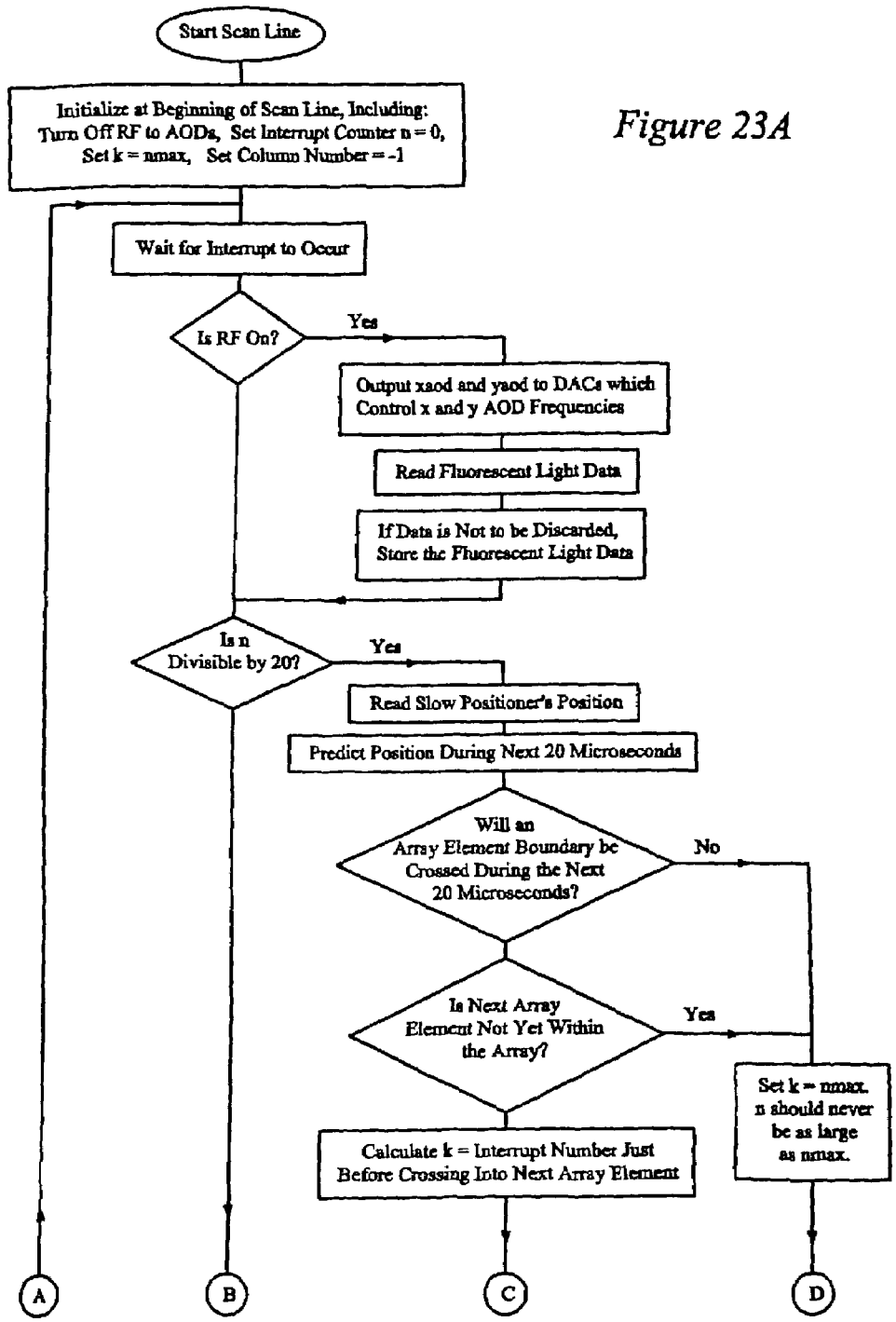
FIGS. 23A, 23B, and 23C show a more detailed flow chart of software plus digital logic to control the inertia-less deflector and acquisition of data.
Figure 23B:
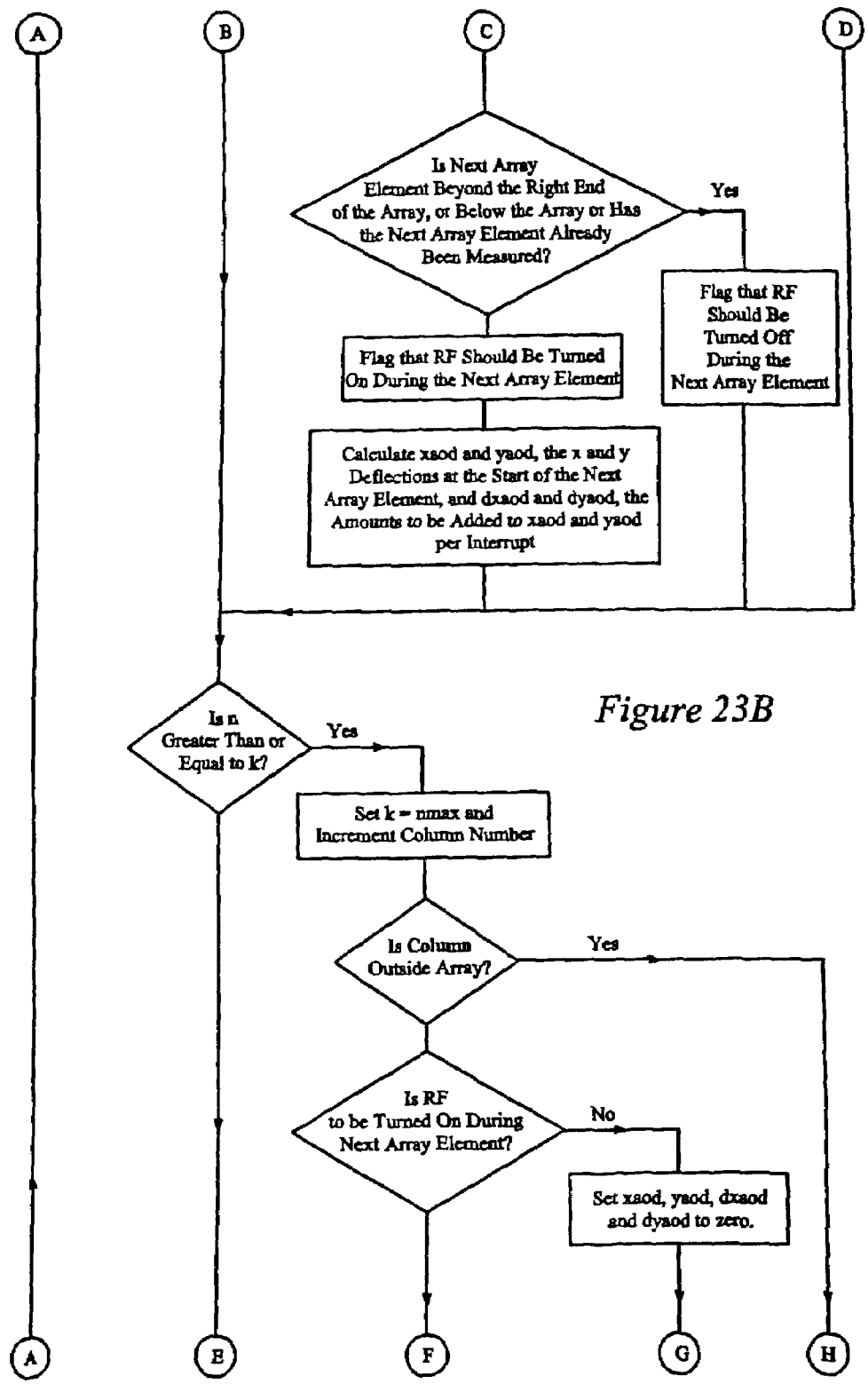
Figure 23C:
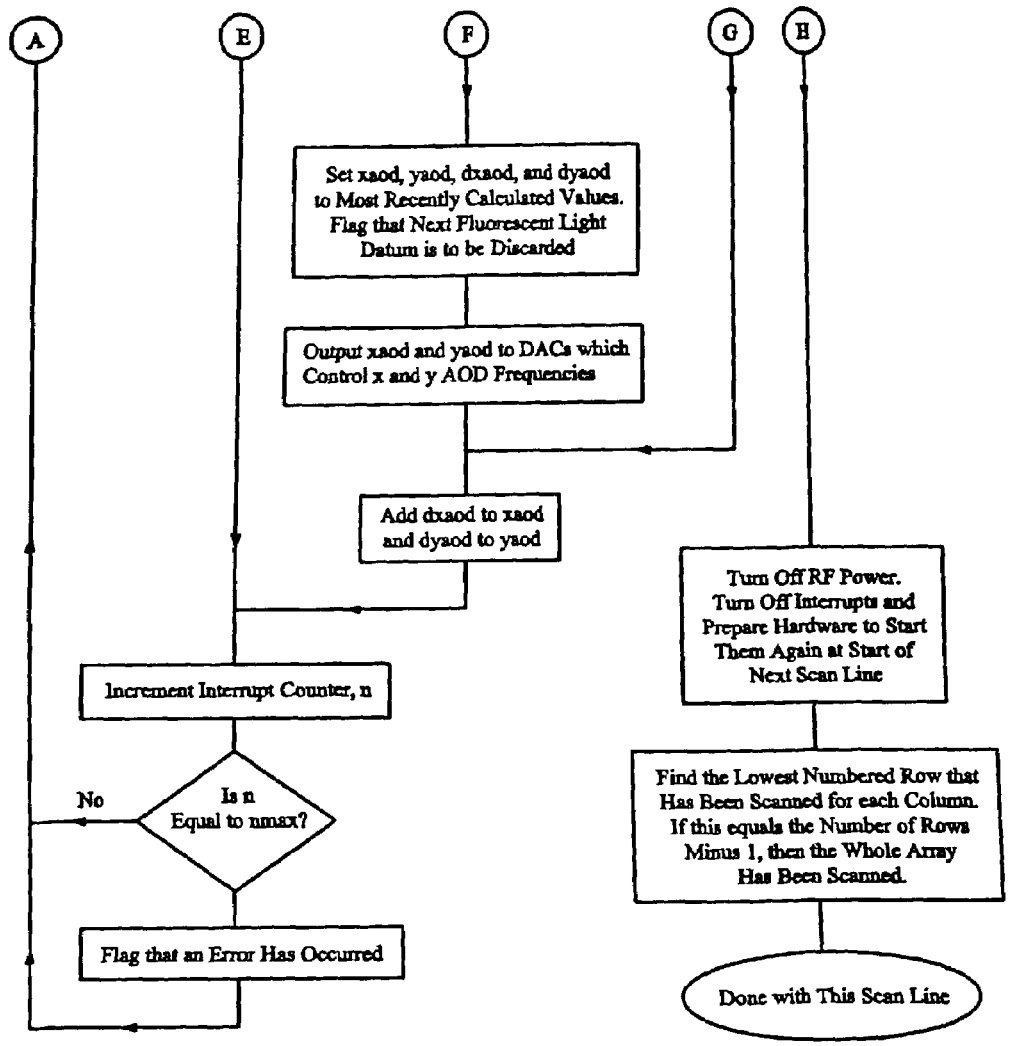

FIGS. 23A through 23C show more details for the example in which the fluorescent array is rectilinear. The detailed algorithm can of course be modified slightly to handle other arrangements, such as hexagonal close packed, sub-arrays with spaces between them, or random arrays if a scan is previously performed which locates the array members.

The calculations done within each of the square blocks in the flow charts are primarily conversions between the coordinate system of the slow, wide range positioner, the coordinate system of the fluorescent array, and the coordinate system of the inertia-less deflector, typically, in presently preferred embodiments, an acousto-optic deflector. Again, to illustrate the practicality of the invention, explicit renditions of the algorithm are given in the programs in the Computer Program Listing Appendix. The algorithm is presented in three forms in respective program modules, fs_algorithm.c, in the Computer Program Listing Appendix, presents the algorithm in its most easily understandable form, with no shortcuts taken in order to maximize speed. Distance units are meters and time units are seconds. Diagnostic capabilities and error checking are included.

fs_fast_algorithm.c, in the Computer Program Listing Appendix, is an optimization of the algorithm for speed, with calculation of sines and cosines replaced by table lookup, floating point calculations replaced by integer calculations, and units chosen to both match the units of the hardware and to optimize speed. Both fs_fast_algorithm.c and fs_algorithm.c will run in current "IBM PC" type computers, with no scanning or data acquisition hardware attached. fs_fast_algorithm.c is an order of magnitude faster than fs_algorithm.c and has a speed that enables it to scan a 640 by 640 element array (over 400,000 array elements) in less than one minute.

fs_fast.c, in the Computer Program Listing Appendix, has the same speed as fs_fast_algorithm.c, but it is organized into two separate threads of control: an interrupt handler which executes once every microsecond, and a background task which loops, looking at the progress of the interrupt handler. The interrupt handler reads fluorescent light, adds it to the appropriate previously accumulated value in a 640 by 640 array, and updates the deflection angle of the acousto-optic deflector. The interrupt handler executes in less than ½ microsecond in a typical computer, and therefore requires an interrupt latency less than ½ microsecond. This is typically provided by a dedicated computer or the code in the interrupt handler is implemented in a field programmable gate array (FPGA), such as that shown in FIGS. 19A through 19D, to which is connected at least 2.4576 Megabytes of semiconductor memory for data storage.

At every twentieth interrupt the background task checks whether a feature boundary is about to be crossed, and if so, prepares new parameter values for use by the interrupt handler, and sets a parameter k, which tells the interrupt handler when to switch to the new values. The background task also reads and controls the position of the slow, wide range positioner, assesses the overall progress of the scanning process, and turns interrupts on at the start of each scan line. The interrupt handler turns the interrupts off at the end of each scan line.

The connection between the interrupt handler and the background task in fs_fast.c is tolerant to delays of the background task. Such delays will have negligible effect, the primary effect being spending slightly more or less time collecting data from a feature.

Also included in the Computer Program Listing Appendix are program modules which enable the testing of fs_algorithm.c and fs_fast_algorithm.c. These are:

fs_main.c, in the Computer Program Listing Appendix, a main program which performs initialization and diagnostic report generation, and which calls either the routine get_array_data in fs_algorithm.c or get_array_data_fast in fs_fast_algorithm.c depending upon whether a variable, named fast, is set equal to zero or is nonzero.

fs_support.c, in the Computer Program Listing Appendix, which provides routines to be called by the three algorithm routines. They provide simulated data, make statistical measurements and do error checking. In the presence of actual hardware, these functions are replaced by hardware IO instructions.

simul_motion.c, in the Computer Program Listing Appendix, which creates simulated motion data for testing the algorithm. It adds random noise to the y motion and sinusoidal errors to the angular motion.

The modules fs_main.c, fs_algorithm.c, fs_fast_algorithm.c, fs_support.c, and simul_motion.c, but not fs_fast.c, will compile, link together, and run together using the C compiler and development environment provided by Microsoft Visual Studio.

The above code does not generate the y axis motion and either x axis or angular motion in a scanner. Hardware and software, used in existing wide range scanners of the various available types provide these functions. Code controls for clocks for generating interrupts are likewise routine.

To ensure complete coverage of an array, an advantageous property of y motion is a provision that the increment in y per scan be slightly less than the pitch between rows of the array. The code in simul_motion.c assumes that the average increment in y per scan is 95% of the pitch between rows of the array and that there is random error in y which is 10% of the pitch between rows of the array.

Examination of the above described algorithm shows that minor modifications enable the inertia-less deflector to produce raster scans superimposed on the "stop and "dwell" motion which cancels out the continuous motion of the wide range position. This is useful in finding edges of features or in producing an image of small areas of a feature at an address to which the wide range positioner delivers the laser spot. The variable spot size mechanism previously described allows one to produce high resolution images with a small spot either before or after an array is scanned with a large spot in "stop and dwell" mode.

Embodiments Having Provision for Random Access

As previously mentioned, according to another aspect of the present invention, in respect e.g. of a random access positioner, an inertia-less deflector is arranged to increase throughput by counter moving the beam in controlled relation to sensed settling movements of the mechanical scanning system, to achieve a "stopped" beam despite persisting oscillations of the mechanical system. This decreases the time required for the laser beam to be accurately aimed at a biological feature or a conductor or link as in repair of a computer memory chip. In addition to use in random access instruments for life sciences, this feature is therefore useful in memory repair systems.

Figure 24:
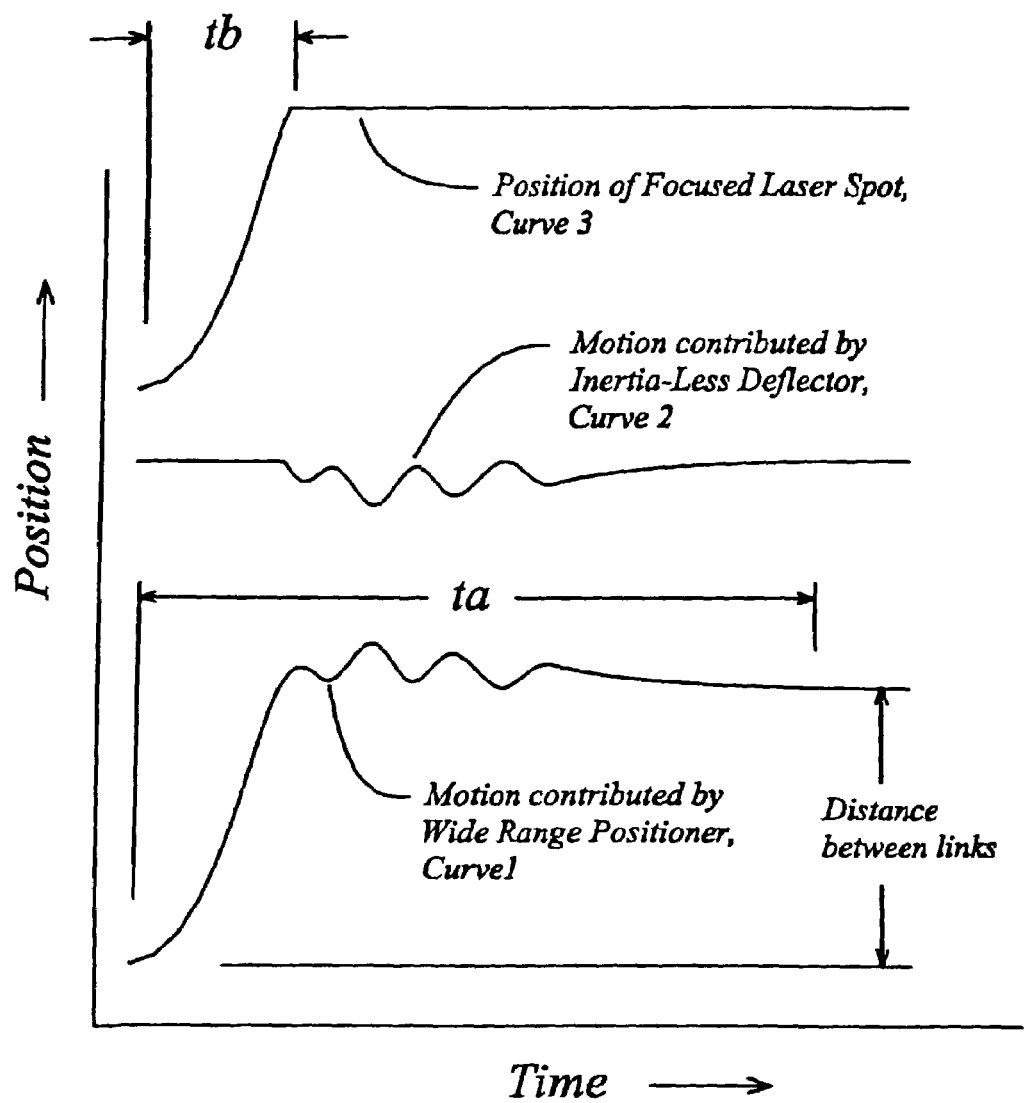
FIG. 24 shows an embodiment of the invention that cancels transients in a wide range positioner with high effectiveness.
Figure 25:
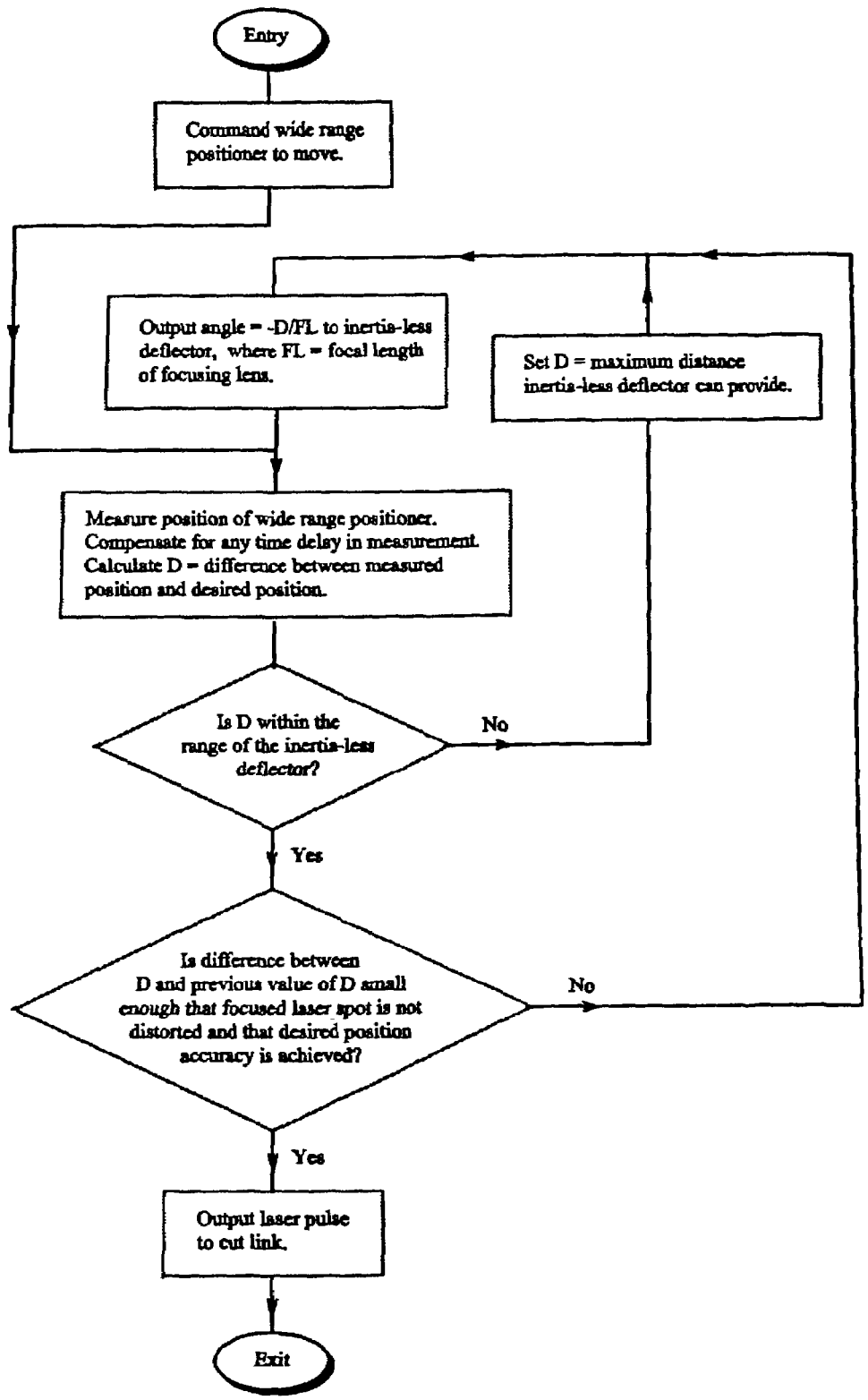
FIG. 25 is a flow chart of an algorithm for control of an inertia-less deflector for canceling transients.

Curve 1 in FIG. 24 shows an oscillatory transient in the motion of the wide range positioner. Curve 2 in FIG. 24 shows the same oscillatory transient, but with opposite sign, produced by the inertia-less deflector under an algorithm controlling its angle, similar, in this respect to the algorithms just described. The sum of the motion of the wide range positioner and the motion produced by the inertia-less deflector produce the position versus time shown in Curve 3 in FIG. 24. The time required to achieve a precise position in the absence of the inertia-less deflector is indicated by ta. The much shorter time achieved by the present invention is indicated by tb. FIG. 25 is a flow chart which explains the sequence of events when canceling transients.

In the past, galvanometers have been used in conjunction with X, Y stages to seek a somewhat similar result. An example is described in U.S. Pat. No. 4,532,402. But the time required for a galvanometer to compensate for the transient in an X, Y stage is in the range of 0.1 to 2 milliseconds. In contrast, the algorithm-controlled inertia-less deflector as described requires only of the order of one microsecond to accomplish this task, providing a significant advantage in speed over the galvanometer. Rather than being impractical to control an inertia-less deflector for this purpose, as may previously been assumed, I realize this to be practical and in some ways even simpler to accomplish than with prior systems. Because of the significant time delay associated with a galvanometer's motion in seeking to counter settling motions with a galvanometer, one must try to predict the position of the wide range positioner after this time has elapsed. In contrast, with the inertia-less deflector according to the present invention, one can simply set the inertia-less deflector's angle so that its angle multiplied by the focal length of the focusing lens equals minus the position error of the wide range positioner.

In laser-based microscopic instruments, memory repair systems and other laser systems there can be a problem that the position of a workpiece relative to a wide range positioner is not known accurately enough when the laser system starts to process the workpiece. A common way to find the location of the workpiece is to scan an attenuated laser beam over characteristic features of the workpiece, and to sense laser light reflected from the workpiece. Galvanometers have been seen as the fastest way to find the locations of these characteristic features.

According to another aspect of the present invention, an improved system employs an inertia-less detector implemented in the following way. FIG. 26A shows a plan view of the border between a region on the left that produces a small amount of detected light and a region on the right which produces a large amount of light. By "produces light" we mean that the light may be reflected light, transmitted, or fluorescent light. The boundary between these two regions is referred to as an "edge", and the objective is to find the precise location of the edge.

Also shown in FIG. 26A is the position of the focused laser spot as it moves from the region on the left to the region on the right. The circles indicate the positions of the focused laser spot at the times that light measurements are made. The spacing between these positions is typically between ⅓ and ⅔ of a spot diameter.

FIG. 26B shows the quantity QA=the amount of light that would be detected as the focused laser spot moves across the edge in the case that the diameter of the focused laser spot is infinitesimally small.

FIG. 26C shows QB=the power distribution in the focused laser spot, or the amount of light that would be measured if the focused laser spot moved from left to right across a narrow reflective line.

FIG. 26D shows QC=the amount of light measured as the focused laser spot characterized by QB moves across the edge. The dots indicate positions at which a light measurement is made.

In the case that the noise in the measurement is dominated by photoelectron statistics, as is the case in many applications of the present invention, a useful method for finding the location of the edge is, in real time, employing the inertia-less deflector to take readings across an edge, fit a suitable curve, e.g. a parabola, to a plot that convolves the derivative of the characteristic power distribution across the laser spot and measured light readings, and determine the location of the maximum of the fitted curve as the location of the edge.

An illustrative example is as follows: Form QD=the derivative of QB, and calculate the convolution of QD and QC. This convolution is shown as QE. QD is shown in FIG. 26E and QE is shown in FIG. 26F. The dots on the curve of QD indicate the (typically) seven discrete values of QD that are used in calculating the convolution. Similarly the dots on the curve of QE indicate the discrete values of QE that are calculated. If the values of QD are indicated by numbers −3, −2, −1, 0, 1, 2, and 3, then the ith value of QE=QE[i]=QC[i−3]QD[−3]+QC[i−2]QD[−2]+QC[i−1]QD[−1]+QC[i]QD[0]+QC[i+1]QD[1]+QC[i+2]QD[2]+QC[i+3]QD[3].

The best estimate, in a maximum likelihood sense, of the location of the edge is the place at which QE is a maximum. This maximum will typically not occur at any one of the discrete data points. A curve is fit to the data points and the location of the maximum of the fitted curve determined as the edge location.

In actual practice QB and QC are not exactly as shown. A method of fitting a curve to the data which is least sensitive to this fact, has been found empirically to be the following: Fit a parabola to either A. the three largest values of QE, or B. the values of QE which are greater than 70% of the maximum value of QE. Choice is made between these based upon which provides the most data points. A purpose of option B is to avoid fitting a parabola to three points in the case that the measurements are too close together and the three highest points are near the peak of QE. In this case the noise in the data can yield very wrong results.

The parabola found by fitting the top three points of QE shown in FIG. 26F is indicated by QF and the location of its maximum is indicated by QG.

The starting position for the focused laser spot is to the left of the nominal position of the edge by at least the sum of the maximum position error of the edge plus one diameter of the focused laser spot, and similarly the ending position is to the right of the nominal position by the same amount.

If the distance between measurements is ⅓ the diameter of the focused laser spot, then the number of measurements is 6+6 times (maximum position error)/(diameter of focused laser spot.) If the maximum error=20 micrometers and the diameter of the focused laser spot is 5 micrometers, then there are 30 measurements. A typical time between measurements employing the inertia-less deflector is one microsecond, so the entire process requires 30 microseconds. In comparison, such a process typically requires tens of milliseconds when galvanometers are used.

The signal to noise ratio of this method which uses a focused laser beam is typically much higher than imaging methods, such as those using CCD cameras.

I have shown principles by which improved scanning microscopes, fluorescence detection systems and laser beam positioners can be constructed and operated with significant advantages. For example, in the case of detecting fluorescence from features of a micro-array, system principles have been shown which enable a focused laser spot to be made to dwell upon a feature of a micro-array for a time in the range of 10 to 1000 microseconds while an associated wide range positioner may steadily advance. The time for the spot then to advance to the next feature is advantageously no more than 10% of the dwell time and in most preferred cases, less than 1% of the dwell time, making the dwell portion of the duty cycle at least 90% and in preferred cases, at least 99%. A preliminary scan for locating an array can be accomplished in a relatively small fraction of the total scan time, typically within 10% of that time. Similar and other advantages are achievable with embodiments used for the other purposes described.

Accordingly, the invention is submitted to represent a significant advance in many aspects with respect to scanning microscopy, fluorescence detection and laser beam positioning.

Numerous other embodiments of the foregoing features will occur to those skilled in the art and are included in the spirit and scope of the claims.

What is claimed is:

1. A microscope scanner, for instance a fluorescence scanner, constructed to scan a focused spot over locations on an extended surface, the focused spot produced via an optical path from a focusing lens, the scanner comprising:
a wide range positioner having inertia and
a simultaneously acting substantially inertia-less deflector that includes a deflector control;
the wide range positioner capable of producing relative scanning motion in a scanning direction between the focused spot and the extended surface;
the control of the substantially inertia-less deflector adapted to cause the deflector to produce a progressive change in the angle of the optical path from the focusing lens to the surface, the change being within a limited range and in a stabilizing direction that is, substantially, along the same line as, but opposite to, the direction of scanning motion to cause the focused spot to substantially stabilize, for example to stop or dwell, upon a location on the surface during the scanning motion produced by the wide range positioner.

2. The microscope scanner of claim 1 in which the substantially inertia-less deflector is associated with a set of deflector lenses that direct a beam to a constant position over a range of deflection of said deflector.

3. The microscope scanner of claim 1 in which the substantially inertia-less deflector comprises at least two substantially inertia-less deflector modules arranged to act along different coordinates.

4. The microscope scanner of claim 1 constructed to advance the scan in the scanning direction along a predetermined scan path over the surface.

5. A laser beam positioner constructed to scan a focused laser spot over locations on an extended surface, the focused spot produced via an optical path from a focusing lens, the laser beam positioner comprising:
a wide range positioner having inertia,
and a simultaneously acting substantially inertia-less deflector that includes a deflector control;
the wide range positioner capable of producing relative motion in a scanning direction between the focused spot and the extended surface;
the control of the substantially inertia-less deflector adapted to cause the substantially inertia-less deflector to produce a progressive change in the angle of the optical path from the focusing lens to the surface, the change being within a limited range and in a stabilizing direction that is, substantially, along the same line as, but opposite to, the direction of scanning motion to cause the focused laser spot to substantially stabilize, for example to stop or dwell, upon a location on the surface during the scanning motion produced by the wide range positioner.

6. The microscope scanner of claim 1, 4 or 5 in which the deflector control is adapted to cause successive changes in the angle of the optical path, the changes comprising, first, said change of the angle in the stabilizing direction substantially opposite to said scanning motion for substantially stabilizing the spot upon a location on the extended surface, and second, a change in a direction substantially opposite to the stabilizing direction, to advance the angle relatively quickly in the direction of the scanning motion to change the location upon which the focused spot is directed, cumulative time elapsed during first and second successive changes in the angle defining a duty cycle of the substantially inertia-less deflector.

7. The microscope scanner of claim 6 in which the duration of the first said change of the angle of the substantially inertia-less deflector is at least 90% of the duty cycle.

8. The microscope scanner of claim 1 in which said deflector control is adapted to hold said focused spot substantially stationary on a location on said surface for a time between 10 and 1000 microseconds during the scanning motion of the wide range positioner.

9. The microscope scanner of claim 1 or the laser beam positioner of claim 5 in which (a) the deflector control is adapted to progressively change the angle of the optical path in said stabilizing direction at a rate to cause the focused spot to dwell upon a location on the surface during advance of the wide range positioner at an approximately constant speed over a distance at least as large as the dimension of the focused spot in the direction of a scan path, and (b) the deflector control is adapted, thereafter, to change the angle of the optical path in the direction substantially opposite to the stabilizing direction at a substantially faster rate, for example at a rate ten times faster, to shift the incidence of the focused spot to another location on the surface.

10. The microscope scanner or laser beam positioner of claim 9 in which the deflector control is adapted to move said focused spot on said extended surface in a direction along said scan path, over a distance corresponding to a small multiple of the dimension of the focused spot in the direction along the scan path, in a time less than about ten percent of the time in which the substantially inertia-less deflector is adapted to cause the focused spot to dwell upon a location on the surface.

11. The microscope scanner of claim 1 or laser beam positioner of claim 5 in which the wide range positioner is adapted to scan the focused spot along the extended surface over a distance more than ten times the dimension corresponding to the range of deflection of the substantially inertia-less deflector.

12. The microscope scanner of claim 1 including a laser producing a laser beam arranged to be deflected by said substantially inertia-less deflector and travel through the focusing lens to define the focused spot on the surface.

13. The microscope scanner of claim 1 or the laser beam positioner of claim 5 including a detector, the focusing lens arranged to gather light emanating from the region of the focused spot on the extended surface and direct it to the detector to produce data in the form of measured light readings.

14. The microscope scanner or laser beam positioner of claim 13 associated with software adapted to implement an edge detection algorithm operating on said data produced by advance of the focused spot over the surface, the algorithm effective to detect the edges of features at locations on the surface.

15. The microscope scanner of claim 14 in which the software is in machine readable form and is arranged to fit a curve such as a parabola to ascending and descending points in the convolution of the measured light readings and the derivative of characteristic power distribution across the laser spot, and to locate the edge of a feature at the maximum value of the curve fitted to the convolution.

16. The microscope scanner of claim 15 in which detected edge information is used in controlling said deflector.

17. The microscope scanner of claim 16 adapted to conduct a pre-scan to detect locations of edges of features on the surface and to utilize that information in a subsequent scan in which the focused spot is caused to dwell upon individual features.

18. The microscope scanner of claim 17 in which excursions of a laser beam over an edge of a feature for detecting location of the edge are produced by said substantially inertia-less deflector.

19. The microscope scanner of claim 1 including a fluorescence detector and a laser, the laser selected and arranged so that its beam forms the focused spot in manner suitable to excite fluorescence from said location on said surface, the scanner arranged so that fluorescent light from said location travels through said focusing lens into said fluorescence detector, and further comprising a system for collecting data from said fluorescence detector and assigning said data to respective locations on the surface.

20. The microscope scanner of claim 19 in which said fluorescence detector comprises a tube lens, a pinhole, and a photodetector such as a photomultiplier, said focusing lens, said tube lens, and said pinhole combined to effectively form a confocal microscope, and an emission filter is arranged to pass fluorescent light to said photo detector and reject laser light.

21. The microscope scanner of claim 1, 19 or 20 in which locations on said extended surface define an array or arrays of biochemical material.

22. The microscope scanner of claim 21 including an array of known fragments of genetic material hybridized with an unknown genetic material.

23. The microscope scanner of claim 22 in which said unknown genetic material has attached to it fluorophores with an excitation cross section larger than $4 \times 10^{-20}$ square meter and said focused spot comprises a laser spot of wavelength selected to excite said fluorophores.

24. The microscope scanner of claim 19 in which fluorescent light from said location that passes through the focusing lens and tube lens, is focused at said pinhole, the pinhole sized to pass the focused fluorescent light over a range of lateral movement, of the focused light at the pinhole, attributable to the progressive change in the angle of the optical path produced by the substantially inertia-less deflector.

25. The microscope scanner of claim 24 in which the substantially inertia-less deflector is an acousto-optic deflector.

26. The microscope of claim 24 in which the pinhole is formed by physical structure, the transverse dimension of the pinhole being substantially larger than a transiting beam that defines the focused spot, the dimension sized to accommodate varying location of the beam responsive to deflections produced by the substantially inertia-less deflector.

27. The microscope scanner of claim 1 in which the diameter of the focused spot is larger than one fifth of the X or Y dimensions of a feature at said location.

28. A laser beam positioner constructed to position a focused laser spot at a selected location on an extended surface via an optical path from a focusing lens, comprising:
a wide range positioner
and a substantially inertia-less deflector that includes a deflector control;
the wide range positioner having inertia and adapted to cause the spot to move to, and stop at, a location on the surface having a specific address;
the deflector control adapted to cause the substantially inertia-less deflector to change the angle of the optical path within a limited range,
and a position sensor for tracking the instantaneous position of the wide range positioner relative to the location on the surface having the specific address,
the position sensor arranged to provide to the deflector control an instantaneous signal of the position of the wide range positioner during settling motions of the wide range positioner while it is stopping the focused spot at the address, the deflector control responsive to the signal to cause the substantially inertia-less deflector to change the angle of the optical path from the focusing lens to the extended surface in directions that are, substantially, along the same lines as and opposite in direction to the respective instantaneous settling motions of the wide range positioner to cause the focused spot to be substantially directed upon the respective location on the surface before said settling motions end.

29. The microscope scanner of claim 1 or the laser beam positioner of claim 28 or 5 in which said substantially inertia-less deflector is associated with a first deflector lens which focuses through a hole in a mask, and a second deflector lens arranged such that said first and second deflector lenses are capable of creating an image on the focusing lens at the same position on the focusing lens over the range of angles of deflection of said substantially inertia-less deflector, thereby causing said optical path to rotate about said focusing lens during deflection of said substantially inertia-less deflector, said mask arranged to block light other than that deflected in first order by said substantially inertia-less deflector, the focal lengths and locations of said first and second deflector lenses, in conjunction with the initial diameter of a defined input beam and the focal length of said focusing lens, determining the diameter of said focused spot on said surface.

30. The microscope scanner or laser beam positioner of claim 29 further comprising a lens changing mechanism, such as a turret, for switching between several sets of said first deflector lens, said mask, and said second deflector lens, enabling the diameter of said focused spot on said surface to be varied by actuation of said lens-changing mechanism.

31. The microscope scanner or laser beam positioner of claim 30 in which said lens-changing mechanism comprises a turret having first and second lens carriers spaced apart along the optical path, the lens carriers carrying respectively all of the first deflector lenses and second deflector lenses, and masks associated with respective deflector lens sets disposed between said lens carriers.

32. The microscope scanner of claim 1 or the laser beam positioner of claim 5 adapted to address a succession of features on said extended surface, the substantially inertia-less deflector control adapted to cause the focused spot to sweep rapidly over edge regions of the features and to dwell for relatively long intervals upon areas of the features inwardly from their edges.

33. The microscope scanner or laser beam positioner of claim 32 constructed and arranged to produce successive scan paths of the focused spot that overlap at least slightly and a control adapted to identify locations which have previously been dwelled upon and cause the focused spot to pass over said locations without said focused spot dwelling upon them again.

34. The microscope scanner of claim 1 or the laser beam positioner of claim 5 having a non-scanning mode of operation that involves moving the wide range positioner to cause a focused spot to move to and stop at a location on the extended surface having a specific address,
the microscope scanner including a position sensor for tracking the instantaneous position of the wide range positioner relative to the location on the surface having the specific address,
the position sensor arranged to provide to the deflector control an instantaneous signal of the position of the wide range positioner during settling motions of the wide range positioner while it is stopping the focused spot at the address, the deflector control responsive to the signal to cause the substantially inertia-less deflector to change the angle of the optical path from the focusing lens to the surface in directions that are, substantially, along the same lines as and opposite in direction to respective instantaneous settling motions of the wide range positioner to cause the focused spot to be substantially directed upon the respective location on the surface before said settling motions end.

35. The microscope scanner of claim 34 in which the settling motions and the opposite motions produced by said substantially inertia-less deflector effectively stop said focused spot at said address.

36. The laser beam positioner of claim 28 in which the settling motions and the opposite motions produced by said substantially inertia-less deflector effectively stop said focused spot at said address.

37. The microscope scanner of claim 1 adapted to focus a spot of a laser beam on said surface, or the laser beam positioner of claim 28 or 5, in which the diameter of the spot produced by said laser beam on said surface is variable.

38. The microscope scanner of claim 1 or the laser beam positioner of claim 28 or 5 in which said deflector control for said substantially inertia-less deflector is adapted to keep said focused spot approximately centered on elements of an array.

39. The microscope scanner of claim 1 or the laser beam positioner of claim 5 in which said control associated with the substantially inertia-less deflector generates RF waveforms with sawtooth frequency versus time behavior adapted to cause said substantially inertia-less deflector to substantially cancel, for successive short periods of time, the effect of the wide range positioner.

40. The microscope scanner of claim 1 or the laser beam positioner of claim 28 or 5 in which said wide range positioner comprises a two dimensional galvanometer scanner which moves an incident beam over a fixed focusing lens and fixed extended surface.

41. The microscope scanner of claim 1 or the laser beam positioner of claim 28 or 5 in which said wide range positioner comprises a two dimensional linear positioner which moves said surface relative to a fixed focusing lens.

42. The microscope scanner of claim 1 or the laser beam positioner of claim 28 or 5 in which said wide range positioner comprises a two dimensional linear positioner which moves said focusing lens relative to a fixed surface.

43. The microscope scanner of claim 1 or the laser beam positioner of claim 28 or 5 in which said wide range positioner comprises a one or two dimensional linear positioner which moves said focusing lens and a one or two dimensional linear positioner which moves said surface.

44. The microscope scanner of claim 1 or the laser beam positioner of claim 28 or 5 in which said wide range positioner comprises a one or two dimensional galvanometer scanner and a one or two dimensional linear positioner which moves said surface.

45. The microscope scanner of claim 1 or the laser beam positioner of claim 28 or 5 in which said wide range positioner comprises a one or two dimensional galvanometer scanner and a one or two dimensional linear positioner which moves said galvanometer scanner relative to said surface.

46. The microscope scanner of claim 1 or the laser beam positioner of claim 28 or 5 in which said wide range positioner comprises a flying lens scanner for moving said focusing lens and a one or two dimensional linear positioner which moves said surface.

47. The microscope scanner of claim 1 or the laser beam positioner of claim 28 or 5 in which said wide range positioner comprises a flying lens scanner and a one or two dimensional linear positioner which moves said flying lens scanner relative to said surface.

48. The microscope scanner of claim 1 or the laser beam positioner of claim 28 or 5 in which said wide range positioner comprises a rotating polygon and a one or two dimensional linear positioner which moves said surface.

49. The microscope scanner of claim 1 or the laser beam positioner of claim 28 or 5 in which said wide range positioner comprises a rotating polygon and a one or two dimensional linear positioner which moves said rotating polygon relative to said workpiece.

50. The microscope scanner of claim 1 or the laser beam positioner of claim 28 or 5 in which said wide range positioner comprises a rotating turntable which moves the surface formed by one or more workpieces and a linear positioner which moves said focusing lens relative to said turntable.

51. The microscope scanner of claim 1 or the laser beam positioner of claim 28 or 5 in which said wide range positioner comprises a rotating turntable which moves the surface formed by one or more workpieces and a one or two dimensional galvanometer scanner.

52. The microscope scanner of claim 1 or the laser beam positioner of claim 28 or 5 in which said wide range positioner comprises a rotating turntable which moves the surface formed by one or more workpieces and a flying lens scanner which moves said focusing lens.

53. The microscope scanner of claim 1 or the laser beam positioner of claim 28 or 5 in which said wide range positioner comprises a rotating table which moves said focusing lens over the surface formed by one or more workpieces and a one or two dimensional linear positioner which moves said surface.

54. The microscope scanner of claim 1 or the laser beam positioner of claim 28 or 5 in which said wide range positioner comprises a rotating polygon and a rotating turntable which moves the surface formed by one or more workpieces.

55. The microscope scanner of claim 1 or the laser beam positioner of claim 28 or 5 in which said focusing lens is a microscope objective.

56. The microscope scanner of claim 1 or the laser beam positioner of claim 28 or 5 constructed and arranged for randomly accessing features at locations on said surface with said wide range positioner and conducting a sweeping scan of a respective feature by said substantially inertia-less deflector.

57. The microscope scanner or laser beam positioner of claim 56 in which said sweeping scan is implemented in a manner to detect locations of features on said surface.

58. The microscope scanner or laser beam positioner of claim 56 in which the substantially inertia-less deflector comprises two substantially inertia-less deflector modules arranged to act along different coordinates and the microscope scanner or laser beam positioner is constructed and arranged to conduct a raster scan of said feature.

59. The microscope scanner or laser beam positioner of claim 58 in which said raster scan is implemented in a manner to image said feature.

60. The microscope scanner or laser beam positioner of claim 56 constructed and arranged to perform a stop and dwell scan of features on said surface employing a first laser spot size and to conduct said sweeping scan or raster scan with a laser spot size smaller than said first spot size.

61. A method of scanning or positioning a laser beam employing the microscope scanner of claim 1.

62. The microscope scanner of claim 1 or the laser beam positioner of claim 28 or 5 in which the substantially inertia-less deflector is mounted on a stationary support.

63. A method of positioning a laser beam employing the laser beam positioner of claim 28 or 5.

64. The method of claim 63 adapted to read fluorescence from features arrayed on a surface in which the features are arranged at a density in excess of 10,000 features per square centimeter.

65. The method of claim 64 in which the features are arranged at a density in the range between about 40,000 and 1,000,000 features per square centimeter.

66. A fluorescent scanner arranged to produce a laser beam that excites fluorescence at locations on a surface, the scanner comprising a mechanical system having inertia constructed to move the laser beam along a line in a scanning direction relatively over the surface, the mechanical system combined with a substantially inertia-less deflector in the form of an acousto-optic deflector, the acousto-optic deflector constructed and arranged to produce fine changes in the angle of the laser beam simultaneously with and, substantially, along the same line of movement as that of the mechanical system, but in direction opposite thereto, in manner to prolong the duration of incidence of the beam at a selected location during said movement of said mechanical system.

67. A fluorescent scanner arranged to produce a laser beam that excites fluorescence at locations on a surface, the scanner comprising a mechanical system having inertia constructed to move the laser beam along a line in a scanning direction relatively over the surface, the mechanical system combined with a substantially inertia-less deflector in the form of an electro-optic deflector, the electro-optic deflector constructed and arranged to produce fine changes in the angle of the laser beam simultaneously with and, substantially, along the same line of movement as that of the mechanical system but in direction opposite thereto, in manner to prolong the duration of incidence of the beam at a selected location during said movement of said mechanical system.

68. A fluorescence scanner comprising scanning apparatus constructed and controlled to scan a laser beam relatively across an extended surface to excite fluorophores associated with features on the surface and to detect fluorescence from the excited fluorophores, characterized in that the scanner includes a wide range positioner having inertia, the wide range poistioner constructed to move a focusing lens for effecting scan of a focused spot over the surface and at least one substantially inertia-less deflector including a deflector control constructed to operate simultaneously with the wide range positioner to change the angle of the scanned laser beam upon the focusing lens, substantially, in a direction along the same line as, but in direction opposite to, the direction of the scanning motion of the focusing lens to prolong the incidence of the laser spot on the region of the feature inwardly of its boundary during the course of the scan.

* * * * *

UNITED STATES PATENT AND TRADEMARK OFFICE
CERTIFICATE OF CORRECTION

PATENT NO. : 7,050,208 B2
APPLICATION NO. : 10/305696
DATED : May 23, 2006
INVENTOR(S) : James W. Overbeck It is certified that error appears in the above-identified patent and that said Letters Patent is hereby corrected as shown below:

Column 1, line 61,
    Delete "oligonucleoitides", insert -- oligonucleotides --

Column 13, line 3, Equation 1 is incorrect
    Delete: "$J_2 = Y(N/T) = Y(N_0/T) \times (J_1\sigma + 1/T)$",
    insert -- $J_2 = Y(N/T) = Y(N_0/T) \times (J_1\sigma /( J_1\sigma + 1/T))$ --

Column 13, line 10,
    "per unit area" should read -- per unit area --

Column 13, line 11,
    "per array element" should read -- per array element --

Column 13, line 12,
    "per array element" should read -- per array element --

Column 29, third from last line in Table 2,
    Delete "0.0808", insert -- 0.808 --

Column 41, line 5
    Delete "position", insert -- positioner --

Column 42, line 5
    Delete "detector", insert -- deflector --

UNITED STATES PATENT AND TRADEMARK OFFICE
CERTIFICATE OF CORRECTION

PATENT NO. : 7,050,208 B2
APPLICATION NO. : 10/305696
DATED : May 23, 2006
INVENTOR(S) : James W. Overbeck It is certified that error appears in the above-identified patent and that said Letters Patent is hereby corrected as shown below:

Claim 68, Column 68, line 45
Delete "poisitioner", insert -- positioner --

Signed and Sealed this

Fifth Day of December, 2006

JON W. DUDAS
*Director of the United States Patent and Trademark Office*